US009427316B2

(12) United States Patent
Schweich, Jr. et al.

(10) Patent No.: US 9,427,316 B2
(45) Date of Patent: *Aug. 30, 2016

(54) VALVE REPLACEMENT SYSTEMS AND METHODS

(71) Applicant: Caisson Interventional LLC, Maple Grove, MN (US)

(72) Inventors: Cyril J. Schweich, Jr., Maple Grove, MN (US); Todd J. Mortier, Maple Grove, MN (US)

(73) Assignee: Caisson Interventional, LLC, Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/267,105

(22) Filed: May 1, 2014

(65) Prior Publication Data

US 2014/0236291 A1   Aug. 21, 2014

Related U.S. Application Data

(63) Continuation of application No. 13/842,206, filed on Mar. 15, 2013.

(60) Provisional application No. 61/635,741, filed on Apr. 19, 2012, provisional application No. 61/669,383, filed on Jul. 9, 2012.

(51) Int. Cl.
*A61F 2/24* (2006.01)

(52) U.S. Cl.
CPC ............. *A61F 2/2409* (2013.01); *A61F 2/243* (2013.01); *A61F 2/2412* (2013.01); *A61F 2/2418* (2013.01); *A61F 2/2445* (2013.01); *A61F 2/24* (2013.01); *A61F 2220/0008* (2013.01); *A61F 2250/006* (2013.01); *A61F 2250/0069* (2013.01)

(58) Field of Classification Search
CPC .. A61F 2/2418; A61F 2/2409; A61F 2/2445; A61F 2/2412; A61F 2/24
USPC ...................... 623/2.1, 2.11, 2.14, 2.17, 2.18
See application file for complete search history.

(56) References Cited

U.S. PATENT DOCUMENTS

| 4,680,031 A | 7/1987 | Alonso |
| 5,423,887 A | 6/1995 | Love et al. |
| 5,662,704 A | 9/1997 | Gross |
| 5,855,601 A | 1/1999 | Bessler et al. |

(Continued)

FOREIGN PATENT DOCUMENTS

| WO | 2007/100410 | 9/2007 |
| WO | WO 2011/119101 | 9/2011 |

(Continued)

OTHER PUBLICATIONS

International Preliminary Report on Patentability and Written Opinion of the International Searching Authority in International Application No. PCT/US2013/036734, dated Oct. 21, 2014, 9 pages.

(Continued)

*Primary Examiner* — Richard Louis
(74) *Attorney, Agent, or Firm* — Fish & Richardson P.C.

(57) ABSTRACT

Systems and methods for medical interventional procedures, including approaches to valve implant. In one aspect, the methods and systems involve a modular approach to treatment.

17 Claims, 43 Drawing Sheets

(56) References Cited

U.S. PATENT DOCUMENTS

| | | |
|---|---|---|
| 5,984,959 A | 11/1999 | Robertson et al. |
| 6,113,631 A | 9/2000 | Jansen |
| 6,296,662 B1 | 10/2001 | Caffey |
| 6,309,417 B1 | 10/2001 | Spence et al. |
| 6,332,893 B1 | 12/2001 | Mortier et al. |
| 6,358,277 B1 | 3/2002 | Duran |
| 6,425,916 B1 | 7/2002 | Garrison et al. |
| 6,530,952 B2 | 3/2003 | Vesely |
| 6,569,196 B1 | 5/2003 | Vesely |
| 6,582,462 B1 | 6/2003 | Andersen et al. |
| 6,629,534 B1 | 10/2003 | St. Goar et al. |
| 6,730,121 B2 | 5/2004 | Ortiz et al. |
| 6,767,362 B2 | 7/2004 | Schreck |
| 6,769,434 B2 | 8/2004 | Liddicoat et al. |
| 6,790,229 B1 | 9/2004 | Berreklouw |
| 6,883,522 B2 | 4/2005 | Spence et al. |
| 6,893,459 B1 | 5/2005 | Macoviak |
| 6,908,481 B2 | 6/2005 | Cribier |
| 6,949,122 B2 | 9/2005 | Adams et al. |
| 7,011,681 B2 | 3/2006 | Vesely |
| 7,018,406 B2 | 3/2006 | Seguin et al. |
| 7,044,966 B2 | 5/2006 | Svanidze et al. |
| 7,101,396 B2 | 9/2006 | Artof et al. |
| 7,147,663 B1 | 12/2006 | Berg et al. |
| 7,160,322 B2 | 1/2007 | Gabbay |
| 7,217,287 B2 | 5/2007 | Wilson et al. |
| 7,252,682 B2 | 8/2007 | Seguin |
| 7,320,704 B2 | 1/2008 | Lashinski et al. |
| 7,329,278 B2 | 2/2008 | Seguin et al. |
| 7,381,218 B2 | 6/2008 | Schreck |
| 7,381,220 B2 | 6/2008 | Macoviak et al. |
| 7,442,204 B2 | 10/2008 | Schwammenthal et al. |
| 7,503,930 B2 | 3/2009 | Sharkawy et al. |
| 7,524,330 B2 | 4/2009 | Berreklouw |
| 7,524,331 B2 | 4/2009 | Birdsall |
| 7,578,843 B2 | 8/2009 | Shu |
| 7,585,321 B2 | 9/2009 | Cribier |
| 7,597,711 B2 | 10/2009 | Drews et al. |
| 7,618,446 B2 | 11/2009 | Andersen et al. |
| 7,625,403 B2 | 12/2009 | Krivoruchko |
| 7,632,308 B2 | 12/2009 | Loulmet |
| 7,708,775 B2 | 5/2010 | Rowe et al. |
| 7,717,955 B2 | 5/2010 | Lane et al. |
| 7,727,276 B2 | 6/2010 | Machiraju |
| 7,748,389 B2 | 7/2010 | Salahieh et al. |
| 7,776,083 B2 | 8/2010 | Vesely |
| 7,780,725 B2 | 8/2010 | Haug et al. |
| 7,785,364 B2 | 8/2010 | Styrc |
| 7,896,915 B2 | 3/2011 | Guyenot et al. |
| 7,914,569 B2 | 3/2011 | Nguyen et al. |
| 7,935,144 B2 | 5/2011 | Robin et al. |
| 7,947,072 B2 | 5/2011 | Yang et al. |
| 7,947,075 B2 | 5/2011 | Goetz et al. |
| 7,959,672 B2 | 6/2011 | Salahieh et al. |
| 7,981,153 B2 | 7/2011 | Fogarty et al. |
| 7,988,725 B2 | 8/2011 | Gross et al. |
| 8,016,882 B2 | 9/2011 | Macoviak et al. |
| 8,025,695 B2 | 9/2011 | Fogarty et al. |
| 8,048,153 B2 | 11/2011 | Salahieh et al. |
| 8,052,749 B2 | 11/2011 | Salahieh et al. |
| 8,055,360 B2 | 11/2011 | Park et al. |
| 8,057,540 B2 | 11/2011 | Letac et al. |
| 8,062,355 B2 | 11/2011 | Figulla et al. |
| 8,092,518 B2 | 1/2012 | Schreck |
| 8,092,521 B2 | 1/2012 | Figulla et al. |
| 8,092,524 B2 | 1/2012 | Nugent et al. |
| 8,123,801 B2 | 2/2012 | Milo |
| 8,133,270 B2 | 3/2012 | Kheradvar et al. |
| 8,142,492 B2 | 3/2012 | Forster et al. |
| 8,157,852 B2 | 4/2012 | Bloom et al. |
| 8,157,853 B2 | 4/2012 | Laske et al. |
| 8,163,011 B2 | 4/2012 | Rankin |
| 8,172,898 B2 | 5/2012 | Alferness et al. |
| 8,182,528 B2 | 5/2012 | Salahieh et al. |
| 8,182,530 B2 | 5/2012 | Huber |
| 8,206,437 B2 | 6/2012 | Bonhoeffer et al. |
| 8,231,670 B2 | 7/2012 | Salahieh et al. |
| 8,236,049 B2 | 8/2012 | Rowe et al. |
| 8,246,677 B2 | 8/2012 | Ryan |
| 8,252,051 B2 | 8/2012 | Chau et al. |
| 8,262,724 B2 | 9/2012 | Seguin et al. |
| 8,273,120 B2 | 9/2012 | Dolan |
| 8,277,502 B2 | 10/2012 | Miller et al. |
| 8,282,051 B2 | 10/2012 | Nutaro et al. |
| 8,287,591 B2 | 10/2012 | Keidar et al. |
| 8,292,938 B2 | 10/2012 | Case |
| 8,308,796 B2 | 11/2012 | Lashinski et al. |
| 8,308,798 B2 | 11/2012 | Pintor et al. |
| 8,317,858 B2 | 11/2012 | Straubinger et al. |
| 8,323,332 B2 | 12/2012 | Agnew |
| 8,323,335 B2 | 12/2012 | Rowe et al. |
| 8,348,998 B2 | 1/2013 | Pintor et al. |
| 8,403,983 B2 | 3/2013 | Quadri et al. |
| 8,449,599 B2 * | 5/2013 | Chau et al. .................. 623/1.26 |
| 8,454,686 B2 | 6/2013 | Alkhatib |
| 8,460,366 B2 | 6/2013 | Rowe |
| 8,500,798 B2 | 8/2013 | Rowe et al. |
| 8,512,398 B2 | 8/2013 | Alkhatib |
| 8,568,477 B2 | 10/2013 | Lashinski et al. |
| 8,579,964 B2 | 11/2013 | Lane et al. |
| 8,585,755 B2 | 11/2013 | Chau et al. |
| 8,623,080 B2 | 1/2014 | Fogarty et al. |
| 8,628,569 B2 | 1/2014 | Benichou et al. |
| 8,628,571 B1 | 1/2014 | Hacohen et al. |
| 8,641,757 B2 | 2/2014 | Pintor et al. |
| 8,652,203 B2 | 2/2014 | Quadri et al. |
| 8,657,872 B2 | 2/2014 | Seguin |
| 8,685,085 B2 | 4/2014 | Guyenot et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,795,355 B2 | 8/2014 | Alkhatib |
| 8,795,356 B2 | 8/2014 | Quadri et al. |
| 8,834,564 B2 | 9/2014 | Tuval et al. |
| 8,840,662 B2 | 9/2014 | Salahieh et al. |
| 8,840,663 B2 | 9/2014 | Salahieh et al. |
| 8,852,272 B2 | 10/2014 | Gross et al. |
| 8,858,620 B2 | 10/2014 | Salahieh et al. |
| 8,870,948 B1 | 10/2014 | Erzberger et al. |
| 8,870,949 B2 | 10/2014 | Rowe |
| 8,876,895 B2 | 11/2014 | Tuval et al. |
| 8,894,702 B2 | 11/2014 | Quadri et al. |
| 8,911,493 B2 | 12/2014 | Rowe et al. |
| 8,926,690 B2 | 1/2015 | Kovalsky |
| 8,926,691 B2 | 1/2015 | Chau et al. |
| 8,932,358 B1 | 1/2015 | Nehls |
| 8,961,595 B2 | 2/2015 | Alkhatib |
| 8,968,395 B2 | 3/2015 | Hauser et al. |
| 8,986,370 B2 | 3/2015 | Southerland et al. |
| 8,986,373 B2 | 3/2015 | Chau et al. |
| 9,005,277 B2 | 4/2015 | Pintor et al. |
| 9,005,278 B2 | 4/2015 | Pintor et al. |
| 9,017,399 B2 | 4/2015 | Gross et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,050,188 B2 | 6/2015 | Schweich et al. |
| 9,066,801 B2 | 6/2015 | Kovalsky et al. |
| 9,072,604 B1 | 7/2015 | Melnick et al. |
| 9,084,676 B2 | 7/2015 | Chau et al. |
| 9,155,617 B2 | 10/2015 | Carpentier et al. |
| 9,168,133 B2 | 10/2015 | Spenser et al. |
| 9,173,738 B2 | 11/2015 | Murray, III et al. |
| 9,192,466 B2 | 11/2015 | Kovalsky et al. |
| 9,226,826 B2 | 1/2016 | Rust |
| 9,241,792 B2 | 1/2016 | Benichou et al. |
| 9,259,315 B2 | 2/2016 | Zhou et al. |
| 9,289,293 B2 | 3/2016 | Murad et al. |
| 9,295,547 B2 | 3/2016 | Costello et al. |
| 9,295,548 B2 | 3/2016 | Drews et al. |
| 9,295,550 B2 | 3/2016 | Nguyen et al. |
| 9,301,843 B2 | 4/2016 | Richardson et al. |

(56) References Cited

U.S. PATENT DOCUMENTS

| | | | |
|---|---|---|---|
| 9,301,863 B2 | 4/2016 | Punga et al. | |
| 2001/0007956 A1 | 7/2001 | Letac et al. | |
| 2001/0021872 A1 | 9/2001 | Bailey et al. | |
| 2002/0151970 A1* | 10/2002 | Garrison et al. | 623/2.11 |
| 2003/0055492 A1* | 3/2003 | Shaolian | A61F 2/2418 623/1.24 |
| 2003/0130726 A1* | 7/2003 | Thorpe et al. | 623/1.24 |
| 2004/0127982 A1* | 7/2004 | Machold | A61F 2/2418 623/2.36 |
| 2004/0260393 A1* | 12/2004 | Rahdert | A61B 17/00234 623/2.36 |
| 2005/0010287 A1* | 1/2005 | Macoviak | A61F 2/2445 623/2.36 |
| 2005/0137689 A1 | 6/2005 | Salahieh et al. | |
| 2005/0137690 A1 | 6/2005 | Salahieh et al. | |
| 2005/0165479 A1 | 7/2005 | Drews et al. | |
| 2007/0027533 A1 | 2/2007 | Douk | |
| 2008/0004697 A1 | 1/2008 | Lichtenstein et al. | |
| 2008/0015671 A1 | 1/2008 | Bonhoeffer | |
| 2008/0086164 A1 | 4/2008 | Rowe | |
| 2008/0103586 A1 | 5/2008 | Styrc et al. | |
| 2008/0140189 A1 | 6/2008 | Nguyen et al. | |
| 2008/0221672 A1 | 9/2008 | Lamphere et al. | |
| 2009/0005863 A1 | 1/2009 | Goetz et al. | |
| 2009/0088836 A1* | 4/2009 | Bishop | A61F 2/2418 623/2.1 |
| 2010/0049315 A1* | 2/2010 | Kirson | 623/2.37 |
| 2010/0100173 A1 | 4/2010 | Lafontaine | |
| 2010/0145440 A1* | 6/2010 | Keranen | A61F 2/2445 623/2.37 |
| 2010/0217382 A1 | 8/2010 | Chau et al. | |
| 2010/0262232 A1 | 10/2010 | Annest | |
| 2010/0280606 A1 | 11/2010 | Naor | |
| 2010/0312333 A1* | 12/2010 | Navia et al. | 623/2.36 |
| 2011/0004296 A1 | 1/2011 | Lutter et al. | |
| 2011/0022168 A1 | 1/2011 | Cartledge | |
| 2011/0137397 A1 | 6/2011 | Chau et al. | |
| 2011/0137410 A1 | 6/2011 | Hacohen | |
| 2011/0166636 A1 | 7/2011 | Rowe | |
| 2011/0208293 A1 | 8/2011 | Tabor | |
| 2011/0218619 A1 | 9/2011 | Benichou et al. | |
| 2011/0224785 A1 | 9/2011 | Hacohen | |
| 2011/0245911 A1 | 10/2011 | Quill et al. | |
| 2011/0257721 A1 | 10/2011 | Tabor | |
| 2011/0282438 A1 | 11/2011 | Drews et al. | |
| 2011/0295363 A1 | 12/2011 | Girard et al. | |
| 2011/0301702 A1 | 12/2011 | Rust et al. | |
| 2011/0319988 A1 | 12/2011 | Schankereli et al. | |
| 2011/0319989 A1 | 12/2011 | Lane et al. | |
| 2012/0010697 A1 | 1/2012 | Shin et al. | |
| 2012/0016464 A1* | 1/2012 | Seguin | 623/1.26 |
| 2012/0035722 A1 | 2/2012 | Tuval | |
| 2012/0053675 A1 | 3/2012 | Borock | |
| 2012/0059458 A1* | 3/2012 | Buchbinder et al. | 623/2.36 |
| 2012/0101571 A1 | 4/2012 | Thambar et al. | |
| 2012/0136430 A1 | 5/2012 | Sochman et al. | |
| 2012/0165930 A1* | 6/2012 | Gifford, III | A61F 2/2418 623/2.36 |
| 2012/0310328 A1 | 12/2012 | Olson et al. | |
| 2013/0172992 A1 | 7/2013 | Gross et al. | |
| 2013/0184811 A1 | 7/2013 | Rowe et al. | |
| 2013/0211508 A1 | 8/2013 | Lane et al. | |
| 2013/0282110 A1 | 10/2013 | Schweich et al. | |
| 2013/0282114 A1 | 10/2013 | Schweich et al. | |
| 2013/0304200 A1 | 11/2013 | McLean et al. | |
| 2014/0005778 A1 | 1/2014 | Buchbinder et al. | |
| 2014/0012372 A1 | 1/2014 | Chau et al. | |
| 2014/0012373 A1 | 1/2014 | Chau et al. | |
| 2014/0039611 A1 | 2/2014 | Lane et al. | |
| 2014/0052237 A1 | 2/2014 | Lane et al. | |
| 2014/0214156 A1 | 7/2014 | Navia et al. | |
| 2014/0222136 A1 | 8/2014 | Geist et al. | |
| 2014/0257467 A1 | 9/2014 | Lane et al. | |
| 2014/0343669 A1 | 11/2014 | Lane et al. | |
| 2014/0358223 A1 | 12/2014 | Rafiee et al. | |
| 2015/0039083 A1 | 2/2015 | Rafiee | |
| 2015/0094802 A1 | 4/2015 | Buchbinder et al. | |
| 2015/0112433 A1 | 4/2015 | Schweich et al. | |
| 2015/0127096 A1 | 5/2015 | Rowe et al. | |
| 2015/0150678 A1 | 6/2015 | Brecker | |
| 2015/0157458 A1 | 6/2015 | Thambar et al. | |
| 2015/0173897 A1 | 6/2015 | Raanani et al. | |
| 2015/0196390 A1 | 7/2015 | Ma et al. | |
| 2015/0216657 A1 | 8/2015 | Braido | |
| 2015/0238312 A1 | 8/2015 | Lashinski | |
| 2015/0238313 A1 | 8/2015 | Spence et al. | |
| 2015/0265402 A1 | 9/2015 | Centola et al. | |
| 2015/0320553 A1 | 11/2015 | Chau et al. | |
| 2015/0327995 A1 | 11/2015 | Morin et al. | |
| 2015/0327996 A1 | 11/2015 | Fahim et al. | |
| 2015/0327999 A1 | 11/2015 | Board et al. | |
| 2015/0335421 A1 | 11/2015 | Figulla et al. | |
| 2015/0342733 A1 | 12/2015 | Alkhatib et al. | |
| 2015/0351906 A1 | 12/2015 | Hammer et al. | |
| 2016/0000564 A1 | 1/2016 | Buchbinder et al. | |
| 2016/0008131 A1 | 1/2016 | Christianson et al. | |
| 2016/0022417 A1 | 1/2016 | Karapetian et al. | |
| 2016/0045307 A1 | 2/2016 | Yohanan et al. | |
| 2016/0045309 A1 | 2/2016 | Valdez et al. | |
| 2016/0051362 A1 | 2/2016 | Cooper et al. | |
| 2016/0074160 A1 | 3/2016 | Christianson et al. | |

FOREIGN PATENT DOCUMENTS

| | | |
|---|---|---|
| WO | WO 2012/103204 | 8/2012 |
| WO | 2013/114214 | 8/2013 |

OTHER PUBLICATIONS

U.S. Appl. No. 61/287,099, filed Dec. 4, 2009, Chau et al.
U.S. Appl. No. 61/266,774, filed Dec. 16, 2009, Chau et al.
International Search Report in Application No. PCT/US2013/036728, dated Aug. 8, 2013, 3 pages.
International Search Report in Application No. PCT/US2013/036734, dated Aug. 20, 2013, 4 pages.
International Search Report and Written Opinion in International Application No. PCT/US2014/061788, dated Jan. 28, 2015, 17 pages.
Supplementary European Search Report in Eurpoean Application No. 13778768, dated Jan. 12, 2016, 7 pages.
International Search Report and Written Opinion in International Application No. PCT/US2015/056935, dated Feb. 12, 2016, 14 pages.
Extended European Search Report in European Application No. 13778799.0, dated Dec. 21, 2015, 8 pages.

* cited by examiner

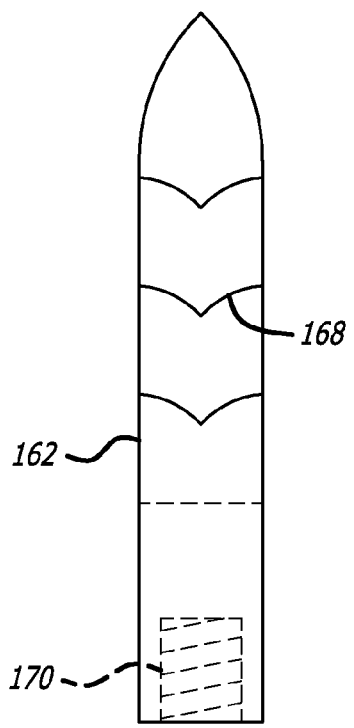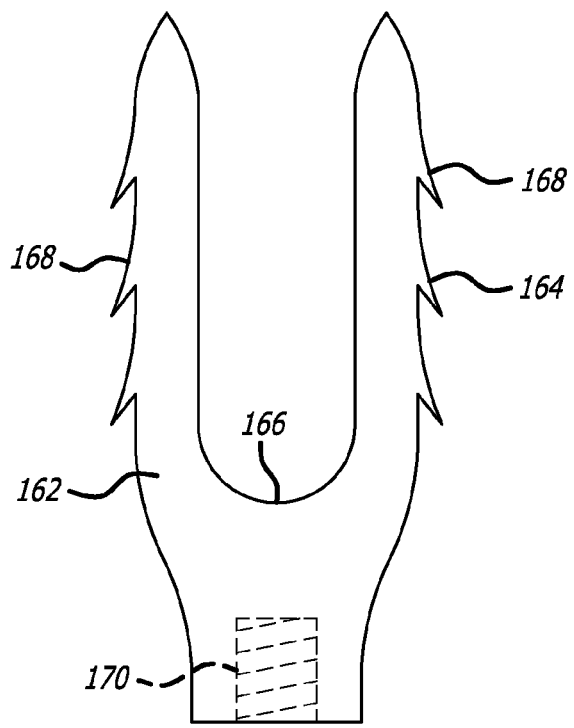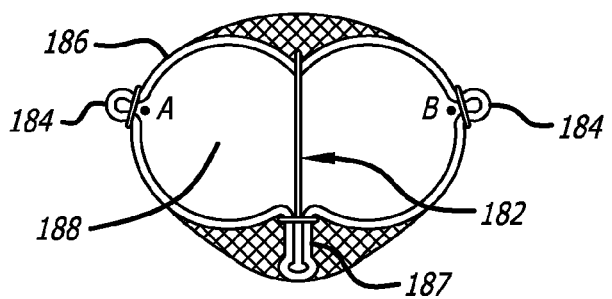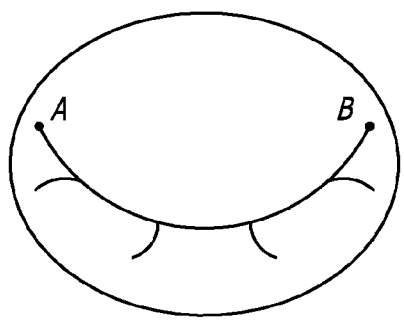
FIG. 20　　　FIG. 21
FIG. 22

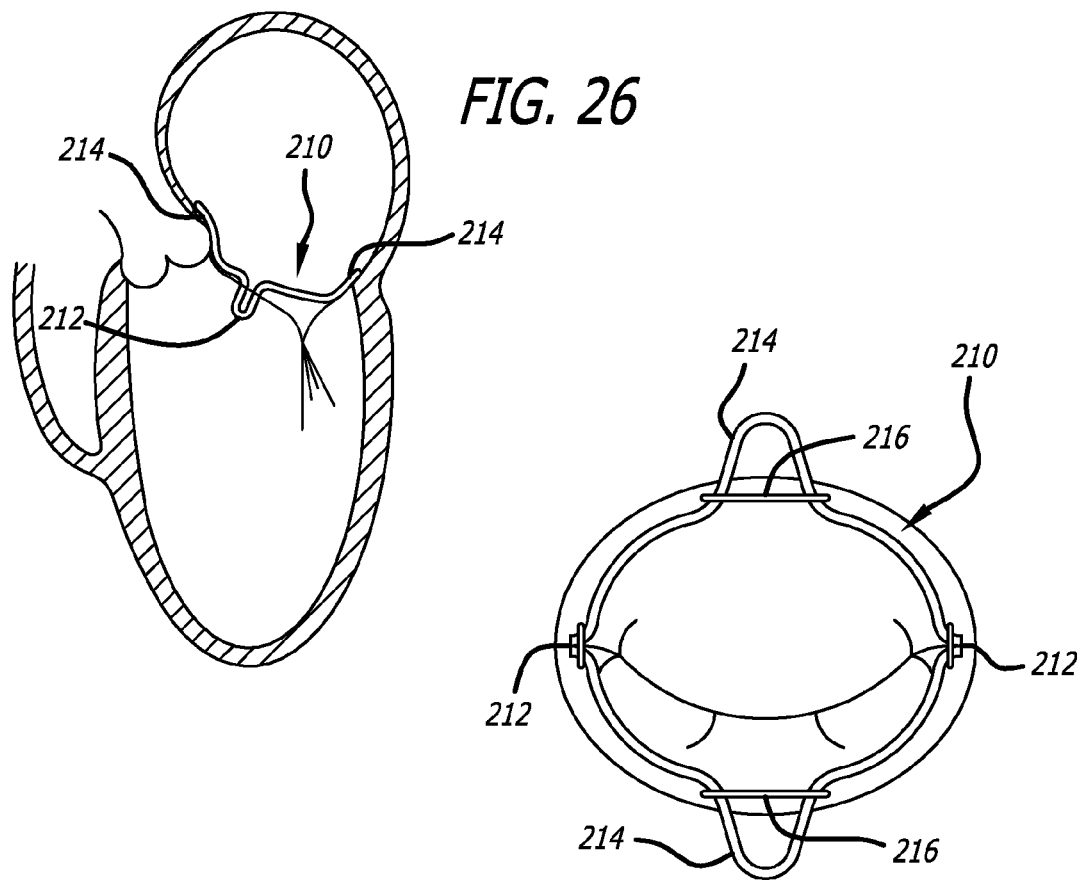
FIG. 26
FIG. 27
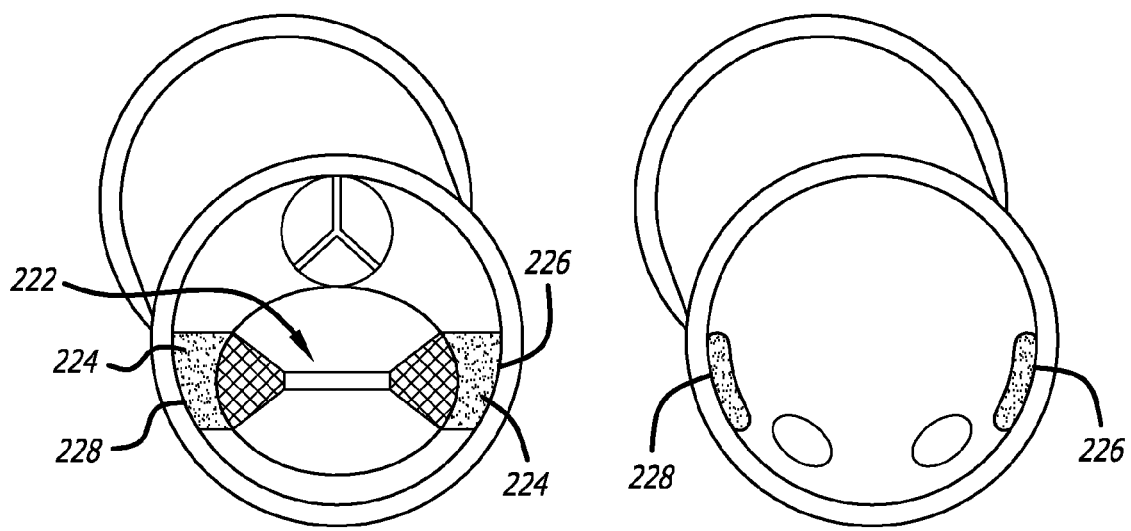
FIG. 28
FIG. 29

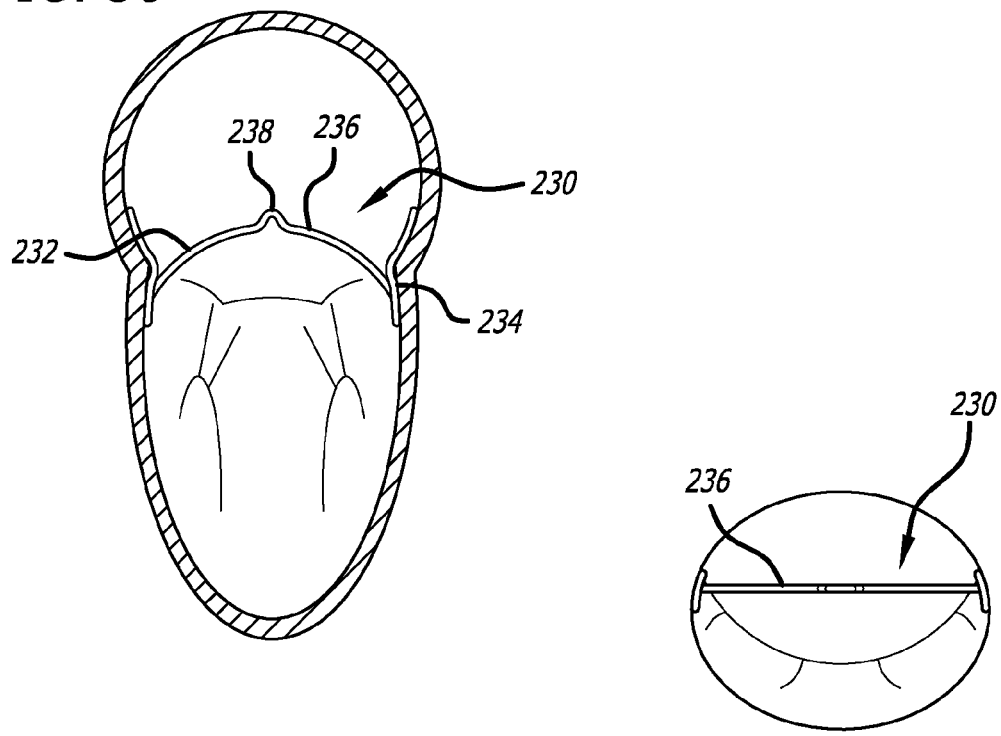
FIG. 30
FIG. 31
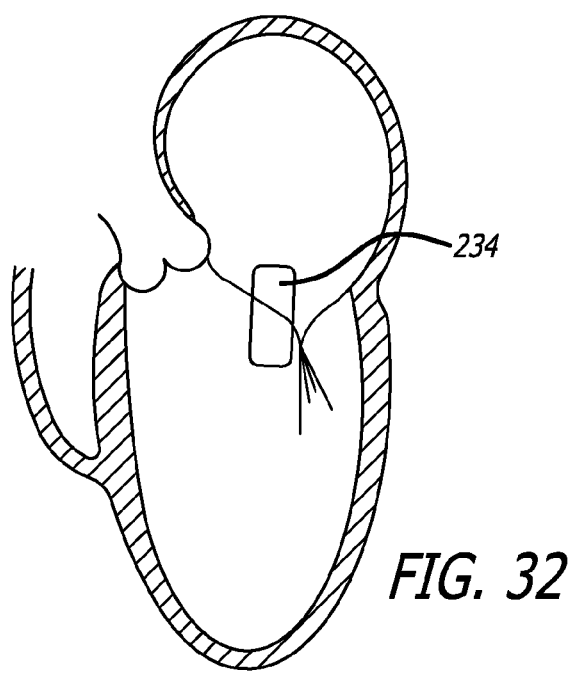
FIG. 32

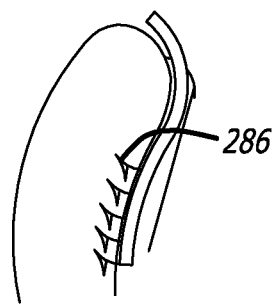
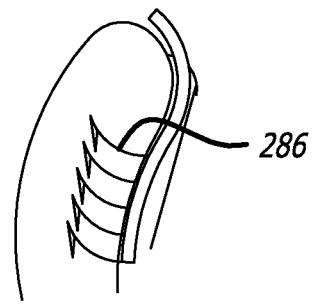
FIG. 45C  FIG. 45D
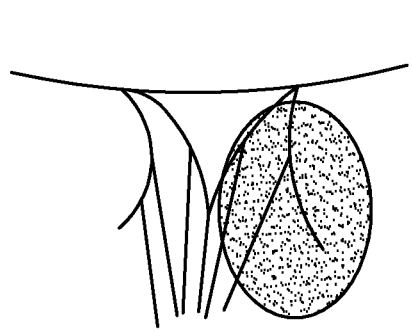
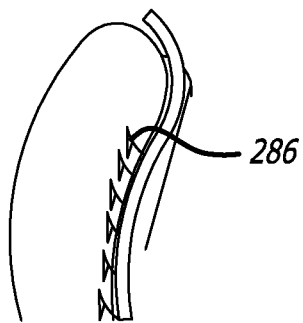
FIG. 45E  FIG. 45F

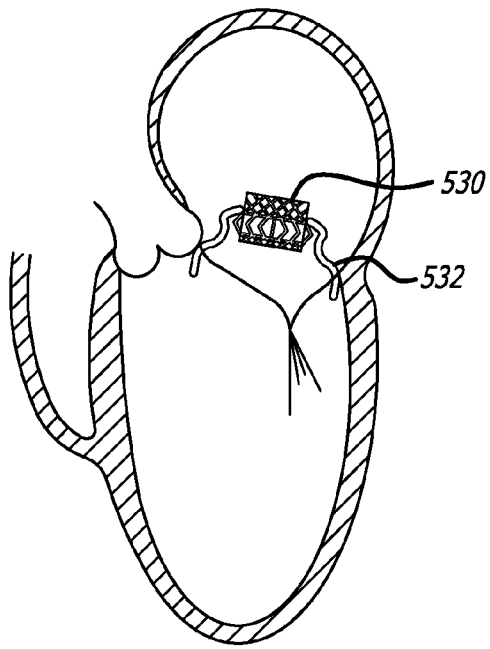
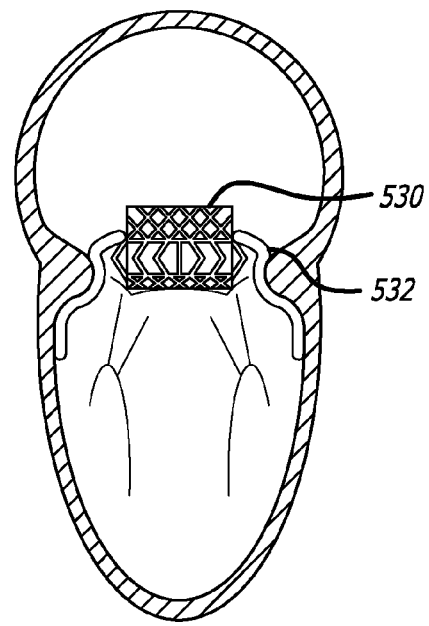
FIG. 88    FIG. 89
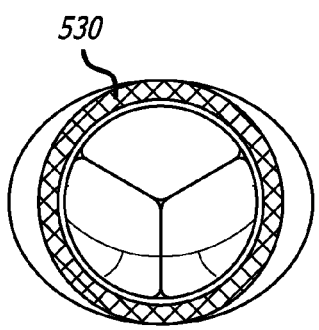
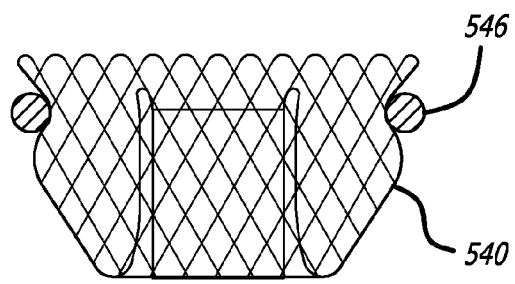
FIG. 90    FIG. 91
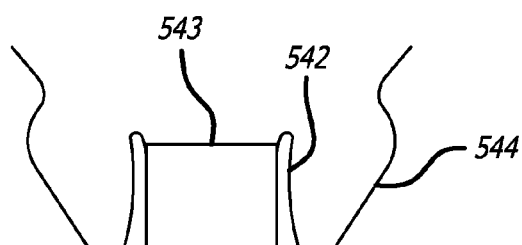
FIG. 92

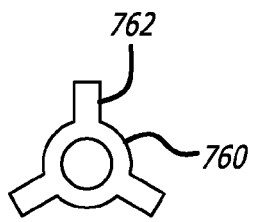
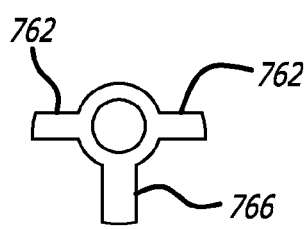
FIG. 128  FIG. 129
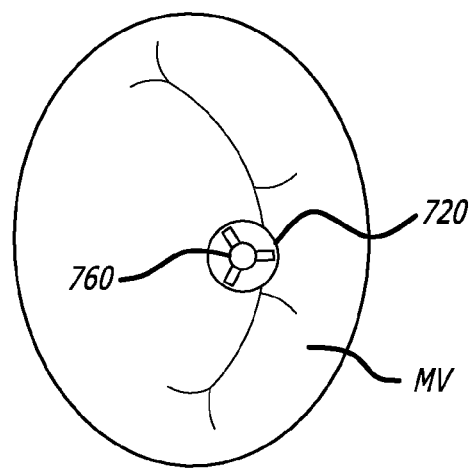
FIG. 131
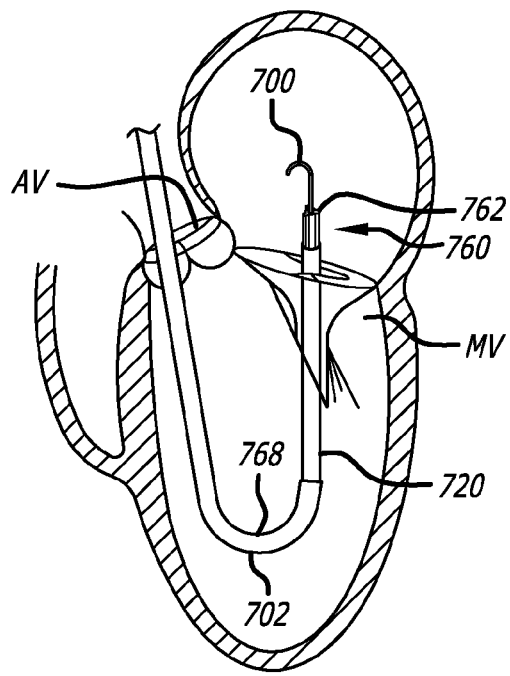
FIG. 130
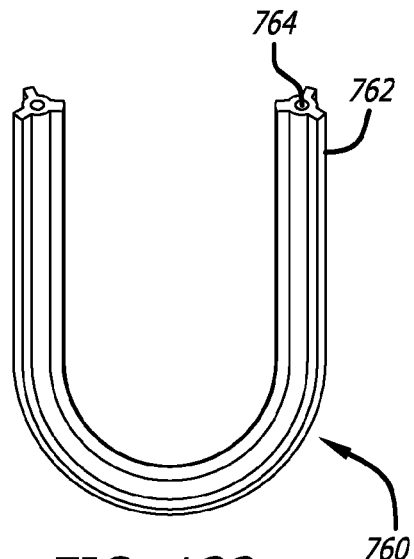
FIG. 132

VALVE REPLACEMENT SYSTEMS AND METHODS

CROSS-REFERENCES TO RELATED APPLICATIONS

This application is a continuation of U.S. application Ser. No. 13/842,206, filed Mar. 15, 2013 and claims the benefit of U.S. Application Ser. No. 61/635,741, filed Apr. 19, 2012 and U.S. Application Ser. No. 61/669,383, filed Jul. 9, 2012, the entire disclosures of which are expressly incorporated herein.

BACKGROUND OF THE DISCLOSURE

The present disclosure relates to medical interventional systems and methods and more particularly, to valve replacement systems and methods. The long-term clinical effect of valve regurgitation is well recognized as a significant contributor to cardiovascular related morbidity and mortality. In particular, there are two basic classifications of mitral regurgitation ("MR"), primary and secondary. Primary MR results when there is either direct tissue pathology of the valve structures or there is structural damage/alteration of one or more valve structures (leaflets, chordae). Secondary MR results from damage to the myocardium and left ventricle resulting in left ventricular dilatation, and secondary alteration of mitral valve geometry and functional loss of valve competence. Whether valvular in origin leading to a ventricular problem or of ventricular/muscle origin leading to the valvular problem, the effect of high levels of MR is significant on cardiopulmonary physiology, resulting in significantly elevated left atrial pressures and pulmonary pressures, pulmonary congestion, and volume and energy overload effects on the myocardium. This physiology creates significant heart failure symptoms of shortness of breath and decreased physical endurance, ultimately leading to death.

The decision to intervene on a regurgitant mitral valve relates to the level of mitral regurgitation, the symptoms of the patient as an indicator of progressive negative physiologic effect, and the functional status of the left ventricle, specifically ejection fraction. The risk of intervention is weighed against the benefit of MR treatment.

The mitral valve is a therapeutic target of intervention/surgery early in the disease process of primary valvular disease because of MR's deleterious effects on heart/ventricular function if left untreated. For patients with moderate-severe or severe levels of MR combined with even a modest decrease in ejection fraction ("EF"), or the development of symptoms, surgical correction is indicated. In this situation, the risk of surgery in what is an otherwise healthy patient is far outweighed by the beneficial effects of eliminating the long-term negative effects of MR.

A more difficult question has been the patient with secondary or functional mitral regurgitation. In this situation, the patient has pre-existing LV dysfunction combined with heart failure symptoms, and a developing/worsening level of MR. The risks of intervention in this scenario are much greater. The net benefit of surgically intervening to eliminate the MR has not been demonstrated. Symptomatic benefit has been seen, but not a net mortality benefit. Therefore, it is usually contemplated or applied concomitantly when a patient is undergoing coronary artery bypass graft CABG revascularization.

The classification of mitral regurgitation as primary or secondary is a useful to differentiate between the underlying disease processes that led to the incompetent valve. These provide a starting point that can direct the type and timing of an intervention. However, classification is not sufficient to fully describe the issues that direct a therapeutic approach. Because the mitral valve is complex structurally, mechanically, and physiologically, a more detailed description and understanding of the abnormalities associated with mitral regurgitation is needed to direct existing therapies, as well as develop new options for therapy.

Pathologic abnormality of the mitral valve tissue is a common cause of primary mitral regurgitation. Typical pathologies that occur include rheumatic, myxomatous, endocarditis, and Marfan's or other collagen based tissue diseases. Calcification and leaflet thickening are also abnormalities associated with direct tissue level changes in the valve. These can be either part of a primary tissue based disease or result from a long-standing insult to the valve, including regurgitant jetting across the leaflets.

Congenital and acquired structural abnormalities like ruptured chordae, leaflet prolapse, fenestrations, and clefts can also be forms of primary valve disease leading to mitral regurgitation.

Functional MR results from myocardial damage leading to ventricular functional loss and geometric changes that impact the valve coaptation through associated annular dilatation and papillary muscle displacement. In pure functional MR, the valve structures are not pathologic nor have structural defects, but the geometric alteration leads to a loss of coaptation of the mitral valve leaflets, often in the central A2/P2 segment of the valve.

As with many multi-factorial clinical problems, one etiologic element (tissue pathology, structural alterations, functional/geometric changes) may lead to others resulting in a "mixed" picture. This is especially true with mitral regurgitation. In the case of primary MR of either tissue or structural origin, volume overload of the LV can create failure and LV dilatation creating a component of functional MR if the valve is left untreated. In the case of long standing functional MR, tissue changes can be seen such as calcification and thickening caused by the regurgitant jet and high leaflet stresses. Muscle/tissue damage to the myocardium in and around the sub-valvular apparatus can create structural alteration such as ruptured papillary muscles/chordae and prolapse. Excessive tenting of the leaflets associated with significant functional MR can also stress the chords causing rupture.

The net result is that MR is a spectrum disorder with many patients having a mixed picture of valve abnormalities. This is an important factor in the decisions surrounding a mitral valve therapeutic approach, specifically repair or replacement.

The primary goal of any therapy of the mitral valve is to significantly reduce or eliminate the regurgitation. By eliminating the regurgitation, the destructive volume overload effects on the left ventricle are attenuated. The volume overload of regurgitation relates to the excessive kinetic energy required during isotonic contraction to generate overall stroke volume in an attempt to maintain forward stroke volume and cardiac output. It also relates to the pressure potential energy dissipation of the leaking valve during the most energy-consuming portion of the cardiac cycle, isovolumic contraction. Additionally, successful MR reduction should have the effect of reducing the elevated pressures in the left atrium and pulmonary vasculature reducing pulmonary edema (congestion) and shortness of breath symptomatology. It also has a positive effect on the filling profile of the left ventricle and the restrictive LV physiology that can result with MR. These pathophysiologic issues indicate the potential benefits of MR therapy, but also indicates the complexity of the system and the need for a therapy to focus beyond the MR level or grade.

It is also desirable to prevent new deleterious physiology or function of the valve. The procedure and system used to fix the mitral valve ideally should avoid worsening other (non-MR) existing pathologic conditions or creating new pathologic conditions as a result of the treatment of the critical factors to be managed is Stenosis/gradient. That is, if a valve system is used that does not allow for sufficient LV inflow without elevated filling pressures, then critical benefits of MR reduction are dissipated or lost. Moreover, atrial fibrillation is to be avoided as it can result if elevated pressures are not relieved by the therapy, or are created by the system (high pressure results in atrial stress leading to dilatation ultimately leading to arrhythmias). Also, if the procedure results in damage to atrial tissue at surgery, it can result in the negative physiologic effect of atrial fibrillation. Further, one should be aware of the possibility of increased LV Wall Stress (LV geometry). Due to the integral relationship of the mitral valve with LV geometry through the papillary and chordal apparatus, LV wall stress levels can be directly affected resulting in alterations of LV filling and contraction mechanics. Accordingly, a system that does not preserve or worsens the geometry of the LV can counter the benefits of MR reduction because of the alteration of contractile physiology.

It has been generally agreed that it is preferable if the valve can be repaired. Repair of valve elements that target the regurgitant jet only allows for minimal alteration to the valve elements/structures that are properly functioning allowing for the least potential for negatively effecting the overall physiology while achieving the primary goal. Native valve preservation can be beneficial because a well repaired valve is considered to have a better chance of having long standing durability versus a replacement with an artificial valve that has durability limits. Also, while current surgical artificial valves attempt chord sparing procedures, the LV geometric relationship may be negatively altered if not performed or performed poorly leading to an increase in LV wall stress due to an increase in LV diameter. Thus, while preferred and possible for technically competent surgeons, the relatively high recurrence rate of MR due to inadequate repair, the invasiveness of the surgery especially in sick or functional MR patients, and the complexities of a repair for many surgeons lead to a high percentage of mitral operations being replacement.

Conventionally, surgical repair or replacement of the mitral valve is performed on cardiopulmonary bypass and is usually performed via an open median sternotomy resulting in one of the most invasive high risk cardiac surgical operations performed, especially in subpopulations such as functional MR. Therefore, a key improvement to mitral valve operations is to significantly lower the risk and invasiveness, specifically utilizing a percutaneous or minimally invasive technique.

While there have been attempts to replicate existing surgical repair via less invasive surgical or percutaneous methods, given the complexity of repairing the valve surgically, the efforts have largely been deemed lacking in achieving adequate efficacy and have not altered the risk benefit ratio sufficiently to warrant ongoing investment, approval, or adoption. In particular, there has been a general technology failure due to the complexity of anatomy to percutaneously manage with an implant or implantable procedure. The broad spectrum of mitral disease directly influences outcomes with a resulting inability to match technology with pathology. There has also been observed inadequate efficacy with poor surgical replication and safety results. It has also been recognized that percutaneous approaches successful to certain valve procedures, such as aortic valve replacement associated with a single pathology and a relatively circular rigid substrate, mitral valves often suffer from multiple pathologies and a flexible or elastic annular with multiple structures.

Accordingly, what is needed is an effective long lasting MR reduction without creating negative physiologic consequences to the cardio-pulmonary system (heart, lungs, peripheral vasculature) including stenosis, LV wall stress and atrial fibrillation. It is also desirable to be able to perform the operation in a reliable, repeatable, and easy to perform procedure and to have a broadly applicable procedure for both patients and physicians, while employing a significantly less invasive method.

The present disclosure addresses these and other needs.

SUMMARY

Briefly and in general terms, the present disclosure is directed towards valve replacement and repair systems and methods. In one particular aspect, the present disclosure describes a percutaneous or minimally invasive mitral valve replacement system that eliminates MR, provides adequate physiologic inflow, and preserves and/or improves LV geometry in a reliable, repeatable, and easy to perform procedure.

In one aspect, there is provided a mitral valve replacement system including an anchoring structure and an artificial valve configured to treat a native heart. In another aspect, there is provided a method of replacing a valve including providing anchor structure, advancing a valve delivery catheter into a heart, advancing an artificial valve out of the delivery catheter and into the heart, and positioning the artificial valve to treat a native heart.

In one approach, the mitral valve replacement system addresses a number of basic functional requirements. One requirement is the valve function itself, the occlusion of flow during systole, and open to flow during diastole. Another requirement is the seal between the artificial replacement valve frame/structure and the tissue to prevent/minimize any peri-valvular leaks or flow. A further requirement is the anchoring or securement function to hold the functioning valve in position and withstand the substantial and variable cyclical load placed on the valve during systolic pressurization of the valve surface. It is intended that each of these is met in the durable, therapeutically, and physiologically appropriate mitral valve replacement system disclosed herein.

The presently disclosed system may utilize a staged approach to the functional elements of the system, starting with the anchoring or securement functional element. Additionally, the staging can be performed within a single procedure or in multiple, time separated procedures. By staging and separating functional elements, the individual elements will be simpler in design and simpler to deploy and implant. This staging of the anchor implantation of the present invention provides a stable, reliable, consistent, substrate to deliver a replacement valve into the mitral position.

A mitral valve replacement system according to the present disclosure includes an anchor element, a sealing element, and a valve element, and utilizes an anchor delivery system, and a valve delivery system. More than one element may be incorporated into a structure, for example, an anchor element also may comprise a sealing structure, or a valve element may comprise a sealing structure. In accordance with the present teachings, the elements of the valve replacement system may be implanted in staged procedures, for example, an anchor element may be implanted during a first procedure and a valve element may be implanted during a second procedure. As disclosed herein, the processes, systems used for implantation, and timing of implantation may vary. The present disclosure further contemplates that the anchor element (and in some cases sealing element) of the disclosed mitral valve replacement system may be used with existing valve technologies, as discussed further below. Similarly, delivery systems may include those disclosed herein, but the present disclosure also contemplates that existing delivery systems may be used to deliver prior art valve structures.

Thus, in various approaches, a stable, reliable, consistent substrate is created by implanting an anchor structure to secure a valve without disruption of native valve function until an artificial valve is operational. Further, an anchor structure that predictably accepts an artificial valve and will seal the tissue and an implant interface is provided as is an anchor delivery system that can accurately, simply, and reliably deliver anchor substrate structure while maintaining native valve function. In one particular aspect, a supraannular ring with commissural anchors is provided, two commissural anchors sized and shaped to correspond to valve commissures and a third anchor for placement at a second anchor location. Anchor delivery can involve individual, releasable control elements such that in situ access to each anchoring location is provided in order to deploy tissue penetrating structures for securement. Catheter/tube access is contemplated as is over-the-wire access.

It is also contemplated that current valve technologies can be leveraged. A valve to anchor interface can involve a geometric interlock, to thereby allow the flexibility for adaptation to a broad spectrum of valve technology. In this regard, a valve to native valve interface preserves subvalvular structure relationships.

Moreover, the valve anchor approach can fundamentally alter the complexity of performing a completely percutaneous mitral replacement by creating a reliable and consistent substrate. Thus, it is intended that the implant design exploit the geometry/mechanics of the commissures to create sufficient holding capability. Further, design and delivery approaches that maintain native valve function providing the ability to completely separate and stage the implantation of the system functional components is contemplated as are delivery methods that have potential for quick fluoroscopic delivery, positioning, and deployment. Consequently, there is an optimal valve performance opportunity due to maximal design flexibility and technology leveraging, and a delivery capability to achieve precise positioning prior to valve deployment. The same creates desired tissue/implant sealing and maintains sub-valvular structural relationships.

Accordingly, employing the present system and method facilitates effective long lasting MR reduction without creating negative physiologic consequences to the cardio-pulmonary system (heart, lungs, peripheral vasculature) including stenosis, LV wall stress, and atrial fibrillation. The method can involve performance of the operation in a reliable, repeatable, and easy to perform procedure and is a broadly applicable procedure for both patients and physicians. A significantly less invasive method results, one which can be fully percutaneous from the start.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIG. 20 is a front view, depicting an alternative approach to a penetrating structure;

FIG. 21 is a side view, depicting structure of FIG. 20;

FIG. 22 is a transverse view, depicting another anchor wire frame structure;

FIG. 26 is a cross-sectional view, depicting still yet another anchor wire frame;

FIG. 27 is a transverse view, depicting the anchor wire frame of FIG. 26

FIG. 28 is a transverse view at the level of the mitral annulus, depicting an anchor structure that has a interconnecting cross member;

FIG. 29 is a transverse view, depicting the anchor of FIG. 28;

FIG. 30 is a vertical cross-section of the heart looking at the posterior wall of LV, depicting an exemplary anchor wire frame;

FIG. 31 is a view from above the annulus, depicting the anchor frame of FIG. 30.

FIG. 32 is a vertical cross section through the aorta and the A2/P2 segment of the mitral valve, showing the anchor frame of FIGS. 30 and 31.

FIG. 45C depicts the anchor structure and illustrates shear loading of the anchor/tissue interface;

FIGS. 45D-45F depict various anchor configurations that abut the LV wall;

FIG. 88 is a vertical cross section through the aorta and the A2/P2 segment of the mitral valve, depicting yet another embodiment of a sealing structure;

FIG. 89 is a vertical section view of the structure of FIG. 88;

FIG. 90 is a top view of the structure of FIGS. 87 and 88;

FIG. 91 is a side view, depicting an anchor/valve interface structure;

FIG. 92 is a cross section of the structure in FIG. 91;

FIG. 113 is a sectional view, depicting sealing structure for the artificial valve frame to native leaflets;

FIG. 114 is a sectional view, depicting wire structure that can be used to secure the leaflets;

FIG. 115 is a sectional view, depicting the structure of 114;

FIG. 116 is side view, depicting a guidewire placed in the LV;

FIG. 117 shows the placement an intraventricular guide catheter used for the anchor delivery and orientation of the tip toward the mitral orifice;

FIGS. 118 and 119 show the placement of a guidewire across the mitral orifice in a long axis and short axis heart views, respectively;

FIG. 120 shows the retraction of an expanded wire cage structure back through the mitral orifice;

FIG. 121 shows a transverse cross section, depicting the cage;

FIGS. 122 and 123 show long axis and short axis views, depicting the advancement of an anchor delivery catheter over the previously tracked wire;

FIG. 124 shows the advancement and unfolding of an anchor in the left atria;

FIG. 125 is a transverse short axis view, depicting the unfolded anchor, delivery wires and connections to frame, and the delivery catheter of FIG. 124;

FIG. 126 is a vertical long axis view, depicting the anchor in position after the delivery catheter has been pulled beneath the valve;

Figure 126:
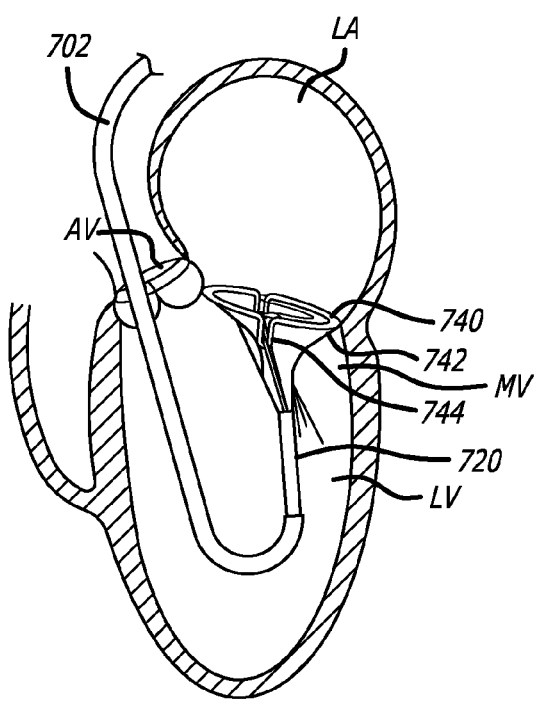
Figure 127:
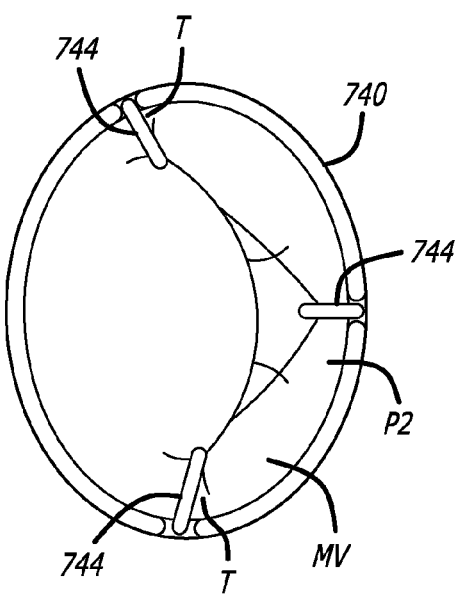
Figure 133:
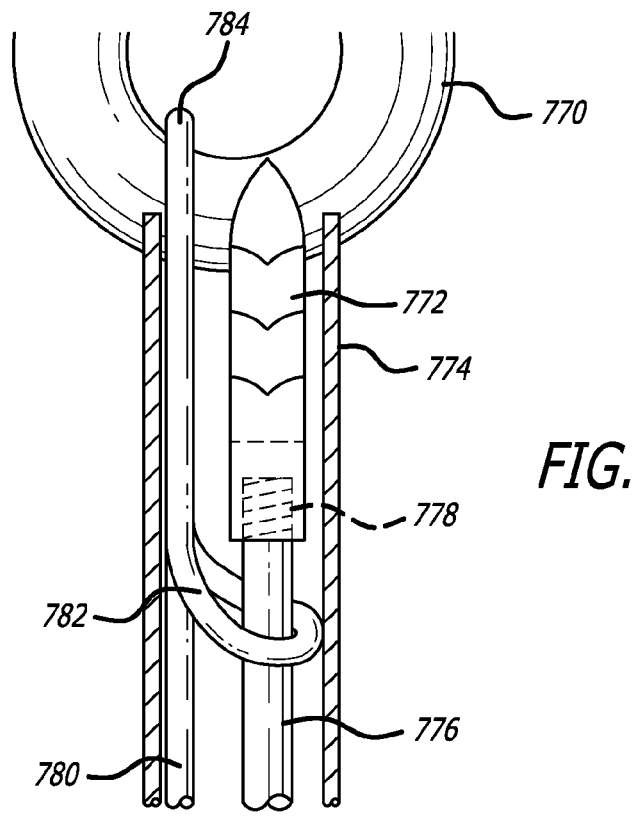
Figure 134:
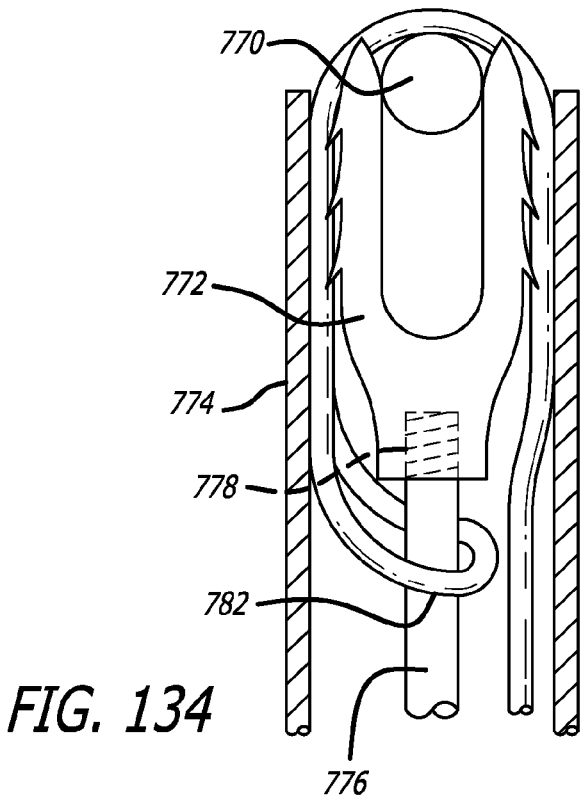
Figure 135:
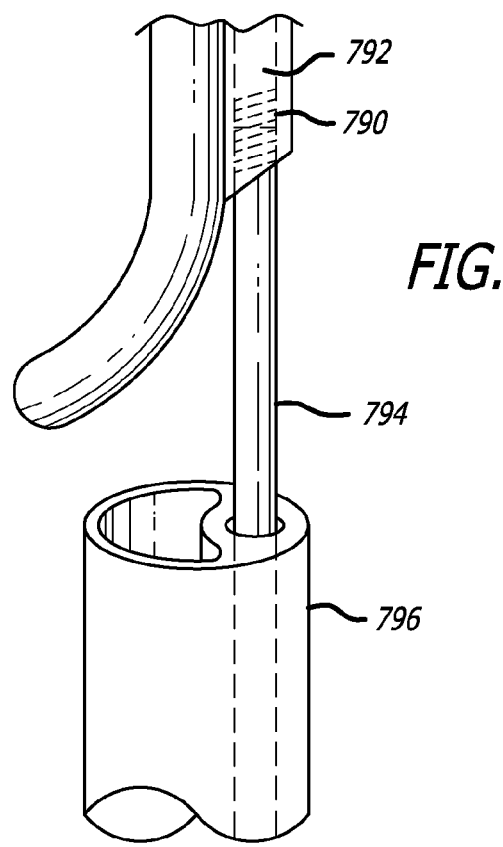
Figure 136:
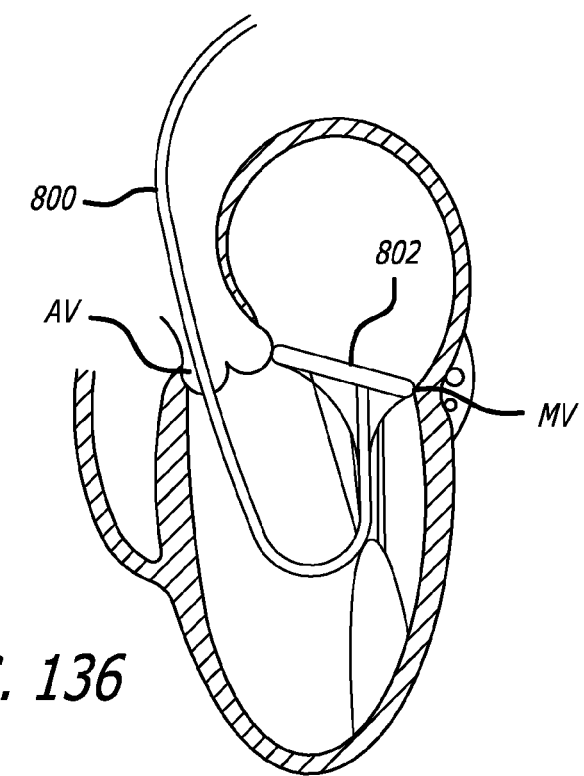
Figure 137:
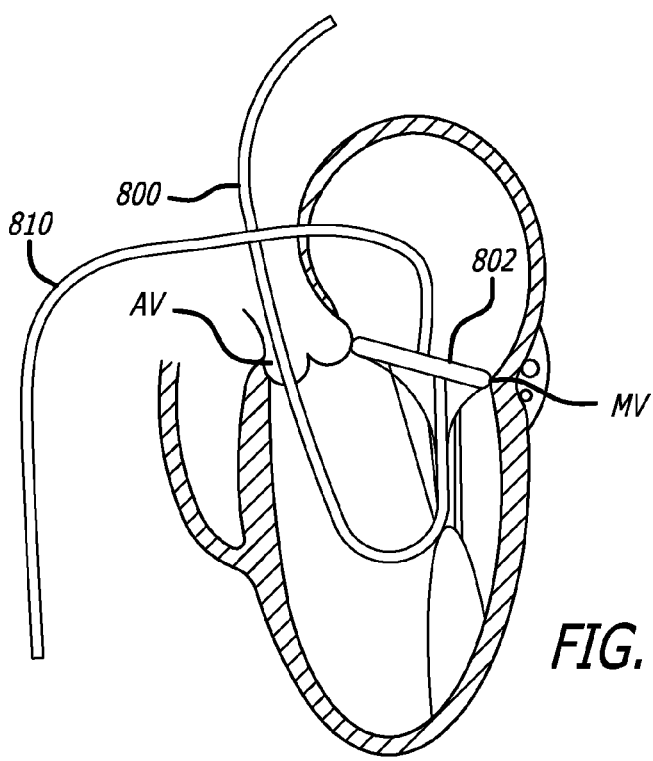
Figure 138:
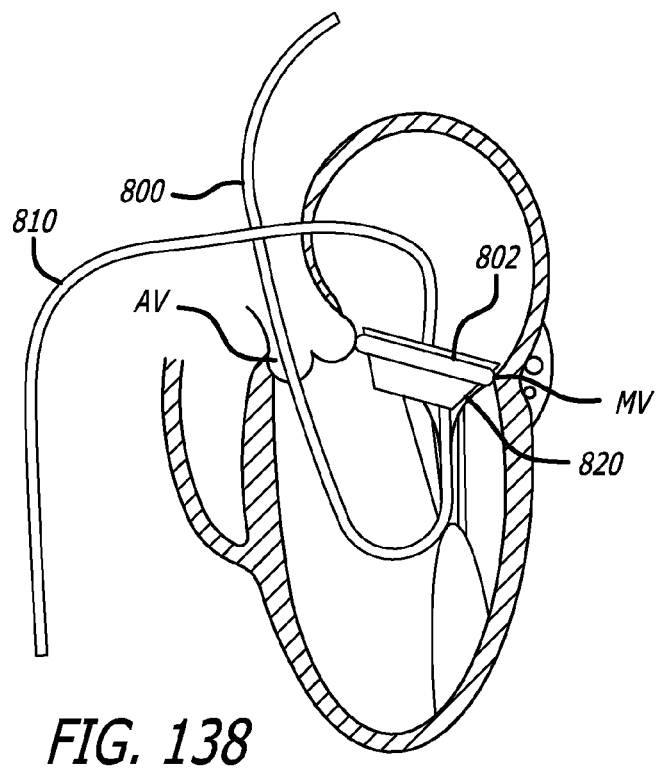
Figure 139:
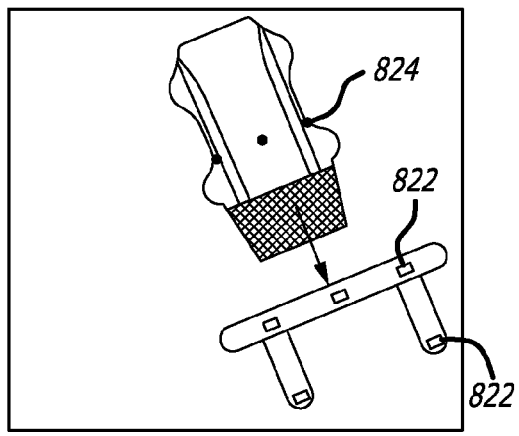
Figure 140:
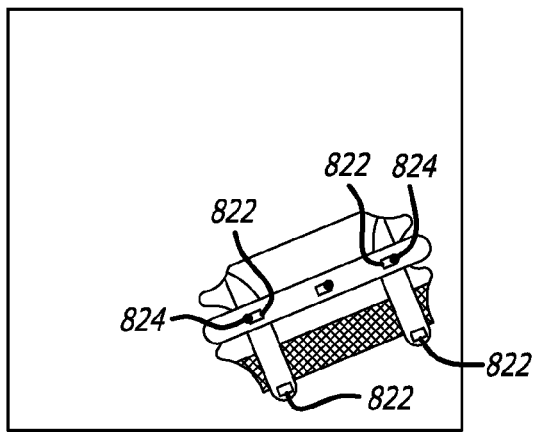
Figure 141:
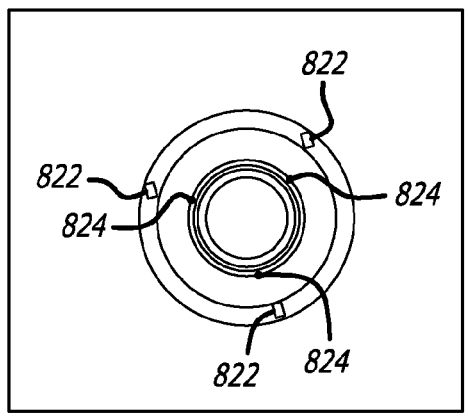
Figure 142:
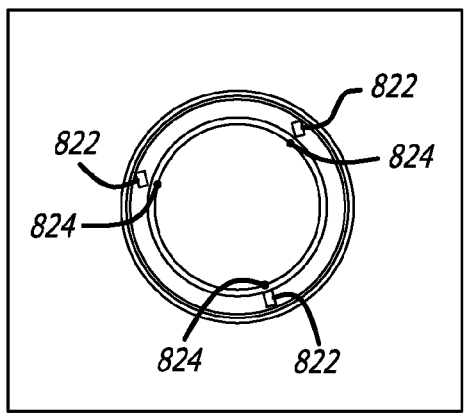
Figure 143:
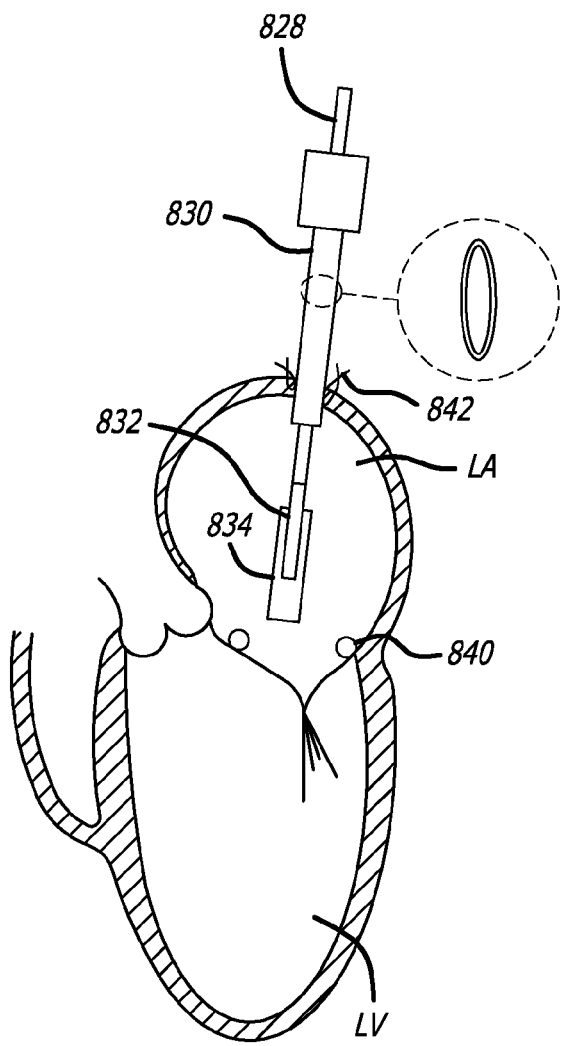
Figure 144:
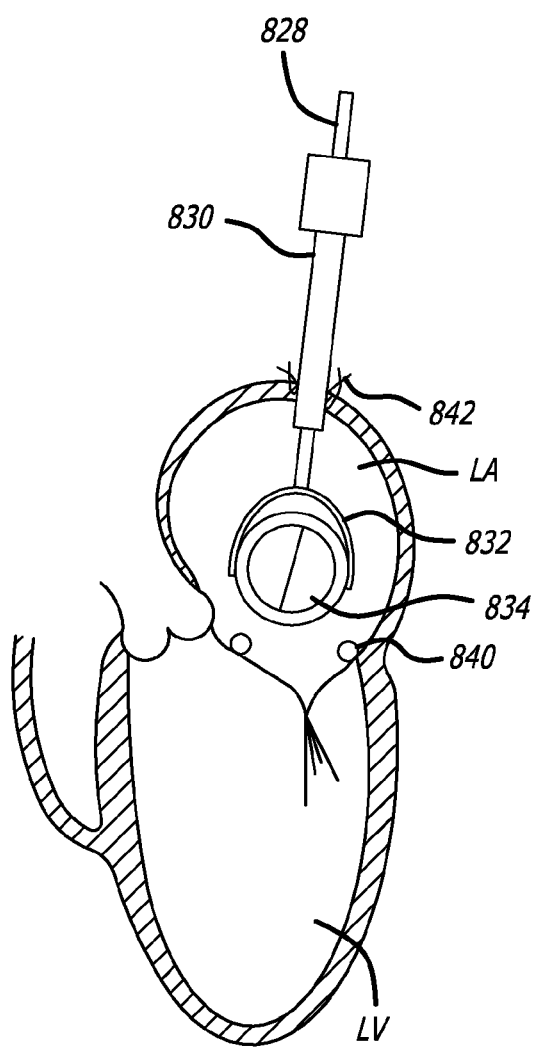
Figure 145:
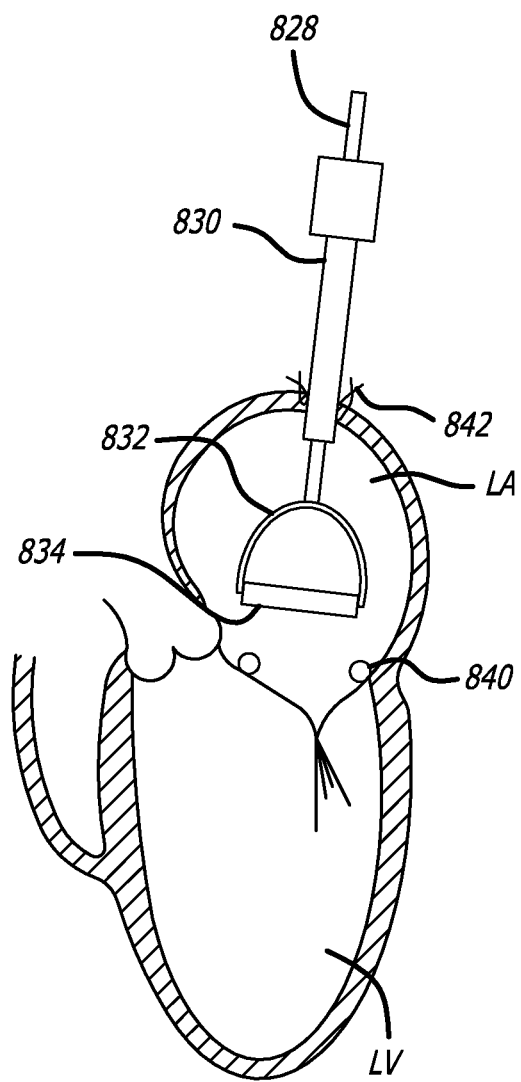
Figure 146:
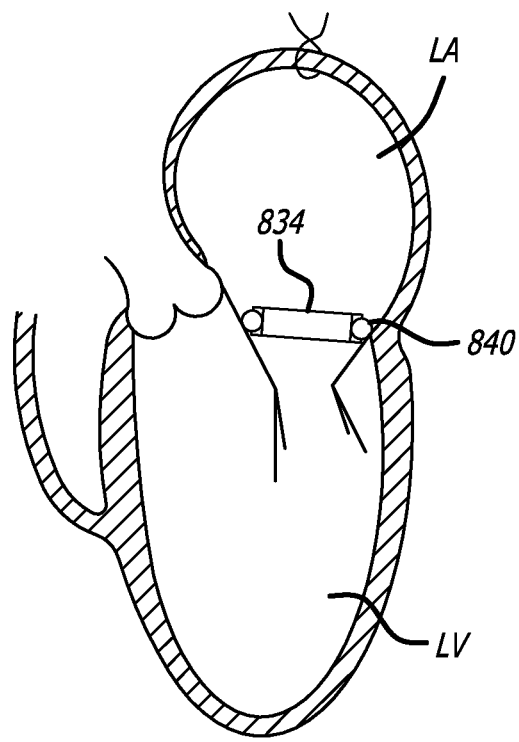
Figure 147:
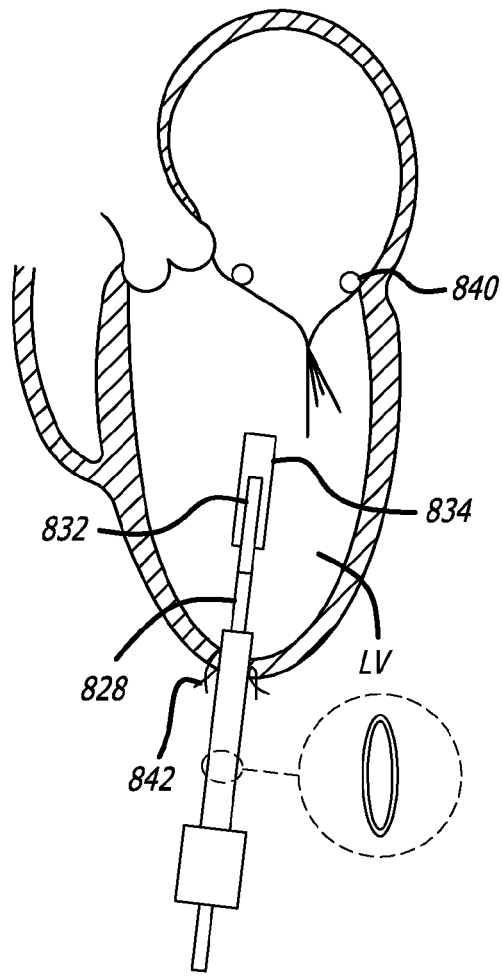
Figure 148:
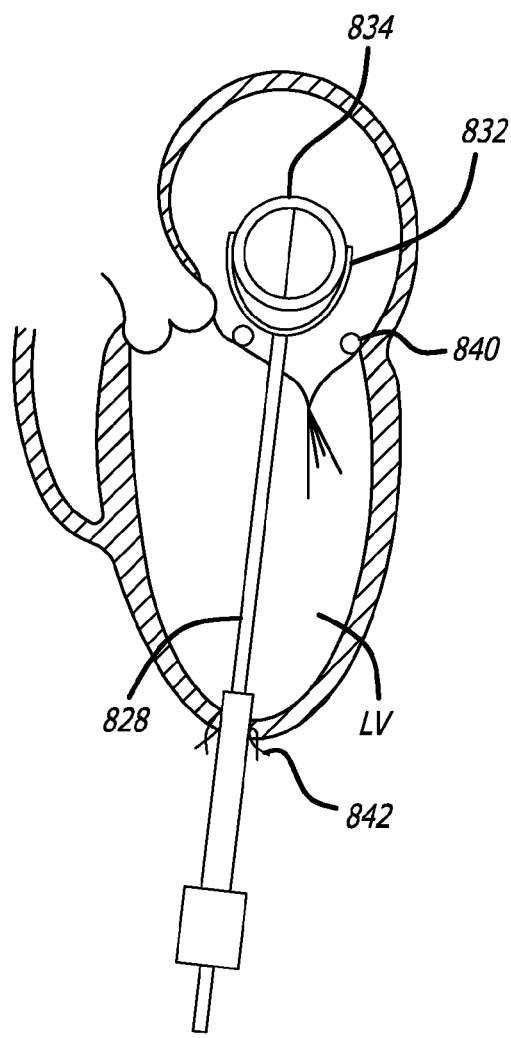
Figures 149, 150:
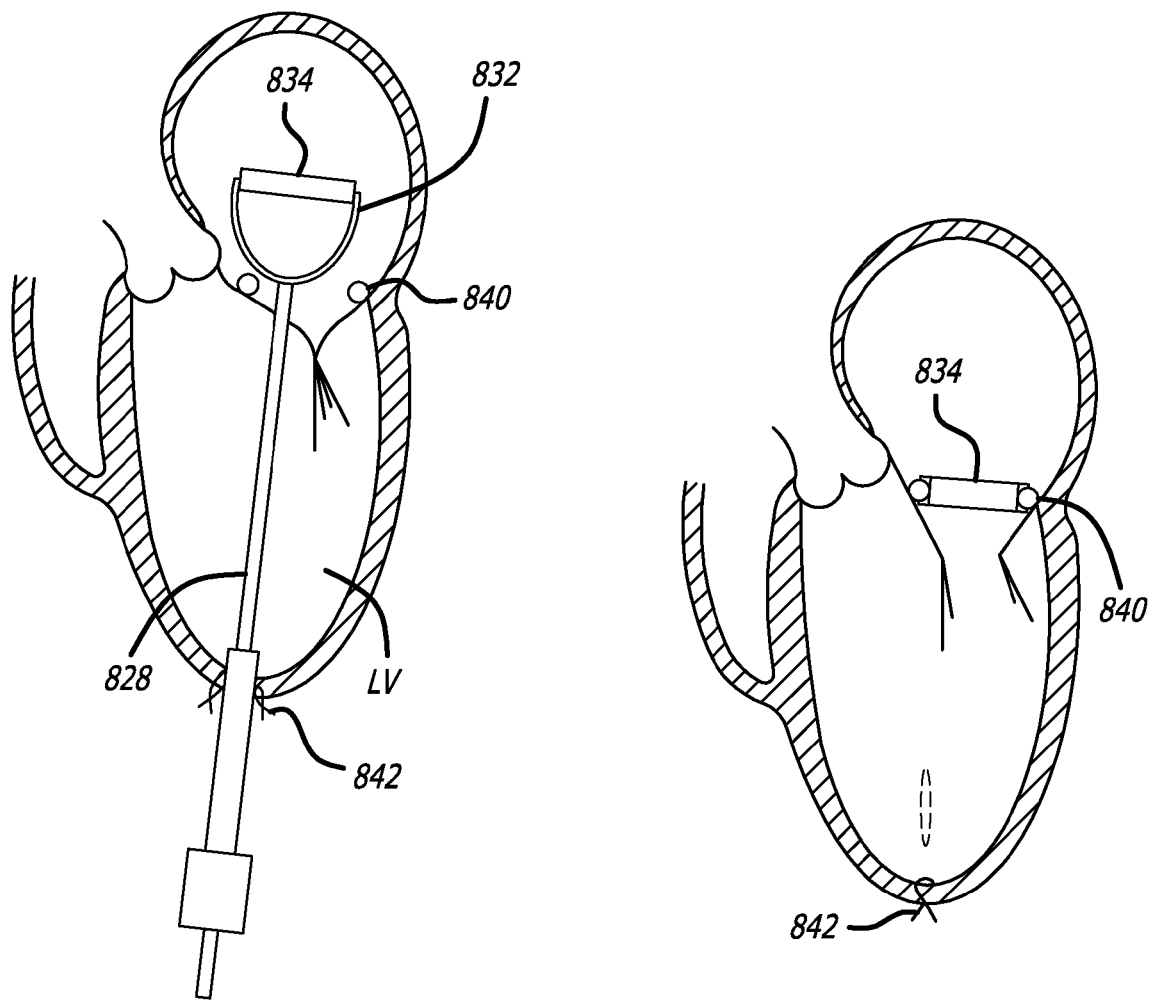

FIG. 127 is a transverse section view, depicting the anchor of FIG. 126;

FIG. 128 is a transverse cross section depicting a shaft separator;

FIG. 129 is a transverse cross section, depicting a shaft separator;

FIG. 130 is a vertical long axis, depicting the shaft separator of FIG. 128;

FIG. 131 is a transverse cross section at the mitral leaflet level, depicting the shaft separator of FIGS. 128 and 129;

FIG. 132 is a perspective view, depicting the shaft separator of FIG. 128;

FIGS. 133 and 134 are cross-sectional views, depicting the delivery catheter arrangement for securement elements;

FIG. 135 is a perspective view, depicting an alternative structure for releasing the anchor structure;

FIG. 136 depicts the first stage of an exemplary procedure for percutaneous delivery of the artificial mitral valve;

FIG. 137 depicts the transvenous, trans-septal access catheter in position that is used to deliver the valve into the anchor structure;

FIG. 138 depicts the next stage in the deployment of a percutaneously delivered, generalized artificial mitral valve of the present disclosure into the anchor structure previously positioned;

FIG. 139 shows radiopaque markers on both the anchor structure (rectangles) and the artificial valve (circles);

FIG. 140 depicts the structures of FIG. 138 with the valve having been advanced into proper axial location;

FIG. 141 depicts markers used to facilitate rotational alignment of the valve;

FIG. 142 depicts the structures of FIG. 141 with the valve deployed;

FIG. 143 is a side view, depicting a less invasive delivery of a mechanical valve into the mitral position via a trans-atrial approach;

FIG. 144 is a side view, depicting the system of FIG. 143 showing the mechanical valve rotated inside the left atrium;

FIG. 145 is a side view, depicting the system of FIGS. 143 and 144;

FIG. 146 is a side view, depicting the mechanical valve deployed in position;

FIG. 147 is a side view, depicting a less invasive delivery of a mechanical valve;

FIG. 148 is a side view, depicting the system of FIG. 147;

FIG. 149 is a side view, depicting the system of FIGS. 147 and 148; and

FIG. 150 is a side view, depicting the mechanical valve deployed in position.

DETAILED DESCRIPTION OF THE PREFERRED EMBODIMENTS

Referring now to the drawings, which are provided by way of background and example, and not limitation, the present disclosure relates to medical interventional procedures and devices. In various aspects, heart valve repair is addressed and in particular, mitral valve replacement approaches are presented.

Figure 1A:
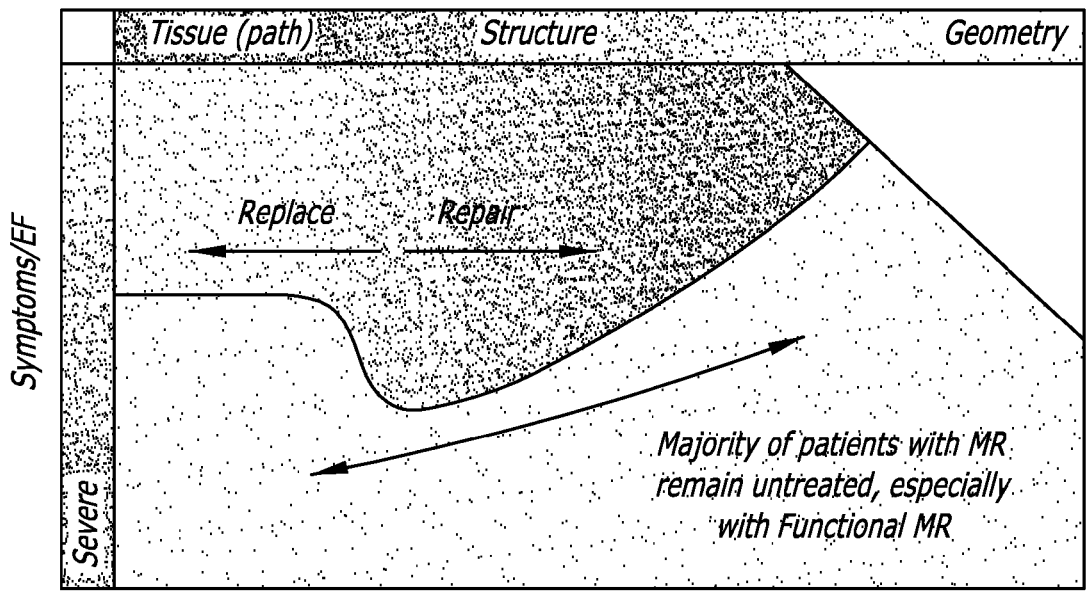
FIGS. 1A and 1B are graphical representations, depicting characteristics of potential patient populations.
Figure 1B:
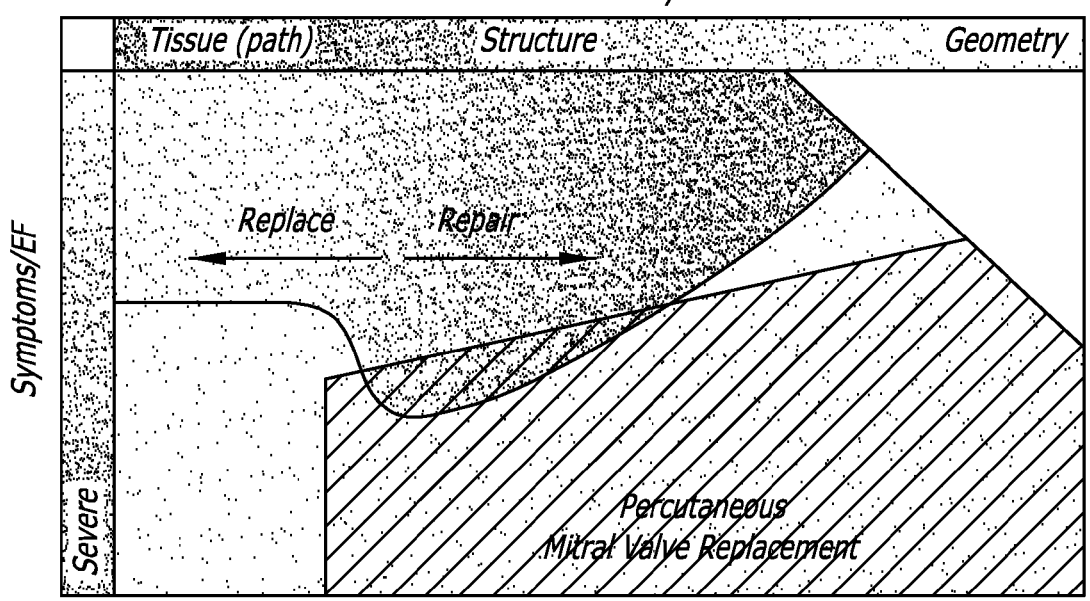

With reference to FIGS. 1A-B, there is shown a graphical representation of a potential patient population suffering from MR. Patients are classified by valve abnormality versus the severity of symptoms (i.e. ejection fraction). A decision to be made involves whether to replace or repair the subject valve. However, it has been found that a majority of patients with MR are left untreated. This is especially true with functional MR. It has been determined that such patients can be treated using a percutaneous mitral valve replacement approach.

In open surgical valve replacement, the valve is implanted in its functional configuration and size. Additionally, conventional artificial surgical valves have a sewing ring around their perimeter that is directly attached to the valve annulus tissue with multiple sutures to provide both the securement and sealing functions. The surgical approach requires sternotomy, the heart to be stopped (cardiopulmonary bypass) and the atrium to be opened.

For less invasive, beating heart approaches to valve replacement, (such as is performed in the aortic valve) whether trans-apical access or endovascular access (venous/antegrade, arterial/retrograde), the valve is not in a functional configuration and is in a compressed state to aid deployment. This requires the valve to be deployed by some means to achieve its functional configuration and size. These procedural operations of deploying a functional valve, a tissue sealing structure, and a load bearing anchor structure that is solidly secured and sealed to the native anatomic location must be performed quickly and remotely to accommodate the desired less invasive and beating heart implantation. This combination of multiple deployable elements with multiple functional requirements of the composite system dramatically increases the complexity of the system and procedure.

In general, the most difficult of the three functions to reliably achieve can be the anchoring function due to the variable and cyclical load requirements and the complexity of the anatomic structures of the native mitral valve. The sealing function of the system is similarly difficult because of the pressure requirements and again, the complexity of the anatomic structures of the native mitral valve. The simplest is the deployable valve functional element, as the TAVI experience provides a basis for the starting point design structures and mechanisms.

It is desirable to have a simple and repeatable procedure to deliver a highly functional and long lasting valve system requires a different approach than currently being pursued by others in the field.

In particular, a mitral valve replacement system according to the present disclosure includes an anchor element, a sealing element, and a valve element, and utilizes an anchor delivery system, and a valve delivery system. More than one element may be incorporated into a structure, for example, an anchor element also may comprise a sealing structure, or a valve element may comprise a sealing structure. In accordance with the present teachings, the elements of the valve replacement system may be implanted in staged procedures, for example, an anchor element may be implanted during a first procedure and a valve element may be implanted during a second procedure. As disclosed herein, the processes, systems used for implantation, and timing of implantation may vary. The present disclosure further contemplates that the anchor element (and in some cases sealing element) of the disclosed mitral valve replacement system may be used with existing valve structures, as discussed further below. Similarly, delivery systems may include those disclosed herein, but the present disclosure also contemplates that existing delivery systems may be used to deliver prior art valve structures.

It should be noted that in planned percutaneous structural heart interventions (TAVI, mitral repair, mitral replacement) (i.e. percutaneous), there are at least two procedures performed for each individual patient. The first procedure includes a diagnostic assessment and possible PCI/stenting of the patient's coronary arteries and often includes a right heart cath for cardiac physiology assessment. Valve implantation and or repair is not performed prior to knowing the patient has been previously completely revascularized if necessary.

As mentioned, generally the most difficult and most significant requirement for a less invasive valve system is the anchoring attachment of the system. The presently disclosed mitral valve replacement system staging of the anchor implantation allows exploitation of various anatomic valve and ventricular structures to achieve the required holding force of the anchor system. When performed in two time separated procedures, staging the implantation of the anchor separately from other system elements provides time for tissue ingrowth into the anchor structure and resultant strengthening of the overall holding force of the anchor structure in the anatomy.

Staging of anchor implantation allows for maintaining native valve function until artificial valve element(s) are in place.

Anchor element embodiments disclosed herein may utilize and exploit anatomic structures and geometry to attain the required mechanical holding forces whether engaged acutely or chronically with the addition of tissue ingrowth of the anchor.

As noted above, the sealing element (non-valvular) can either be a structure distinct from the primary tissue anchor or valve elements, in combination with the anchor, or in combination with the valve. When provided in combination with the anchor structure, a possibility is that the sealing and anchoring functions can both benefit from tissue ingrowth and incorporation of the anchor implant structure. This would allow for a sealed tissue/anchor implant interface that could be engaged by the valve structure element without the need for additional structures/elements to seal between the valve and tissue.

This situation provides the stable, predictable substrate to receive and deploy an artificial valve into the mitral position. The predictable substrate significantly alters and reduces the requirements placed on the valve for both delivery and deployment, making it more analogous to the aortic percutaneous valves that utilize the generally circular, tubular and solid (calcified) aortic root to attach and seal. It may even provide the benefit of having a more reliable substrate due to the lack of calcified deposits that affect valve shape and function in the current TAVI valves that can lead to perivalvular leaks.

Yet another aspect of staging is the ability to stage the actual valve/occluder function. In this approach, a non-functional valve structure could be deployed in the same procedure as that of the implantation of anchor and sealing structures, but since the valve is non-functional, the loads encountered by the system would be significantly less than those encountered by a fully functional valve, reducing the load placed on the anchor element. As the anchor and sealing structures grow into and are incorporated in the tissue/existing anatomy, the holding capability of these structures increases until such time as the valve/occluder function is deployed, either automatically (e.g., suture dissolving over time) or by some trigger mechanism or actuation during a second procedure. This actuation could be achieved remotely without invading the body (e.g., RF or ultrasound-like actuation).

The valve replacement system according to the present disclosure allows for valve delivery flexibility without, or only minor non-critical, alteration of the final implant. Specifically, tissue valves can be delivered either via a fully percutaneous procedure or a minimally invasive surgical delivery of the valve without modification to the valve implant to accommodate the alternative route.

Another aspect of staged implantation of anchor and valve structures is that previously developed technology for deployable valves in the aortic position may be able to be extensively leveraged for use in the mitral position, i.e., minimal modification of existing valve structures may permit their use in the mitral space.

Yet another aspect of having a stable consistent anchor platform for receiving a valve structure is that it allows for valve sizing that is appropriate for the patient population (FMR, structural, mixed) and even specific to the patient being treated. In other words, it allows for the largest valve possible in every patient rather than compromising size (smaller than physiologically desired) to accommodate technology limitations in systems that must combine multiple (increase complexity) valve, attachment, sealing and delivery structures.

The system according to the present teachings also allows for therapeutic flexibility of the artificial valve. The presently disclosed system allows for beating heart implantation of both tissue and mechanical valves. As disclosed herein, delivery systems are provided that allow implantation of mechanical valves via either a trans-apical or trans-atrial thorascopic route.

Overall, the present disclosure describes a system including a platform anchor, valve, and delivery technology that allows therapeutic flexibility (mitral replacement with either tissue or mechanical valves), implantation flexibility via either fully percutaneous or minimally invasive (trans-apical, trans-atrial) procedures, minimized delivery complexity to allow a simple to perform procedure, and a patient population that is not restricted by the underlying pathology.

It is contemplated that the structural substrate of the mitral annular be managed. Also, the mitral annulus is typically nonplanar, non-circular in shape, flexible and distensible. These all contribute to a complex substrate to effectively attach an artificial valve, and specifically the anchor structure. Complex valve/ventricle structural relationships should be managed. The apparatus of the mitral valve includes multiple leaflets with multiple lines of coaptation all connected via chordae tendinae at the leaflet tips to the LV wall or papillary muscles. This creates possible of entanglement of system elements during implantation and if the subvalvular apparatus is not maintained or is damaged, the LV geometry may be negatively altered increasing LV wall stress and reducing overall cardiac function in spite of the artificial valve eliminating MR. Moreover, the load requirement are contemplated to be managed. The static functional load on the implanted artificial valve may be calculated by Valve area×Trans-valvular (LV pressure—left atrium pressure) pressure. This is generally approximately 3 pounds with a range of 1-4 pounds. Because the mitral valve is in a cyclical flowing system, the requirements of handling the pressure load is accentuated by a closure or impact load created by stopping the momentum effect of the LV pressurized blood. The blood that starts to flow back towards the atrium during systole must be decelerated. And diverted to the aortic outflow.

Another aspect is consideration of the anchor implant is the load distribution or force per unit of area of anchor attachment. This can be at a level that does not allow the anchor structure(s) to pull out of the tissue once attached. One mechanism to minimize is to have a relatively rigid anchor frame such to help distribute the valve load across the entire anchor surface in contact or attached with the tissue. Another mechanism is to have multiple points of attachment along the anchor. The tissue anchor geometry is another structural design consideration in order to prevent tissue migration or pull through due to excessive local forces or tissue necrosis that can be encountered when the tissue is overcompressed. To maximize acute mechanical hold in the tissue, the profile geometry of the anchor tissue element can be designed to maximize the breadth and depth of tissue engagement as well as the surface width and geometry of the penetrating element. The tissue used to provide the holding force for the anchor can be exploited such that certain regions of the mitral valve have greater intrinsic tensile strength (e.g. trigone region) or utilize tissue that has a response that enhances the extent (thickness, area) of ingrowth (LV muscle wall). The tissue collagen orientation in certain regions needs to be accounted for if it is small chain, non-oriented fibers or can be used to maximize hold if it is larger chain and oriented collagen.

Due to the continuous and cyclical loads and motion of the system, anchor device biostability can be required, specifically fatigue resistance, corrosion resistance and overall mechanical durability. One of the system elements is intended to interface with tissue to form a seal. This can be the anchor forming the seal and the valve seals to the anchor, or the anchor holds valve and a valve element seals to the tissue. The implanted valve interface to anchor can provide sufficient and stable holding capability with a transfer of the valve load effectively onto the anchor. This may be accomplished by a frictional fit via expansion (balloon, self) of the valve into the anchor and/or tissue or a mechanical interlock mechanism between the anchor and valve. Further, the anchor implant structure can be a biocompatible device, including specific biocompatibility for blood contact and tissue contact.

The specific anatomic locations that may provide mechanical and structural attachment of the anchor is another area of consideration. The anchor may be designed to incorporate one or more of a commissural location such as the anterior trigone region or the posterior leaflet cleft. An attachment location could also be the anterior portion of an atrial wall, or at an annular region/surface (posterior or anterior). Leaflet capture is also contemplated such as at the sub-posterior leaflet or the sub commissural leaflet. Attachment can also be at or within the left ventricle (endocardial) such as to the posterior wall (including posterior leaflet capture or a papillary space wedge), the apical/sub-papillary, the anterior/posterior wall bridge, or transmurally (septal, free wall, apex).

The anchor itself can include various approaches to support the skeletal structure. In one approach, the structure can be a supra-valvular structure with commissural feet. The commissural feet/projections can be structures which are multi-functional elements that can provide mechanical/geometric anchoring, penetration (needle/barb like) securement, and tissue based incorporation (in-growth) including sub-valvular/sub-leaflet structures that extend into the LV wall, all of which do not interrupt leaflet, chordae or native valve function. Also, they can provide a positioning basis for the entire anchor because of their engagement with the commissural clefts in the anterior and posterior leaflets while still avoiding interaction or disruption of the chordae or native leaflets. More detail on specific methods of the anchor/tissue interface are described below.

The ring or top structure can be designed to provide a relatively circular, non-distensible, non-elongating homogeneous frame substrate that the artificial valve can engage and attach to during its deployment. This can be adapted to function much like the calcified aortic root for TAVI without the in-homogeneity or need for pre-dilatation. This structure may be continuous or interrupted, and completely around annulus or only partially around annular circumference. In particular, it can be sinusoidal in plane of valve leaflets trying to create continuous attachment around entire circumference (each sinusoid comes in and out of plane) or sinusoidal perpendicular to valve bridging from point to point creating, multiple attachment points, thereby allowing for tissue ingrowth between sinusoidal points of native leaflet or annulus tissue contact/engagement. The anchor can be malleable with points of attachment between commissures, a single wire or multiple connected wire components, or be formed into a saddle configuration to approximate natural saddle geometry of valve (may be based off of 3d echo or CT to determine geometry).

There may further be a covering of the skeletal frame. The covering of the anchor skeleton can provide opportunity for facilitating collagen tissue ingrowth into or onto the implant structure and/or covering in locations such as on top (atrial side) of leaflet or annulus, at side of leaflets or annulus, at a ventricular wall at sub-valvular level, or underneath (ventricular side) of the leaflet or commissures.

A superstructure above the valve annulus may provide options for valve attachment to the anchor or even an alternative therapy such as mitral repair via a septal lateral cinch. Various superstructures above the annulus can include A2 P2 points of attachment, two circles to allow for double aortic valves, or use of the atrial wall behind A2 or P2.

Materials for components used in multiple combinations and configurations, may include metals, especially for the anchor skeleton or frame structures such as Nitinol because of its superelasticity and ability to be compressed into a deliverable shape/state and then deployed into a functional state, titanium due to its strength and biocompatibility, SST: hardened for its strength or malleable to aid in conforming to shape, cobalt/chromium alloy for strength and known valve component implant history; or composites to provide multiple properties based on anatomic location. Tissue elements also may be incorporated on the anchor implant to aid overall function of holding or tissue engagement and sealing including pericardial (bovine, ovine, porcine) tissue or valve tissue (bovine, ovine, porcine). Further synthetic polymers can be used as biocompatible elements in implants and on the anchor due to their know tissue and blood compatibility properties. These can include Elast-Eon (a silicone and urethane copolymer), ePTFE, urethane, silicone, PEEK, polyester (PET), or UHMWP.

The anchor implant can use one or more mechanisms to achieve the stable, reliable, and consistent holding forces necessary for the overall system. The anterior commissural/trigoneal region has been found to be a consistent and predictable anatomic feature across multiple patient populations. The projections or feet placed in this area will have minimal or no impact on native leaflet and valve functions. It is also an area that accommodates the anchor structure to have contact with the supra, intra, and sub valvular structures including the LV wall beneath and behind the commissural leaflet. The tissue substrate of this area is also very advantageous as the trigone/annulus consists of highly organized and strong collagen and the well perfused muscle tissue provides a good ingrowth substrate for added chronic stability.

Geometric/mechanical holding force for anchor that exploits the geometry/configuration of anatomic structures (relative to force vector) to achieve the necessary holding force required by a deployed artificial valve or other therapeutic element is further contemplated. The force vector encountered by the anchor structure's commissural projections are substantially under shear loading verses a perpendicular load relative to the tissue. Commissural projections or foot elements that are able to deploy behind the anterior and posterior leaflets in the cul de sac where the leaflet meets the annulus provides for direct mechanical holding capability. The commissural projections of the anchor structure connected and bridged to each other provide an ability to create a mechanical wedge structure to resist the force and hold the valve in position. LV wall projections of the commissural feet can provide for the ability to develop deep tissue penetration elements into the muscle, wider elements to increase surface area of contact/attachment, and longer projections to increase capability. Moreover, because the projections can be placed such that they are Supra annular and Sub-annular, a C like structure in cross section can be utilized that is either connected or clamped. With regard to tissue penetration based securement, direct mechanical holding force is contemplated for an anchor that utilizes the natural strength of the LV and leaflet tissues to hold onto anchor structure. These elements can be configured to either be inserted into the tissue and resist pull out (barb like), or they may go into and out of tissue to provide a tissue "bite" like a stitch, or both elements can be employed. The structure can be located posterior annulus or entire annular perimeter, or adjacent leaflet tissue, the trigone/anterior annulus, an endocardial LV surface or LV Muscle tissue. Further, the tissue penetration securement elements can be linear (staple or nail like), helical (rotation axis is perpendicular to tissue interface or rotation axis is parallel to tissue interface (in/out/in/out)), curved and or curled, or bent (L shaped or S shaped).

It is also contemplated to use chronic ingrowth to provide long term stable implantation of the artificial valve and proper sealing function. In addition, chronic ingrowth of implant structural elements can serve as a fundamental mechanism to achieve the necessary holding force of the anchor functional element of the system. It exploits the natural healing response to foreign bodies placed into tissue and the blood stream to develop a strong collagen based tissue connection between the implant surface structures and the native valve tissue with a possible endothelial surface. This can be achieved while still managing the response to prevent unwanted damage to anatomic structures, damage to blood elements, or creation of thromboemboli.

More areas of consideration are the surface composition elements, specifically the material choice and texture to promote tissue reaction and device incorporation with maximal force holding capability. These elements can also be incorporated onto the tissue penetration elements to further increase the holding force by incorporation deep into tissue rather than just at the surface. The anchor can have a gross surface modification (barbs, slits), a surface texture/pores to promote ingrowth and mechanical hold, a fabric material covering (Dacron velour, double velour, ePTFE), a wire brush (multiple short wire elements) or an adhesive. There can further be a single or multiple points of attachment, planar attachment or by way of a confluent surface. Moreover, the tissue/anchor interface can be rigid or flexible and can include a wire frame structure that puts a compressive force onto surface contact interface to promote increased response. Also, tissue surface modification can include an abrasive, a chemical irritant to promote inflammatory response or application of heat.

In current conventional approaches to valvular intervention, a diagnostic echocardiograph is initially performed to assess valve function followed by two percutaneous procedures. First, a diagnostic angiography is performed with or without a right heart catheterization to assess, for example, whether they might also require revascularization first, prior to valve intervention. Here, patients do not receive valve therapy without the patient being fully revascularized. Thereafter, at a different time and place, valve replacement therapy is performed involving fixation/attachment, accomplishing a tissue sealing interface, and valve deployment and then release. In contrast, the presently described approach, however, can include an assessment involving a diagnostic echocardiography followed by a unique percutaneous valve procedure sequencing. First, a diagnostic angiography (+/− right heart cath) can be performed along with anchor fixation/attachment and anchor/tissue sealing. Subsequently, either later or during the same interventional procedure, valve replacement therapy can occur involving valve deployment and release. Thus, since the anchor implant allows the native valve to remain functional, the anchor implantation procedure could be added to the end of the angio (+/− PCI), and not require a separate interventional procedure. A quick, simple, and reliable anchor deployment procedure could permit a fully ingrown structure that significantly enhances the holding force of a subsequently implanted replacement valve. Tissue ingrowth of the entire anchor perimeter, or at key positions thereon, can in fact provide the necessary tissue seal in advance of valve deployment. Moreover, the anchor design could be simplified due to less required acute holding force. Therefore, a tissue incorporated and healed anchor provides a structure to perform several methods of annular adjustment, including plication, reduction annuloplasty, and septal-lateral cinching.

Figure 2A:
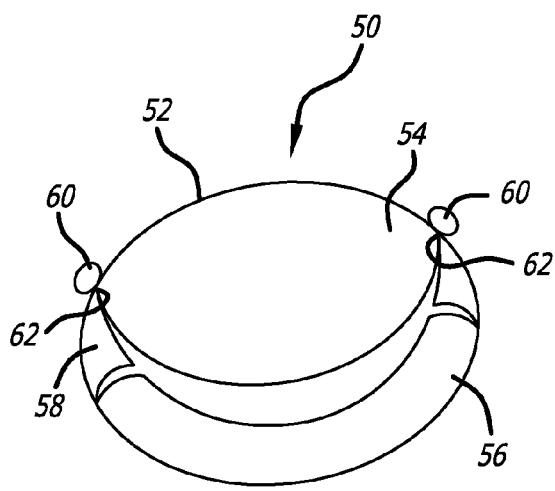
FIG. 2A is a schematic drawing of the mitral valve anatomy at the level of the mitral annulus.
Figure 2B:
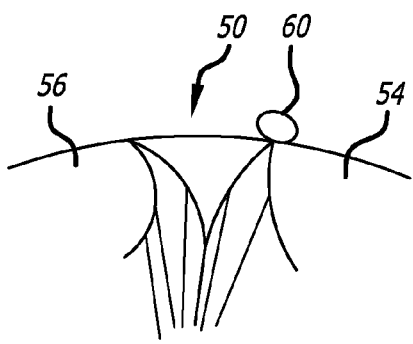
FIG. 2B is a side view, depicting a portion of the schematic from FIG. 2A.
Figure 2C:
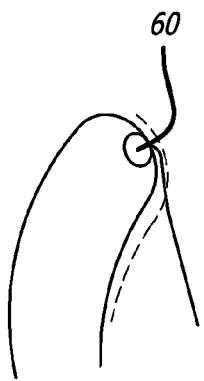
FIG. 2C is a schematic section view of the mitral commissural area, showing the region of possible anchor and/or anchor projection tissue engagement.
Figure 2D:
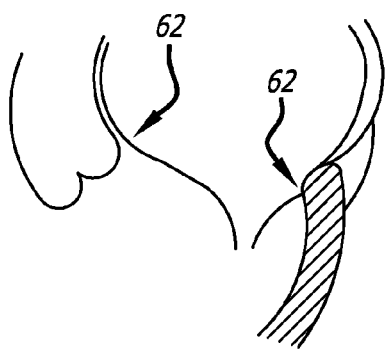
FIG. 2D is a vertical cross section through the aorta and the A2/P2 segment of the mitral valve, depicting possible locations for attachment of the anchor to the valve tissue or anatomy.
Figure 2E:
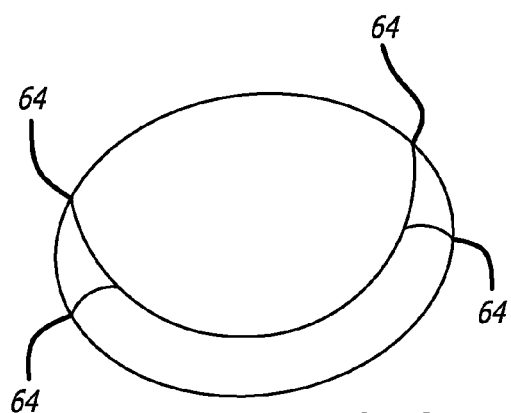
FIG. 2E is a transverse (short axis) cross section of the heart at the mitral valve annular level, depicting the commissural and posterior leaflet cleft locations as possible attachment locations for the anchor.

There are certain desirable anchoring locations for an anchor implant. Direct attachment to tissue is contemplated at locations adjacent the mitral valve, as are locations for placement of anchor projections at leaflet cleft locations. Again, it is intended that there be low or no impact to native leaflet function as a result of the implantation of an anchor implant, so as to maintain the pre-existing native valve function until a replacement valve is implanted. At the mitral valve 50 (See FIGS. 2A-2E), there is of course the mitral annulus 52 defining structure from which the anterior leaflet 54 and posterior position leaflet 56 extend and articulate. Between the anterior and posterior leaflets 54, 56 are commissural leaflets 58. The trigones 60 are positioned at a perimeter of the anterior leaflet 54 and adjacent the commissural leaflet 58. Commissures 62 are the openings or slits dividing the anterior leaflet 54 form the commissural leaflets, and positioned near the trigones 60. Such structure defines consistent and predictable anatomical features across patients. Notably, the high collagen annular trigone 60 generally can be relied upon to present a strong anchoring location. The muscle tissue in this area also provides a good ingrowth substrate for added stability. There is also a potential for sub-leaflet attachment for more stability (See FIG. 2C). Accordingly, primary anchoring locations 62, 64 for an anchor implant are included in FIGS. 2D and 2E.

Figure 3:
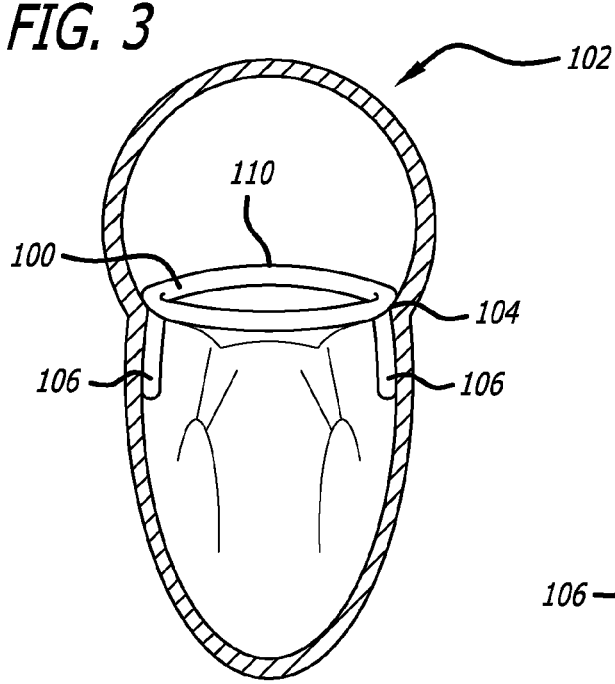
FIG. 3 is a vertical cross-section of the heart, depicting the posterior wall of LV with an exemplary anchor embodiment.
Figure 4:
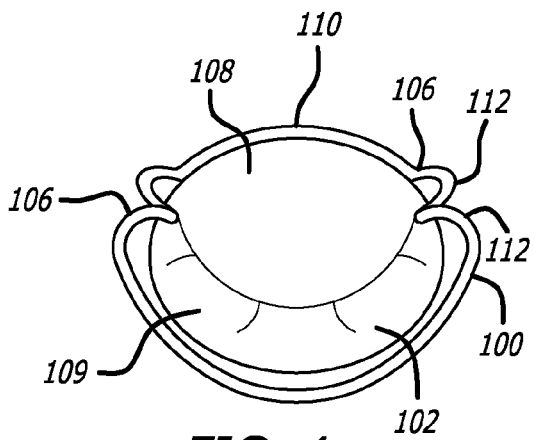
FIG. 4 is a transverse (short axis) cross section of the heart, depicting the mitral valve annular level of the exemplary embodiment of FIG. 3, showing the circular anchor structure.
Figure 5:
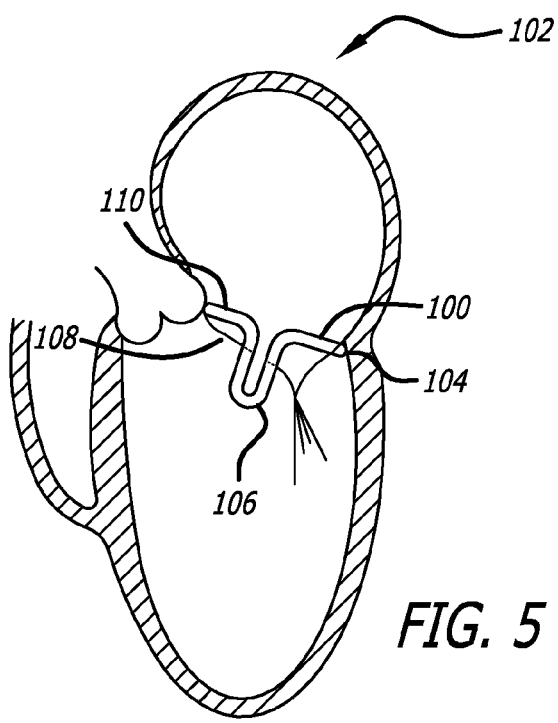
FIG. 5 is a vertical cross section through the aorta and the A2/P2 segment of the mitral valve, depicting the anchor of FIG. 3.
Figure 6:
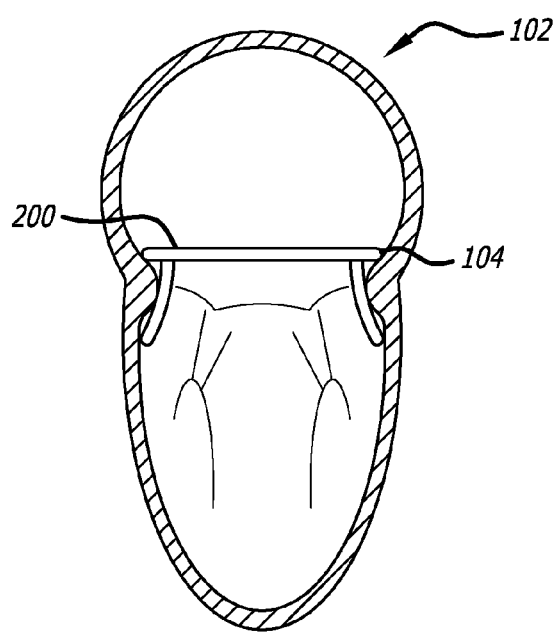
FIG. 6 is a vertical cross-section of the heart looking at the posterior wall of LV, depicting another anchor structure.
Figure 7:
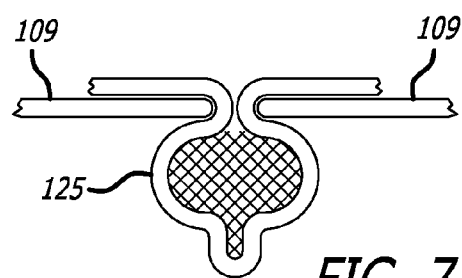
FIG. 7 is a cross section view of the anchor structure of FIG. 6 taken at the natural cleft, depicting capture of the anterior and posterior leaflet.
Figure 8:
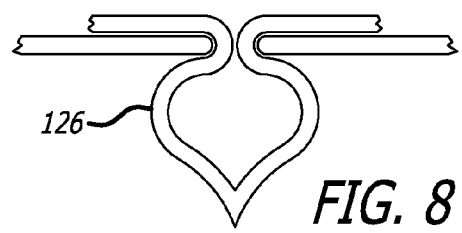
FIG. 8 is a cross section view of an anchor, depicting the P2 segment of the posterior leaflet.
Figure 10:
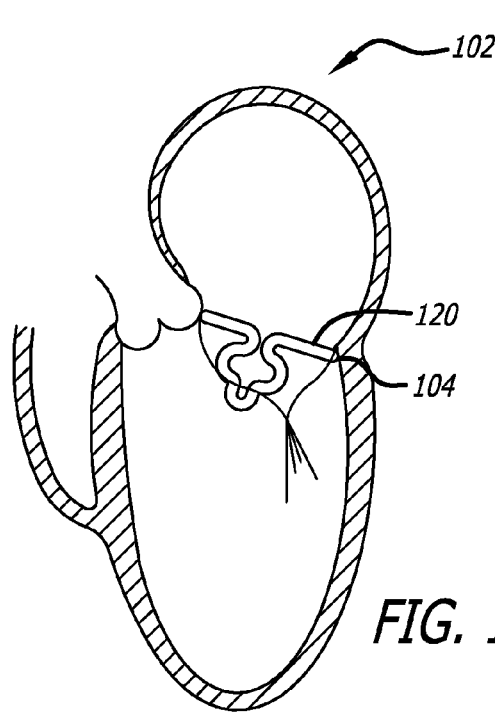
FIG. 10 is a vertical cross section through the aorta and the A2/P2 segment of the mitral valve, depicting the anchor of FIGS. 6 and 7.
Figure 9:
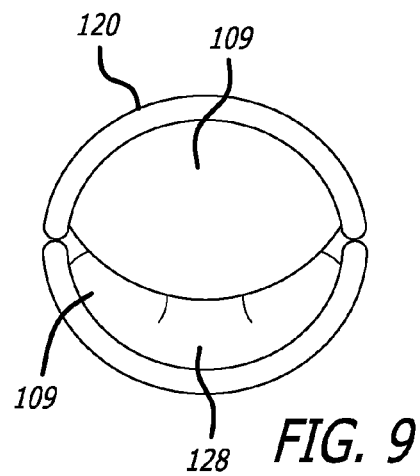
FIG. 9 is a transverse (short axis) cross section of the heart at the mitral valve annular level, depicting the anchor structure of FIGS. 6 and 7.

Turning now to FIGS. 3-5, there is shown one embodiment of an anchor implant 100 configured for atrial anchoring and implantation within the heart 102 at the mitral valve annulus 104. The anchor implant defines a supra-annular ring sized and shaped to be placed at the annulus, and includes commissural projections 106. As shown in FIG. 3, the projections 106 can be placed at an anterior commissural trigone 108. As described above, the commissural projections 106 are configured to extend between leaflets 109 without interfering with their functions (See FIG. 4). Moreover, as shown, the implant 100 includes a generally circular body 110 which can be formed from a wire or other structure, and the projections 106 are loops extending away from a plane defined by the circular body 110. It is to be further recognized that the body 110 includes a pair of bends 112 configured on opposite sides of the projections 106 to thereby provide necessary stress relief and clearance for the placement of the projections between leaflets 109. Furthermore as noted previously, the anchor 100 can be covered with various materials, such as PET and ePTFE, so as to present a desired biocompatible surface to body tissue.

As shown in FIGS. 6-10, various other approaches to the anchor implant are contemplated. As before, the anchor 120 can be placed at the mitral valve annulus 104 with projections extending beyond and between the leaflets 109. The projections 125 can be one or more of an expanding structure deployed through the coaptation line and below the leaflet 109 thereby capturing the anterior and posterior leaflet adjacent the commissures (See FIG. 7) or can define a piercing anchor 126 (See FIG. 8). In a further aspect, the piercing anchor 126 can be deployed in the P2 segment 128 of the posterior mitral valve leaflet, for example (See FIG. 9), so that the leaflet is punctured and captured by the anchor 120. Thus, a further secure attachment in anatomy can be achieved by way of expanding anchor or piercing anchor structure.

Figure 11:
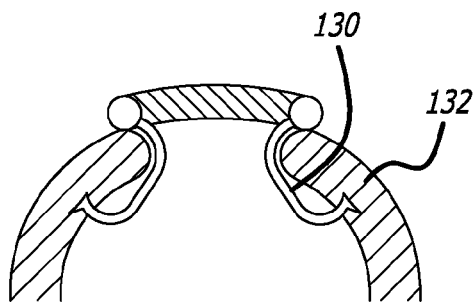
FIG. 11 is sectional view of an anchor structure and the heart at the commissural location.
Figure 12:
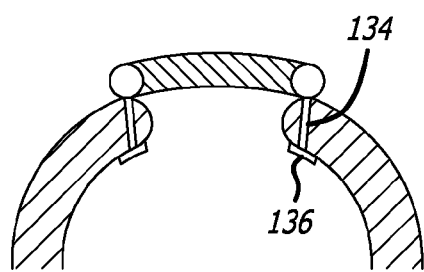
FIG. 12 is a sectional view to FIG. 11, with penetrating projections and a flattened structure at tip to create a mechanical hold.

Two additional approaches to penetrating projections for use in connection with an anchor implant are shown in FIGS. 11 and 12. In one approach (FIG. 11), a projection 130 can form a hook-like member with a barb 132 at its terminal end. Such structure defines a geometric interference with wall anatomy below a leaflet and the barbed end 132 penetrates the tissue of the LV to provide a secure attachment. Alternatively, a projection 134 can be configured to penetrate commissural anatomy and terminate with a T-bar 136 which engages an external wall of the LV to thereby provide a secure attachment.

Figure 13:
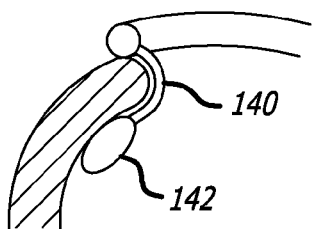
FIG. 13 is cross section of an anchor structure and the heart at the commissural location, showing the anchor structure that has geometric interference to the wall beneath the leaflet.
Figure 14:
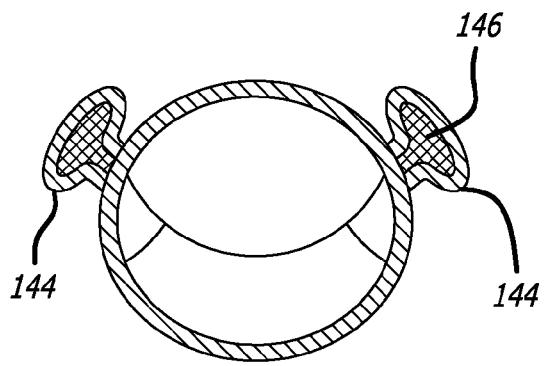
FIG. 14 is a transverse (short axis) sectional view at the mitral valve annular level, showing the anchor of FIG. 13 at the anterior commissural locations.
Figure 15:
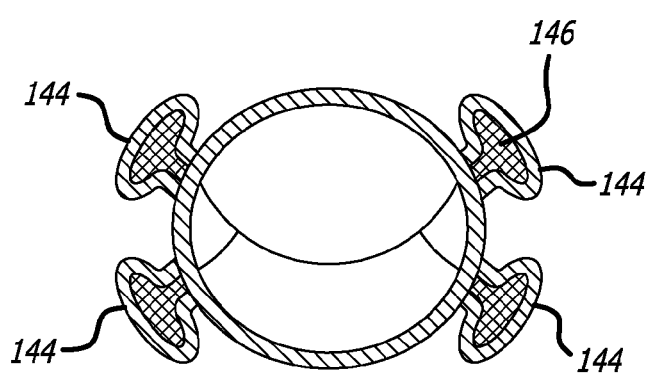
FIG. 15 is a transverse (short axis) sectional view, depicting another embodiment of an anchor.

Non-penetration or non-piercing projections are also contemplated. As shown in FIG. 13, a projection 140 can be contoured to match a profile of the wall beneath a leaflet, and further include a foot pad 142 for engaging tissue. As shown in FIGS. 14 and 15, the anchor implant can include a plurality of projections 144 having a looped shape and including webbing 146 for tissue ingrowth. Here, the looped structure of the projections 144 include a neck sized to fit between commissural slits and about commissural leaflets, the loop structures residing below the leaflet and against the LV wall to provide a secure engagement.

Figure 16:
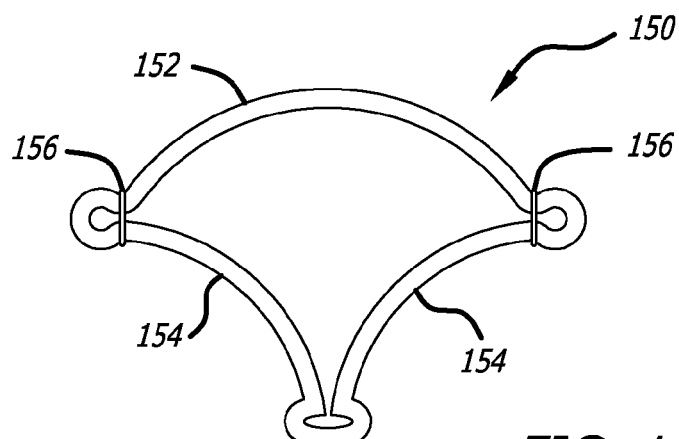
FIG. 16 shows a top view of an embodiment of an anchor structure in the nondeployed or delivered state prior.
Figure 17:
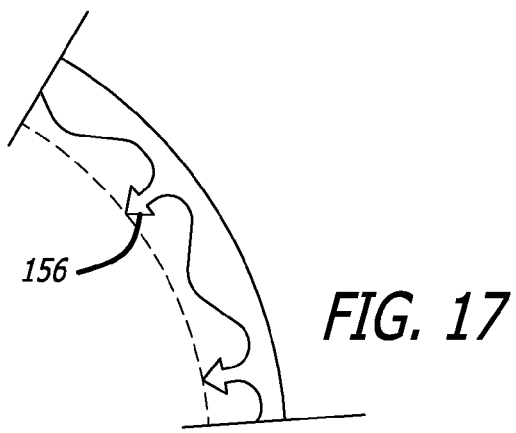
FIG. 17 is an magnified partial view, depicting a penetrating structure of FIG. 16 taken from between points A and B in FIG. 16.
Figure 18:
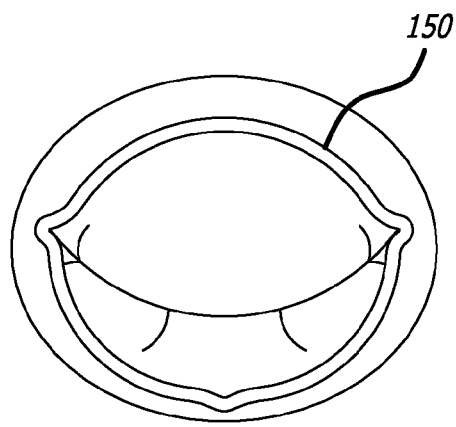
FIG. 18 is a top view of the structure of FIG. 16, depicting a deployed configuration.
Figure 19:
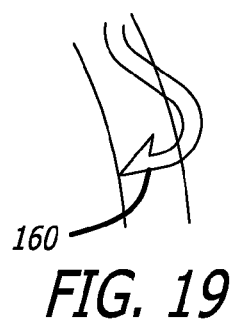
FIG. 19 is a magnified partial top view, depicting an alternative penetrating structure.

In another approach (See FIGS. 16-19), the anchor implant 150 can define an expandable body. In a compressed or contracted state (FIG. 16), the anchor implant 150 is smaller for delivering to an implantation site, whereupon the anchor 150 is expanded (FIG. 18) to securely engage tissue. The implant can include a first convex side member 152 configured between a pair of concave members 154. The junctions between the members can be looped to provide desired stress relief and a platform against which the convex member 154 can expand or open. Temporary restraining bands 156 are placed about the looped structure at the junction between the convex member 152 and each of the concave members 154. Further as shown in FIGS. 17 and 19, external surfaces of the member 152, 154 can be equipped with tissue penetrating structure such as arrow-like barbs 158 or fish hooks 160. One approach to converting the anchor implant 150 from its contracted state to its expanded state is to employ an expandable member such as that of a balloon catheter (not shown). At an implantation site (See FIG. 18), the expandable member is placed within an interior of the members 152, 154 and expanded to facilitate the conversion of the concave members 154 to convex members. Such action overcomes the restraining bands 156 and facilitates the advancement of the tissue penetrating structure with tissue.

Another approach to structure for penetrating tissue is shown in FIGS. 20 and 21. Here, the penetration structure is embodied in a staple-like structure 162 including a pair of spaced arms 164 joined at a U 166. Angled barbs 168 are further provided on lateral sides of the arm 164 to provide a further secure engagement to tissue. In one approach, the staples 162 are deployed about an anchor implant such that the U structure 166 captures the anchor implant and the arms with barbs secure the anchor in place. A threaded base 170 is further provided to connect the staple 162 to a push rod or wire delivery system (not shown). In this way, one or a plurality of staples 162 can be advanced to the implantation site to help securely set an anchor implant.

Various other approaches to an anchor implant are shown in FIGS. 22-38. FIG. 22 depicts an implant 180 embodying a generally FIG. 8 shape connected at its middle by a connection cord 182. A pair of commissural projections or feet 184 are further provided and spaced along the implant to reflect contouring of commissures (points A and B) of a heart valve. The feet 184 can define loops held in shape by a retaining band 186. Another elongate loop 187 is formed at one end of the connector cord 182 and is configured to extend laterally. The assembly can be further provided with webbing 188 for tissue ingrowth, the contour of the figure 8-shape and the elongate loop 187 providing structure across which the webbing extends to define a generally circular overall implant body structure, with the feet 189 extending therefrom.

Figure 23:
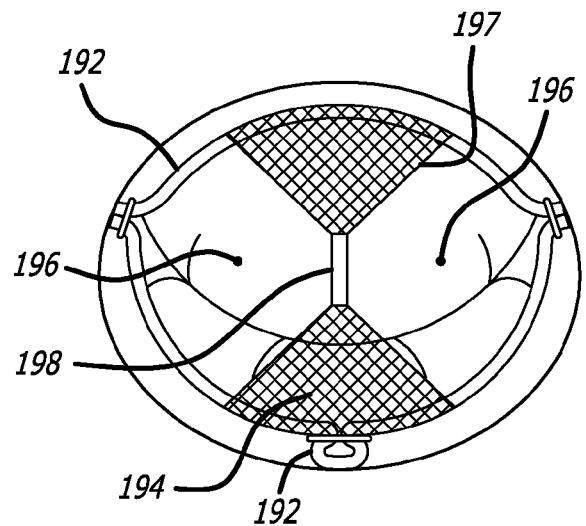
FIG. 23 is a transverse view, depicting a wire frame anchoring structure

The approach to the anchor implant 190 shown in FIG. 23 also is embodied in an assembly having a generally round or circular profile. The implant 190 includes a generally circular wire frame 192 having a covering and a plurality of feet, two of which are intended to pass through valve commissures and a third positioned at a P2 location. A flexible fabric web 194 is configured across the wire frame 192, the web being centered about center points 196 of the valve and including a pair of triangular sections 197 joined by a middle band web section 198.

Figure 24:
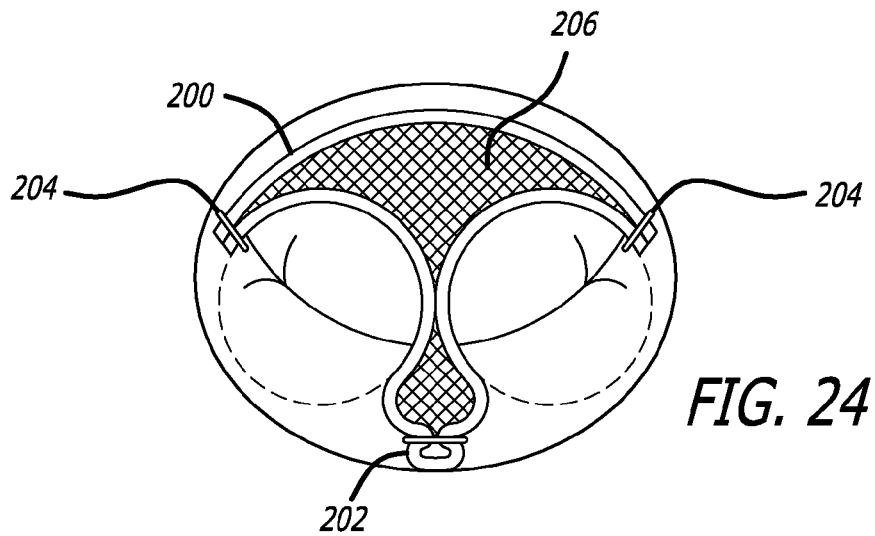
FIG. 24 is a transverse view, depicting another anchor wire frame.
Figure 25:
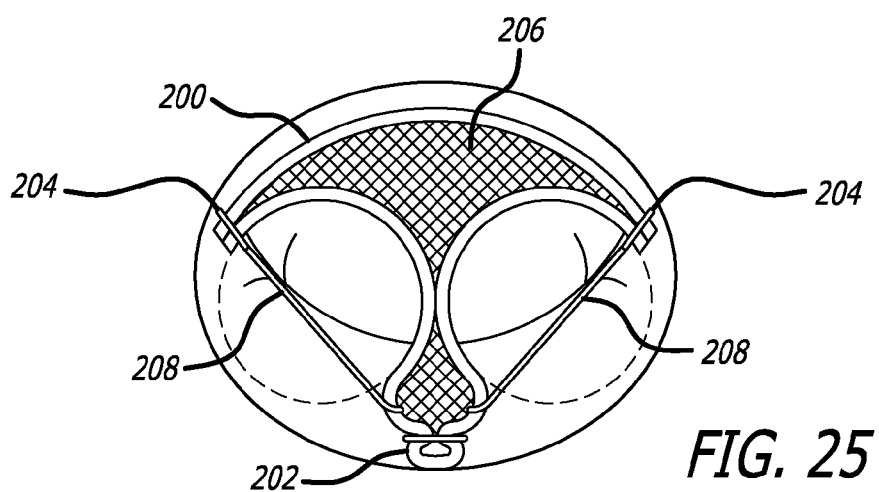
FIG. 25 is a transverse view, depicting yet another anchor structure.

An anchor implant having a generally T-shaped frame 200 is shown in FIG. 24. At a base of the T-frame is a commissural foot 202 configured for P2 attachment, whereas the ends of the T-bar of the frame include commissural feet 204. An expandable web fabric membrane 206 extends between the curvilinear members defining the T-shape frame 200. As shown in FIG. 25, the T-shaped frame 200 can further include a pair of limited elongation flexible cords 208 each extending from the commissural feet 202 at the base of the T-shape frame 200 to one end of the T-bar of the frame.

In yet another approach (FIGS. 26-27), an anchor implant 210 can be embodied in structure designed to prevent turning of an artificial valve attached to the implant 210, and to help in proper seating. Commissural feet 212 are configured as before, that is to reside between and below natural valve commissures. The wire frame of the implant 210 includes further larger loops 214 of varying sizes and angled in a manner to engage anterior and posterior walls of the left atrium to thereby provide lever point support against rotation and structure including the frame from sliding through a valve orifice. Flexible cords 216 are further provided to retain the shape of the large loops during subsequent implantation of a replacement valve.

Bar-like anchors are also contemplated (See FIGS. 28-38). In one approach as shown in FIGS. 28 and 29, the anchor implant 220 can be embodied in a cross-member 222 sized to span a full area of a commissural leaflet. The ends of the cross-member are provided with broad pads 224, a top portion 226 of which covers the commissural leaflet and can act to minimize leaking in this area. A bottom portion 228 of the broad pads 224 can include a projection through a commissural of the leaflet, thus providing an anchor function.

As shown in FIGS. 30-32, the anchor implant 230 can include an intra-annular commissural anchoring frame 232 sized and shaped to receive an artificial valve, or can alternatively be employed to hold another anchor implant in place during a healing and tissue ingrowth stage. Opposite ends of the implant 230 are curved members 234 which are intended to conform to local anatomy, and extend from above the annulus (intra-atrial), through valve commissures, and to within the LV. Texturing or tissue fabric can be associated or configured upon the member 234. The cross-member 236 connecting the ends of the implant 230 also defines a curved member designed to reside in the atrium and further includes a band 238 providing both strain relief and support structure to the cross-member 236.

Figure 33:
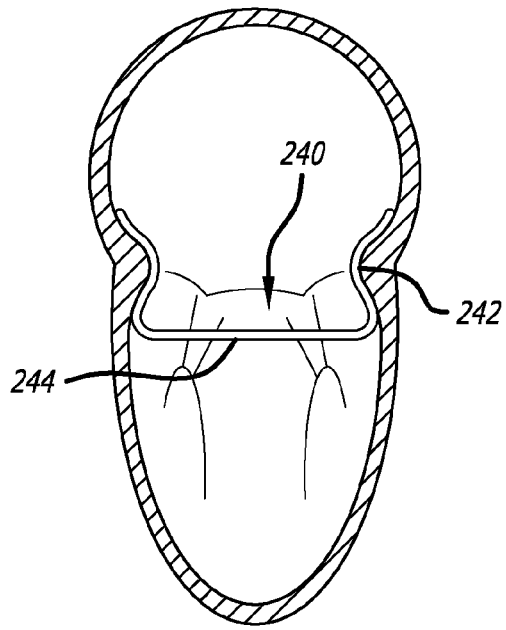
FIG. 33 is a vertical cross-section of the heart looking at the posterior wall of LV, depicting an anchor wire that includes a cross member.
Figure 34:
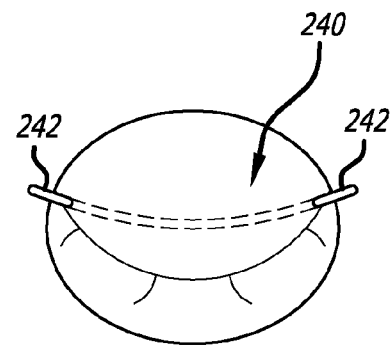
FIG. 34 is a transverse (short axis) cross section of the heart at the mitral valve annular level, depicting the anchor frame of FIG. 33.
Figure 35:
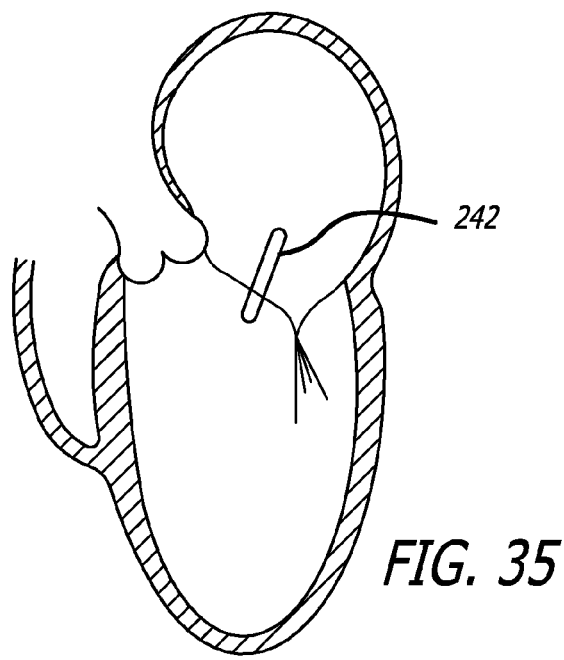
FIG. 35 is a vertical cross section through the aorta and the A2/P2 segment of the mitral valve, showing a view of the anchor frame of FIGS. 33 and 34.
Figure 36:
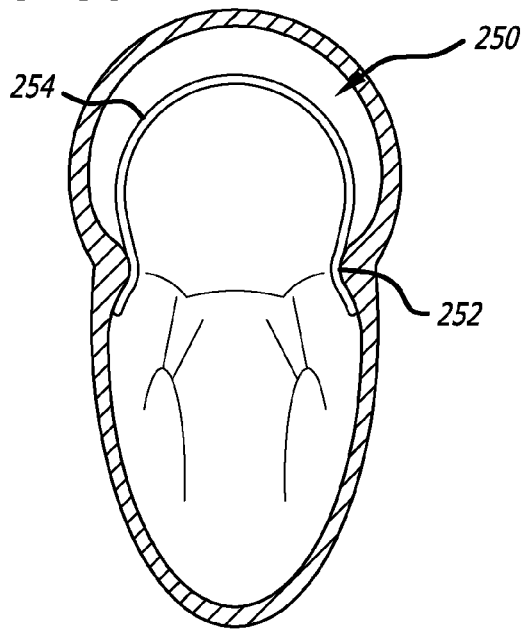
FIG. 36 is a vertical cross-section of the heart looking at the posterior wall of LV, depicting another anchor wire frame.
Figure 37:
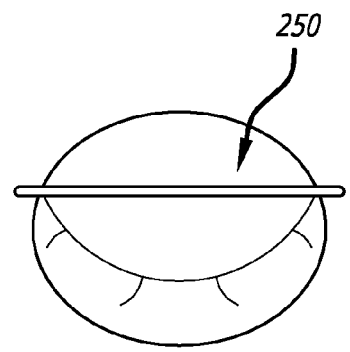
FIG. 37 is a transverse (short axis) cross section of the heart at the mitral valve annular level, depicting the anchor frame of FIG. 36.
Figure 38:
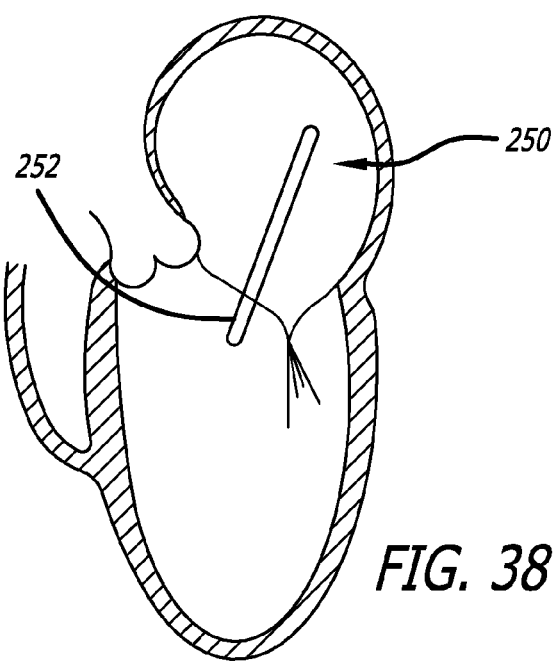
FIG. 38 is a vertical cross section through the aorta and the A2/P2 segment of the mitral valve, showing a view of the anchor frame of FIGS. 36 and 37.

Another anchoring frame 240 is shown in FIGS. 33-35. Here, opposite ends of the implant are curved members 242 which are sized and shaped to conform to local anatomy and extend from above the annulus, through valve commissures, and to within the LV. The cross-member 244 extends from both ends of the curved end members, and thus is intended to reside below valve annulus. Cross member 244 resides between the chordal tent of the anterior leaflet chordae and posterior leaflet chordae with the lateral ends extending between the individual chordae out to the LV wall. Because the cross member 244 is a loop like structure it does not entangle in the chordae, stays between the respective anterior and posterior leaflet chords, and helps orient the cross member parallel to the commissure to commissure line.

In an alternative approach (FIGS. 36-38), a bar-like, anchor frame 250 has a generally omega profile sized to span the heart atrium. The ends of the frame 252 are shaped to conform to anatomy, and also extend through valve commissures. The curved bar 254 connecting the shaped ends is sized and shaped to reside above the valve annulus.

Figure 39:
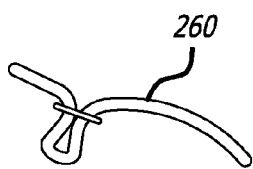
FIG. 39 is a side view, depicting an anchor structure with a saddle shape.
Figure 40:
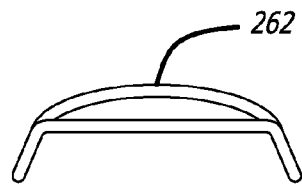
FIG. 40 is a view of an anchor structure that has an arc section.
Figure 41:
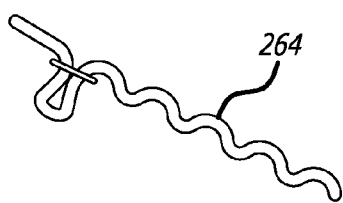
FIG. 41 is a side view, depicting an exemplary anchor structure that has a serpentine wire frame.
Figure 42:
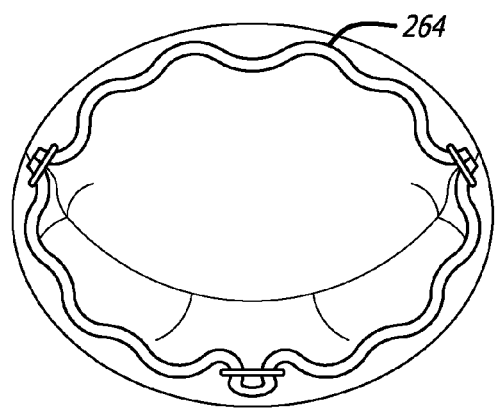
FIG. 42 is a top view, depicting an anchor structure that has a serpentine wire frame.

Moreover, as shown in FIGS. 39-43, it is further contemplated that a ring frame of an anchor implant can reside in multiple planes. That is, the frame can embody a saddle shape 260 configured to accommodate the curvature of a valve annulus such as of the mitral valve (FIG. 39). The frame can further include an arc section 262 configured to accommodate the curvature of the inter-trigone anterior leaflet (See FIG. 40). Moreover, the anchor frame can include a serpentine shape 264 (FIG. 41) intended to accommodate dimensional and shape variations of the native annulus. The curves of the serpentine pattern can be perpendicular to the native annulus as shown in FIG. 41, or they can extend horizontally with respect to the annulus as shown in FIG. 42, or of course a combined approach to undulations may be desirable.

Figure 43:
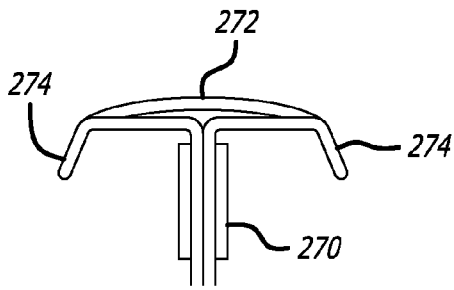
FIG. 43 is a cross-sectional view, depicting an adjustable anchor wire frame.

With reference to FIG. 43, it is also contemplated that a wire frame anchor implant can include adjustable substructure for accommodating perimeter variations of a valve annulus. Here, a delivery tube 270 can be configured to advance or retract sections of a wire implant to best fit it to anatomy. Excess length would be severed and removed. In one approach, lengths of posterior frame wire can be so adjusted, leaving unchanged an anterior frame portion 272, and commissural extension 274. Other areas of an anchor implant can also be likewise adjusted as desired.

Figures 44, 45A:
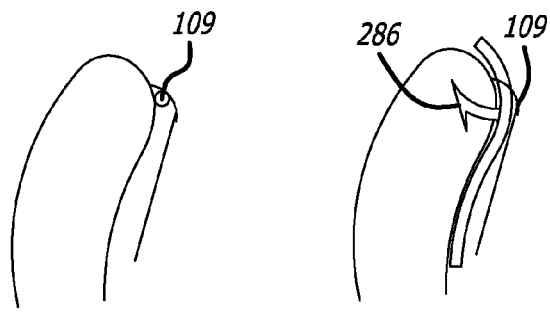
FIG. 44 is a section view of the commissural region, depicting structure for direct mechanical load support of the anchor.
FIG. 45A depicts a section view at the region of the fibrous trigone structure to provide direct mechanical load support to an anchor.
Figure 45B:
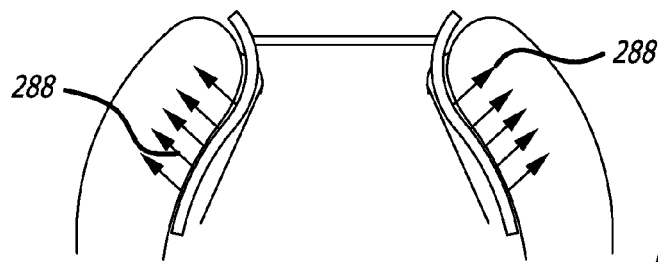
FIG. 45B depicts an anchor structure to create a dimensional interference.
Figure 46:
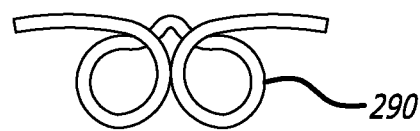
FIG. 46 is a partial section view, depicting the deployed configuration of an anchor.
Figure 47:
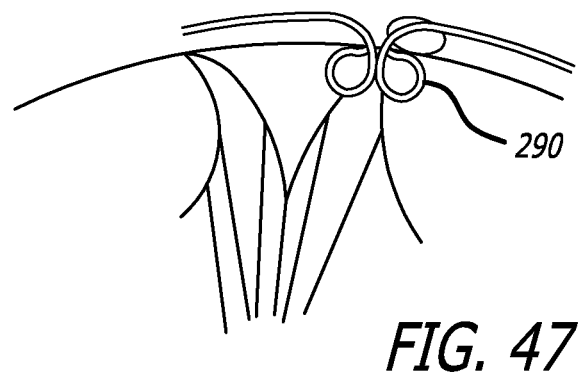
FIG. 47 is a side view, depicting the anchor of FIG. 46.
Figure 48:
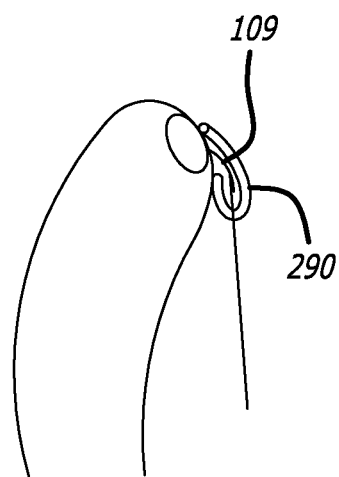
FIG. 48 is a section view, depicting the anchor of FIGS. 46 and 47.
Figure 49:
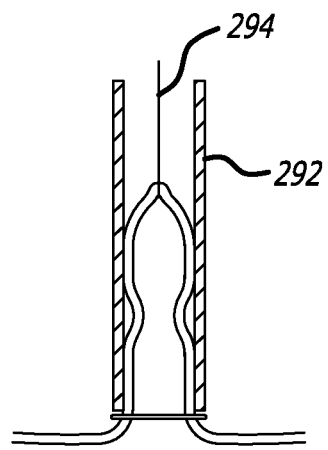
FIG. 49 is a cross-sectional view, depicting the anchor of FIGS. 46-48 in a predeployed state.

Next, various approaches to anchor attachments are presented. As shown in FIG. 44, a direct mechanical load can be placed behind a leaflet 109 to provide structural support to an anchor. As previously stated, it is further contemplated that the robust anatomy of collagen annulus or a trigone can be relied upon to receive piercing anchors (See FIGS. 45A-45B) such as fish-hook 286 or arrowhead-like 288 structure. It has been found that muscle attachment provides excellent ingrowth for stable long term anchoring. Shear loading is depicted in FIG. 45C and deeper (FIG. 45D), wider (FIG. 45E) and longer areas (FIG. 45F) of anchor penetration are also contemplated. By taking one or more of these approaches, desired and increased holding capability is achieved.

As shown in FIGS. 46-49, one specific approach to a commissural projection of an anchor implant can assume a pair of loops 290. Such loops are intended to be sized so that they can reside under and behind a leaflet 109. Moreover, it is contemplated that the anchor projection be made from flexible and elastic material and be able to be inserted in a straightened configuration within a delivery tube 292. A delivery tube 292 can be employed for each anchor projection 290, and a connection delivery wire 294 is further provided to control positioning. Thus, the delivery wire 294 can be withdrawn or otherwise disengaged from the anchor projection 290, and to thereby permit release to be reconfigured into its looped configuration. This can be done either before or after ejection from the anchor projection 290 from within the delivery tube 292. Moreover, individual, releasable control is provided by employing a delivery wire approach. That is, through multiple connections of a plurality of delivery wires to an anchor, desirable control is facilitated. Catheter/tube access or over-the-wire access approaches are also contemplated for providing in situ access to each anchoring location to deploy both anchor portions and tissue penetrating structures.

Figure 50:
FIG. 50 depicts a deployed leaflet clip.
Figure 51:
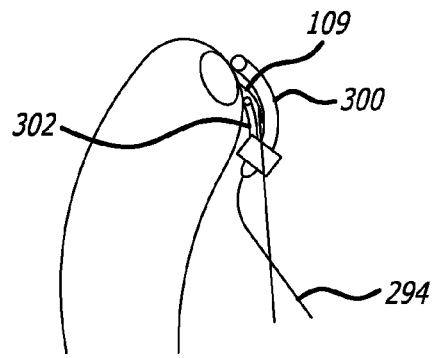
FIG. 51 is a section view, depicting the deployed leaflet clip of FIG. 50.

As shown in FIGS. 50 and 51, the anchor projection 30 can also include a leaflet clip configuration 302 attached to its terminal end. The clip 302 can also be delivered as described above using a delivery tube and connection delivery wire 294, so that it is properly positioned, such as behind a leaflet 109. A flat terminal end 304 of the clip 302 presents the valve anatomy with an atraumatic surface, as well as a robust engagement.

Figure 52:
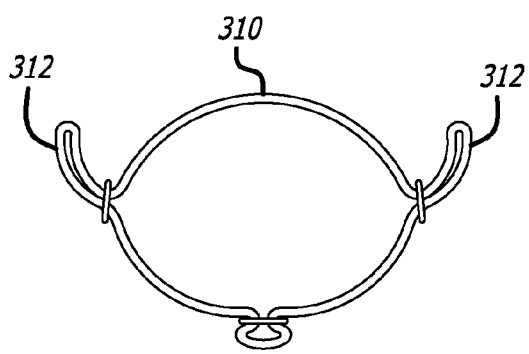
FIG. 52 is a top view, depicting an anchor structure for attachment to the fibrous region of the trigone.
Figure 53:
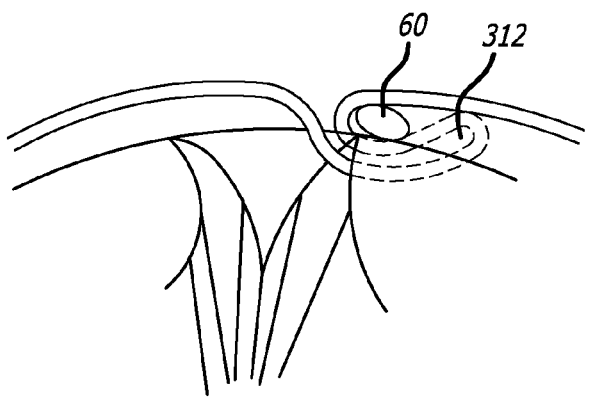
FIG. 53 is a side view of the mitral annulus, depicting a portion of the anchor structure of FIG. 52.
Figure 54:
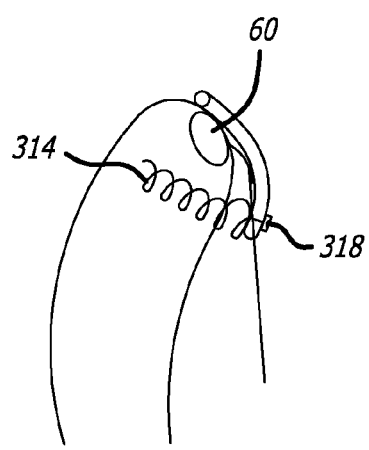
FIG. 54 shows a penetrating anchor securement element that utilizes a helical screw.

In another approach (FIGS. 52-53), an anchor implant 310 can include commissural projections 312 that extend down and anteriorly to hook under the fibrous region of the trigone 60, and beyond the annulus. A penetrating securement element in the form of a helical screw 314 (See FIG. 54) can be further deployed through a loop presented by the commissural projections 312 to further seat and securely attach the anchor implant 310 in place. It is noted that a proximal winding 316 of the helical fastener 314 can have a larger profile for positioning on an outside wall of local anatomy (such as the LV wall). A terminal end 318 of the helical element is sized to retain the structures into engagement.

Figure 55:
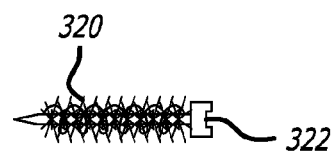
FIG. 55 shows a penetrating anchor securement element that utilizes a wire brush.
Figure 56:
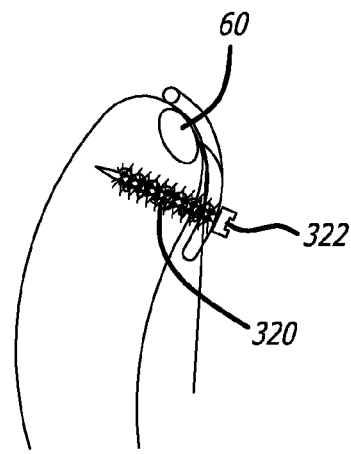
FIG. 56 shows the securement element of FIG. 55 in position in a section view of the mitral annulus.
Figure 57:
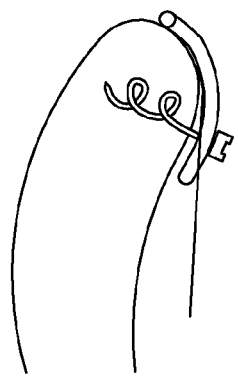
FIG. 57 shows a penetrating anchor securement element that utilizes a helical screw.
Figure 58:
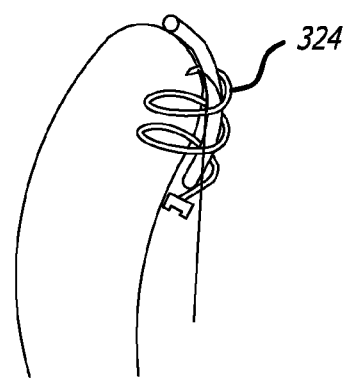
FIG. 58 shows an exemplary penetrating anchor securement element.
Figure 59:
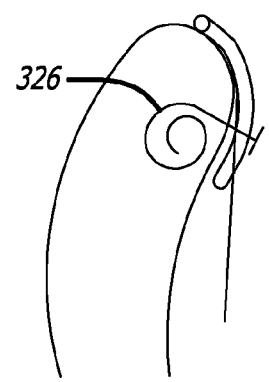
FIG. 59 shows another penetrating anchor securement element.
Figure 60:
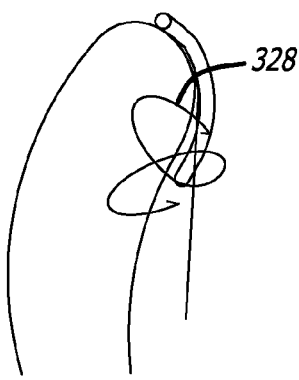
FIG. 60 shows yet another penetrating anchor securement element.
Figure 61:
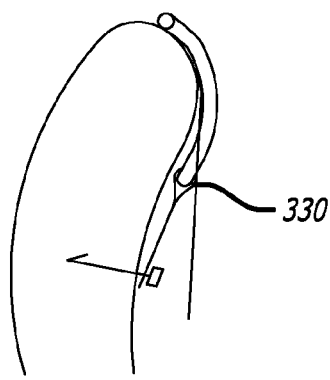
FIG. 61 shows a generic penetrating securement element that is placed in a position further down into the LV.

Other approaches to fasteners are also contemplated (FIGS. 55-61). As shown in FIGS. 55-56, one device can embody a fastener with a wire brush body 320 and a nail head terminal end 322 as retaining structure. Other approaches involving a variable coil (FIG. 57), a longitudinally directed coil 324 (FIG. 58) configured parallel to a commissural projection, or a curved penetrating ribbon securement markers 326, 328 (FIGS. 59-60) can also be useful approaches to providing secure retention of parts against anatomy. Moreover, a commissural projection 330 (FIG. 61) can be equipped with a cord extension through which a penetration securement element 332 can be inserted and advanced into body anatomy to accomplish a necessary attachment function.

It is intended that approaches to sealing may need to provide a contiguous seal between the overall implant (including the implanted replacement valve) and the native valve tissue/structures to prevent regurgitant para-valvular flow. Additionally, contemplated sealing configurations are intended to provide for tissue engagement and stable incorporation at the tissue and sealing structure interface. These sealing structures may also provide a staged interface to accommodate alternative type valve implant systems, such as the dual parallel valve approaches where the geometry for valve interface is not the native annulus or the anchor implant structure. Sealing structures may include a frame portion, made of metal or other suitable material in a wire or laser cut configuration. The frame may be covered with a material to promote tissue ingrowth. Additionally or alternatively, the sealing structure may utilize an expandable member. The expandable member can be balloon inflation, a self-expanding metal frame from a compressed delivered state, or a self-expanding material such as foam or a hydrogel. The expanding member may be used to directly form the seal or it may be used as a deployment mechanism of another structure. Besides using the direct tissue engagement forces designed into the structure and or deployment of the valve assembly, the system can exploit the pressurization of the LV during systole to create the forces needed to seal between the valve assembly and the tissue.

As previously noted, the seal may be incorporated into the anchor itself, incorporated into the valve, or may be a separate structure. Incorporation of the tissue sealing mechanism onto the anchor assembly can either be achieved acutely or utilize the chronic ingrowth of the anchor into the tissue to generate a seal allowing for a secondary seal between the valve and the anchor during its deployment. The secondary seal can utilize the stability and consistency of the anchor structure to complete the overall seal for the complete valve assembly.

In the situation where the tissue seal is incorporated onto a valve/occluder assembly, the anchor structure is primarily utilized to provide the load bearing function Where a separate implant structure creates substrate for sealing, the implant engages the anchor and valve and the seal is created by one of the following; sealing directly to the tissue around the anchor implant creating the primary tissue seal with a secondary seal to the valve, sealing to the anchor and the valve as secondary seals with the anchor as the primary tissue seal, or structurally bridging the anchor to the valve where the valve creates the primary tissue seal.

Furthermore, to develop an acute seal between the native tissue and the specific element of the overall valve assembly, direct force between the valve assembly and the tissue can be used. Alternatively, the pressurization of the LV during ventricular systole can be used to "inflate" or pressurize an element on the valve assembly such that it engages the native tissue to create a seal.

In one approach, for the interface between the anchor and the tissue, simple surface contact between the surfaces can facilitate sealing through tissue ingrowth. Additionally the anchor skeleton can provide an expansion force to create a compressive interface. In certain embodiments of the anchor, dilatory or pinching like forces can be created at certain regions of the anchor.

Mechanisms to create engagement between the anchor and valve can include balloon expansion of valve frame into anchor structure, or self-expansion of valve frame into anchor structures. Additionally, a hook-like engagement where the valve frame clasps or hooks onto anchor or anchor and tissue can be used as can a frictional fit between the structures, the same being created via balloon or self-expansion of the valve frame into the anchor. Interlock mechanisms where the valve frame engages the anchor ring can be employed as can conformable balloon or material interface.

For a tissue/valve interface, dilation of the valve or valve frame elements can be utilized. Also contemplated is a simple surface contact to facilitate ingrowth of tissue onto valve structures, compression and expansion elements on the valve frame for directly engaging the tissue, inflation of a valve structure via the LV pressure, and then deployment of hooks or structural frame elements enhance or create tissue engagement. It is further noted that the various sealing structures disclosed can be adapted to either be part of the anchor structure, part of the valve structure, or be an independently delivered structure. Moreover, all disclosed features can be utilized individually or in any combination. Surface composition elements, specifically material choice and texture to promote tissue reaction and device incorporation with maximal sealing capability, may have a significant impact on sealing capabilities. Specific sealing modifications can include surface texture (pores to promote ingrowth and mechanical hold), material choice (Dacron velour, double velour, ePTFE), abrasive surfaces, and/or a chemical irritant to promote inflammatory response. Further, tissue surface modification can involve abrasive chemical irritant to promote inflammatory response, and the use of heat.

Figure 62:
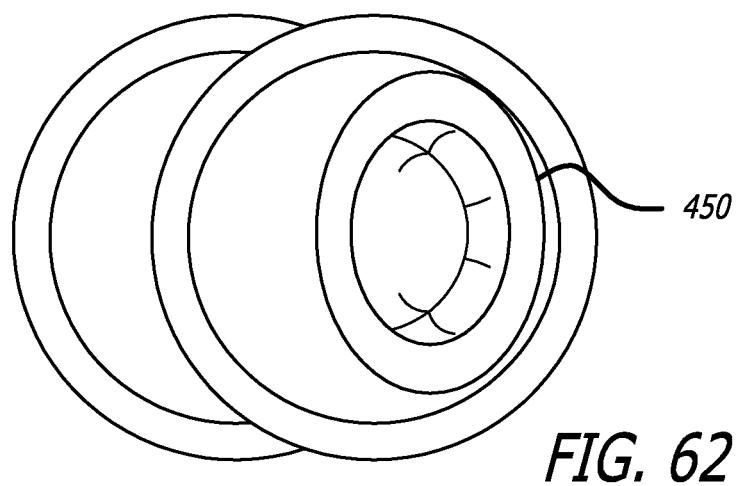
FIG. 62 is a transverse (short axis) cross section view of the heart at the mitral valve annular level, depicting an embodiment of a circular anchor structure.
Figure 63:
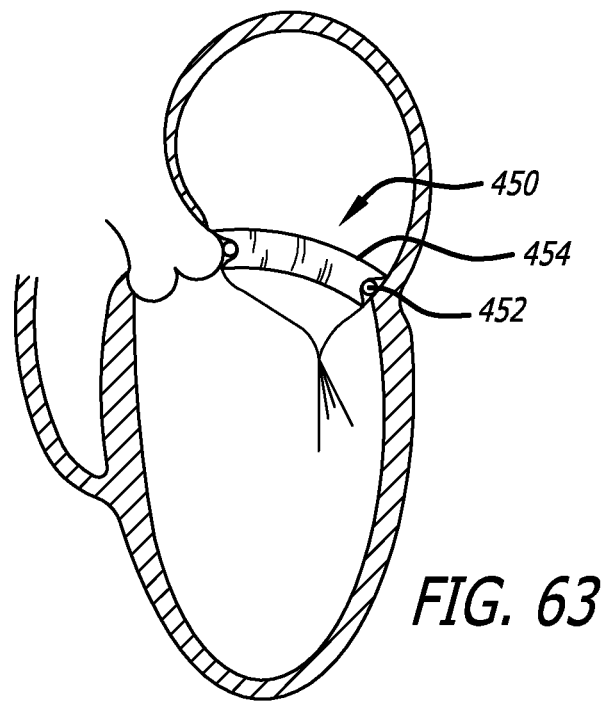
FIG. 63 is a vertical cross section through the aorta and the A2/P2 segment of the mitral valve, depicting the structure of FIG. 62.
Figure 64:
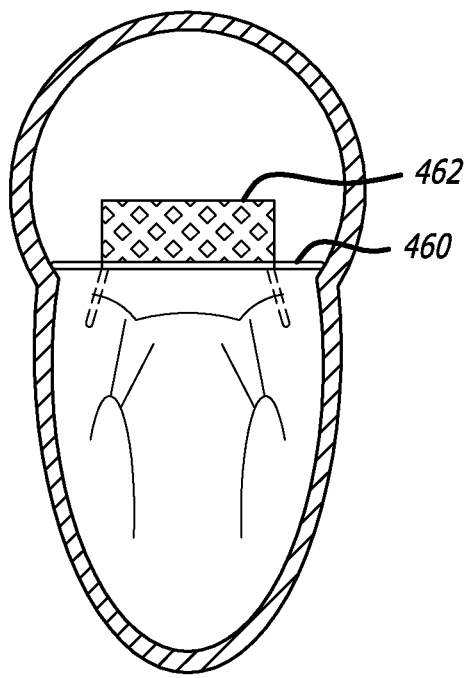
FIG. 64 is a vertical cross section of the heart looking at the posterior wall of LV and the mitral valve, depicting an embodiment of a sealing skirt structure.
Figure 65:
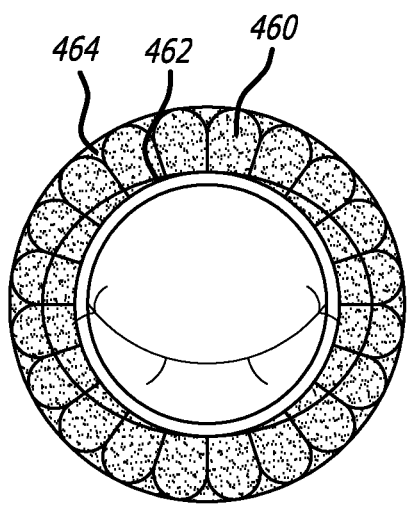
FIG. 65 is a transverse (short axis) cross section of the heart at the mitral valve annular level, depicting the sealing skirt of FIG. 64.
Figure 66:
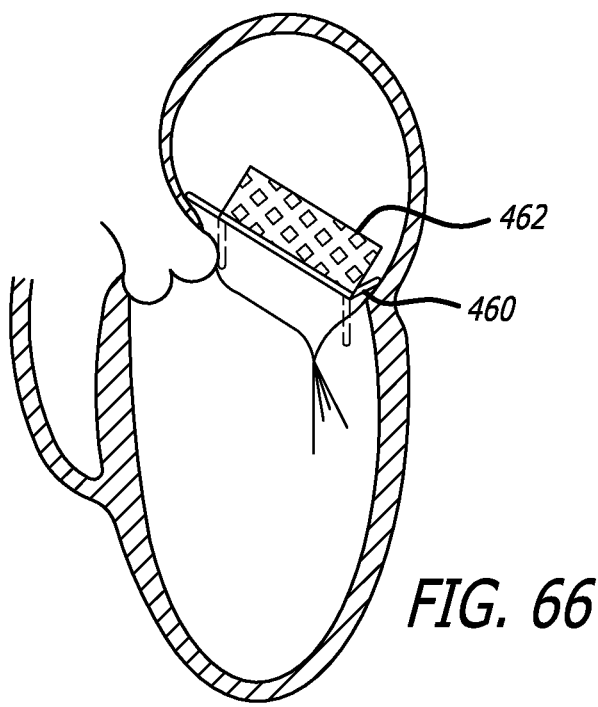
FIG. 66 is a vertical cross section through the aorta and the A2/P2 segment of the mitral valve, depicting the sealing skirt of FIGS. 64 and 65.

Accordingly, as shown in FIGS. 62 and 63, an anchor implant 450 can include an internal ring 452 surrounded by a covering 454 adapted for tissue ingrowth. As stated, tissue ingrowth cooperates with the engagement of the anchor implant 410 to create a seal against heart tissue. As before, the anchor implant is sized and shaped to fit the heart valve annulus.

Figure 67:
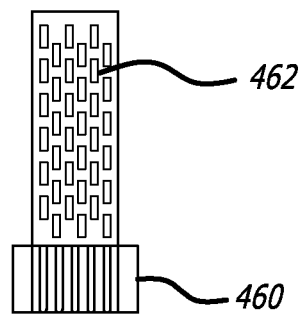
FIG. 67 is a collapsed view of the valve and sealing skirt of FIGS. 64 and 65.
Figure 68:
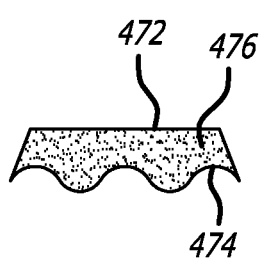
FIG. 68 is a side view, depicting an embodiment of a sealing structure.
Figure 69:
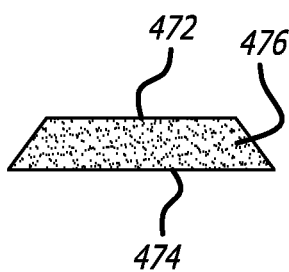
FIG. 69 is a side view of a sealing structure of FIG. 68.
Figure 70:
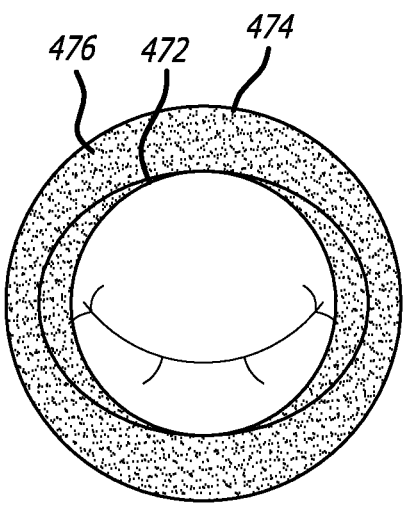
FIG. 70 is a transverse (short axis) cross section of the heart at the mitral valve annular level, depicting the sealing structure of FIG. 69.
Figure 71:
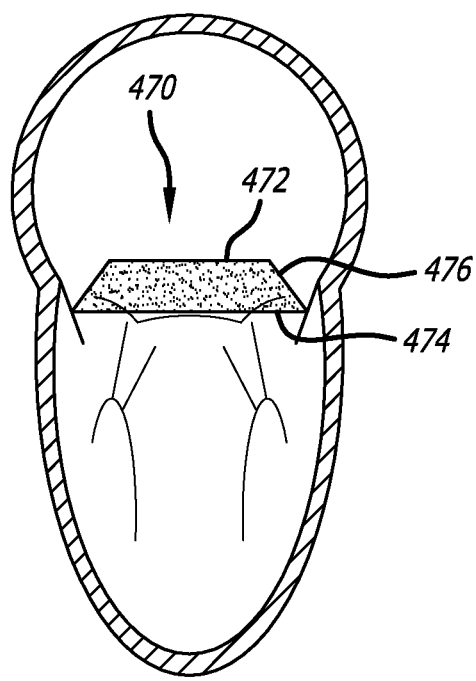
FIG. 71 is a vertical cross section looking at the posterior wall of LV and the mitral valve, depicting the sealing structure of FIGS. 69 and 70.
Figure 72:
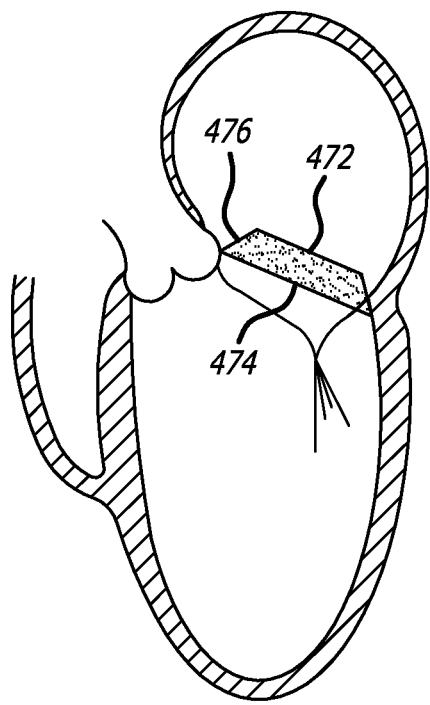
FIG. 72 is a vertical cross section through the aorta and the A2/P2 segment of the mitral valve, depicting the sealing structure of FIGS. 69 and 70.

Sealing can also be accomplished by employing petals 460 arranged about a circumference of an expandable frame 462 (See FIGS. 64-67). As shown in FIG. 67, the valve assembly can assume a compressed configuration for delivery and then expanded upon implantation. Selected such petals 460 can be arranged to engage a valve annulus or alternatively can be configured to engage the leaflets themselves. A foldable fabric 464 can further be provided about the petals to facilitate sealing and a continuous engagement about a perimeter of a valve.

As shown in FIGS. 68-72, an expandable ventricular ring 470 can also be used to accomplish desired sealing. Here, a pair of longitudinally spaced circular frames 472, 474 support a fabric covering 476. The lower frame 474 expands outwardly to engage tissue and provide the sealing function against tissue. It is contemplated that the first frame 472 resides above the valve annulus and the second frame 474 engages anatomy below the annulus. In this situation, the seal between the native tissue/leaflet with frame 474 is facilitated by the LV pressurization of the internal surface of the frame 474 and fabric 476 as well as the underside of the leaflets pushing the tissue and frame 474 against each other.

Figure 73:
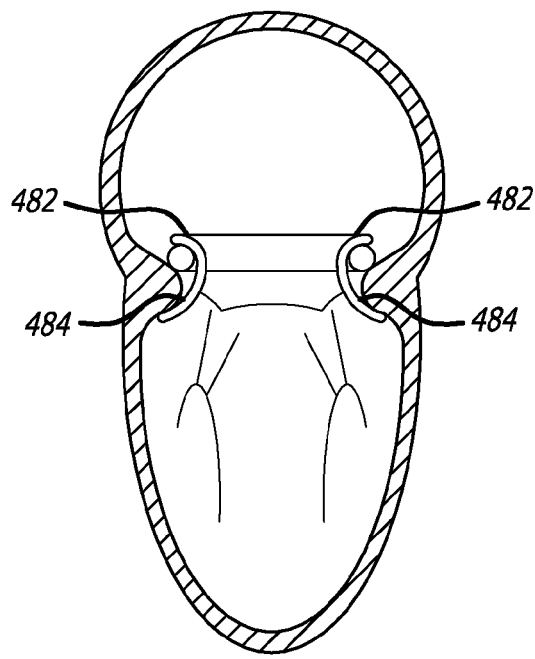
FIG. 73 is a vertical cross section looking at the posterior wall of LV and the mitral valve, depicting an embodiment of a sealing structure that has a frame.
Figure 74:
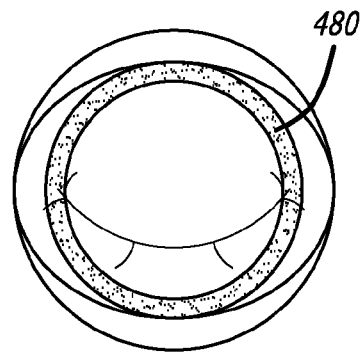
FIG. 74 is a transverse (short axis) cross section of the heart at the mitral valve annular level, depicting the sealing structure of FIG. 73.
Figure 75:
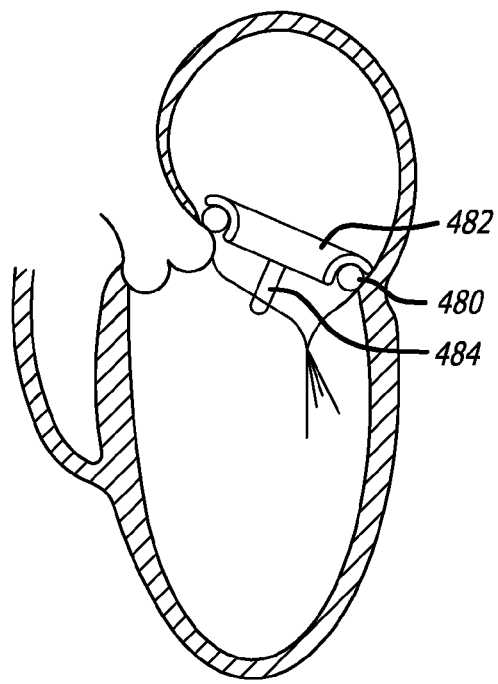
FIG. 75 is a vertical cross section through the aorta and the A2/P2 segment of the mitral valve, depicting the sealing structure of FIGS. 73 and 74.

With reference to FIGS. 73-75, a fluid filled balloon 480 can also be incorporated into sealing structure. The balloon 480 can define a ring-shaped structure which when expanded engages and seals against varying heart anatomy. The assembly can further include commissural engagement anchors 482, the same being defined by a wire frame. A downwardly projecting frame 484 can also be included to aid in absorbing forces tending rotate the assembly when implanted at the native valve.

Figure 76:
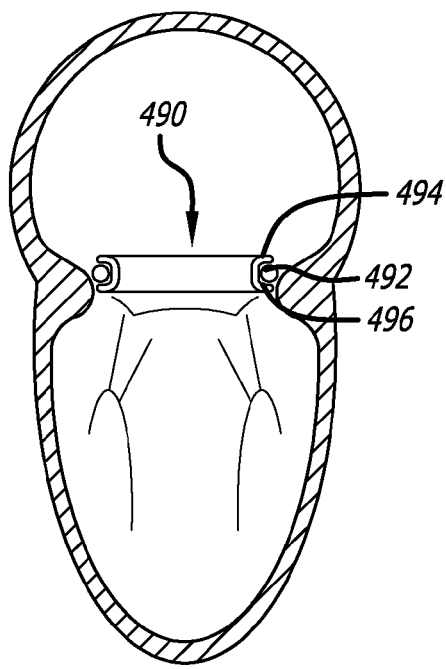
FIG. 76 is a vertical cross section looking at the posterior wall of LV and the mitral valve, depicting another embodiment of a sealing structure.
Figure 77:
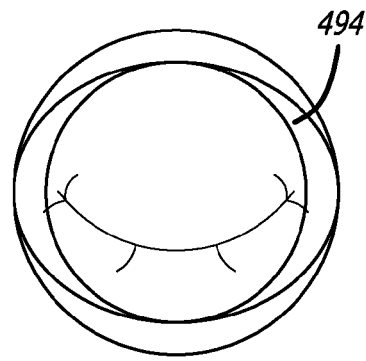
FIG. 77 is a transverse (short axis) cross section of the heart at the mitral valve annular level, depicting the sealing structure of FIG. 76.
Figure 78:
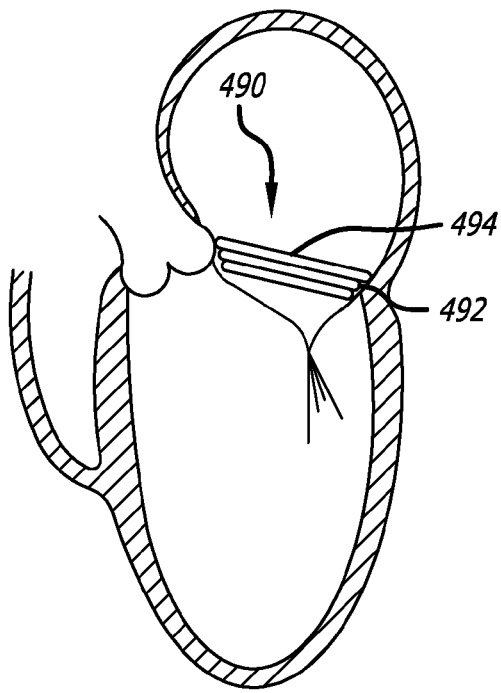
FIG. 78 is a vertical cross section through the aorta and the A2/P2 segment of the mitral valve, depicting the sealing structure of FIGS. 76 and 77.
Figure 79:
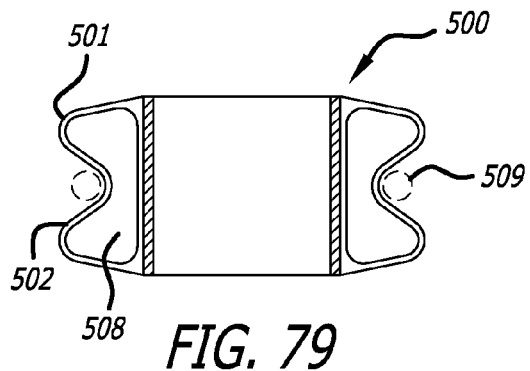
FIG. 79 is a cross-sectional view, depicting the sealing structure of FIG. 76.
Figure 80:
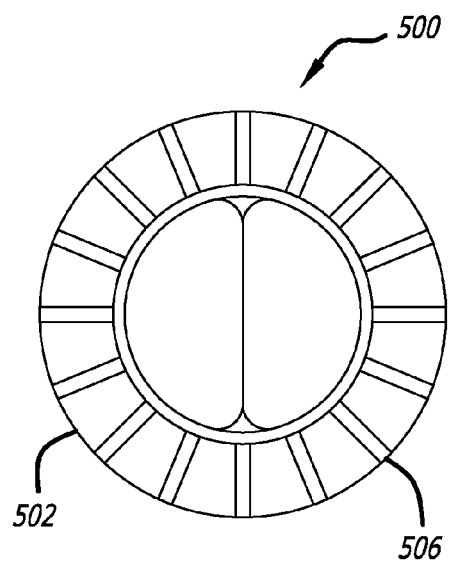
FIG. 80 is a top view of the exemplary assembly of FIG. 79 showing the bi-leaflet valve.
Figure 81:
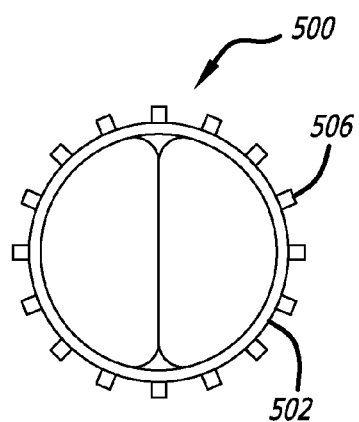
FIG. 81 is a top view, depicting the assembly of FIG. 80.
Figure 82:
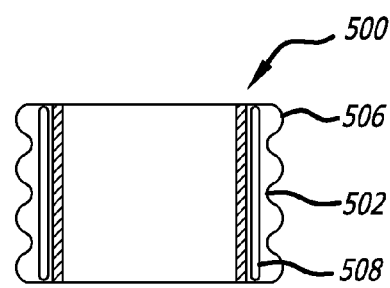
FIG. 82 is a cross section, depicting the structure of FIG. 81.

With reference to FIGS. 76-78, a sealing assembly 490 can also embody an anchor ring 492 partially enclosed by a ring balloon 494. The anchor ring 492 engages tissue at the valve annulus and the circular balloon 494 forms a "C" about the anchor ring 492 when viewed in cross-section, thereby presenting two additional contact points with anatomy about the perimeter of a valve. Such structure provides a seal between the assembly and heart anatomy as well as between the anchor ring 492 and ring balloon 494 through an interlocking engagement. A circular band 496 placed at the junction between the balloon 494 and anchor ring 492 can limit expansion of the balloon 494 and facilitate its surrounding the anchor ring 492.

As shown in FIGS. 79-82, a sealing assembly 500 can alternatively embody a circular frame 502 including a plurality of vertically arranged, expandable wire struts 504 spaced about a periphery of the frame 502. Configured between a central frame structure 506 and the expandable struts 502 is an expandable circular balloon 508. Upon expansion of the balloon 508, the expandable struts 504 expand outwardly and thus can engage and bend around an anchor implant 509 placed at the interventional site. Such bending forces created by the expanded balloon operate to seal the assembly 500 against the anchor 509 and valve anatomy.

Figure 83:
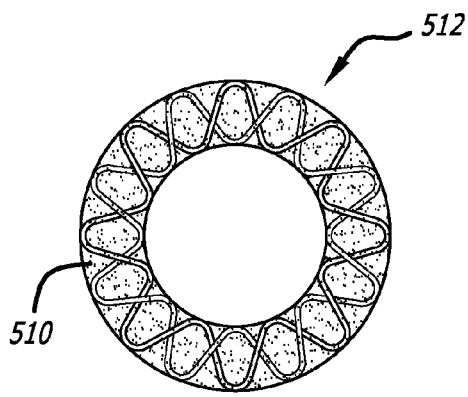
FIG. 83 is a top view, depicting a sealing structure frame with fabric covered wire mesh.
Figure 84:
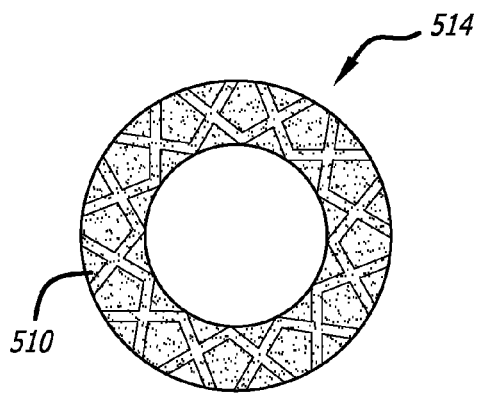
FIG. 84 is a top view, depicting an expandable metal mesh sealing structure.

FIGS. 83 and 84 depict an additional two approaches to sealing structures. In each, a frame is contoured with a fabric covering 510. The frame can be formed from a wire mesh 512 (FIG. 83) or can be defined by an expandable metal frame 514 (FIG. 84). Again, such structure is intended to sealingly engage within heart anatomy and when desired, about an anchor implant.

Figure 85:
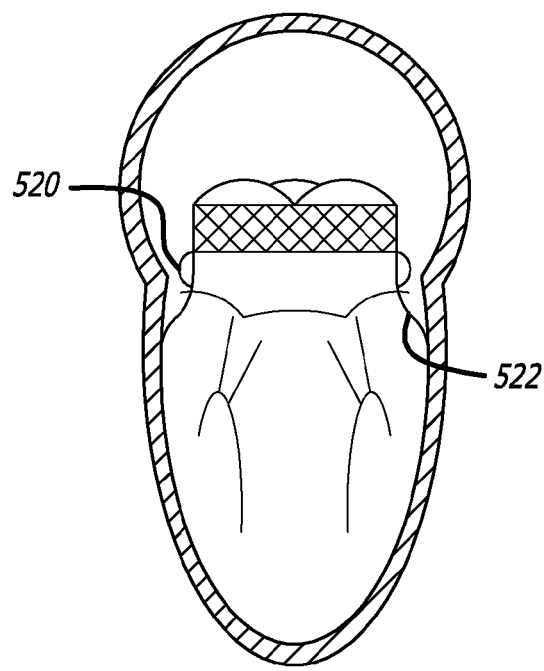
FIG. 85 is a vertical cross section looking at the posterior wall of LV and the mitral valve, depicting a sealing structure that has a flexible sealing skirt.
Figure 86:
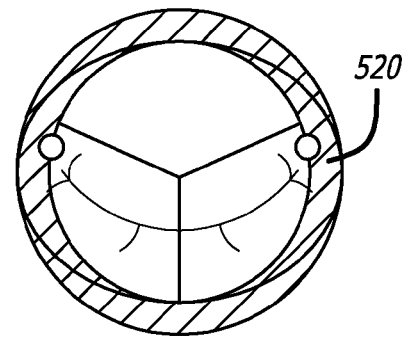
FIG. 86 is a transverse view at the mitral level, depicting the sealing structure of FIG. 85.
Figure 87:
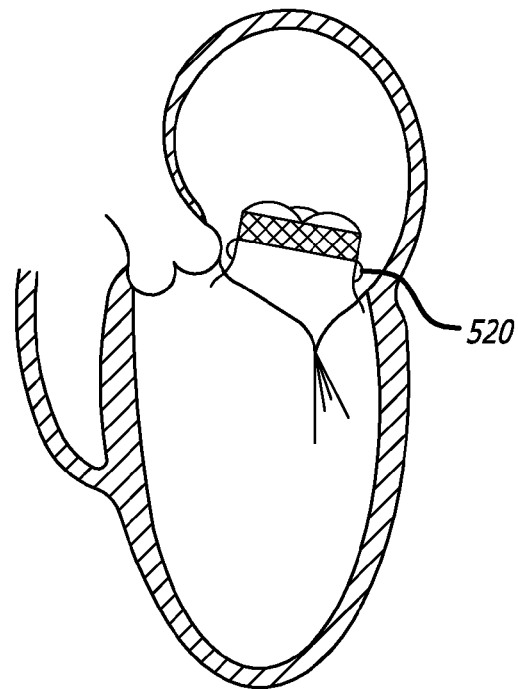
FIG. 87 is a section view of the sealing structure of FIG. 85 in a vertical cross section through the aorta and the A2/P2 segment of the mitral valve.

Moreover, as shown in FIGS. 85-87, sealing can be created by a flexible polyester skirt 520 which expands outwardly in response to pressures within the heart. The expandable skirt 520 can be configured about an extremity of a frame of a heart valve that is additionally supported by commissural anchors 522 extending to within the LV. Over time, tissue over growth covers the skirt 520 providing further attachment and sealing.

Figure 93:
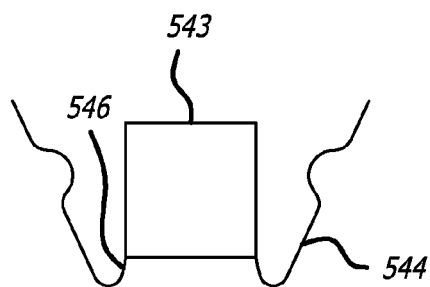
FIG. 93 is an alternative profile to the cross section of FIG. 92.
Figure 94:
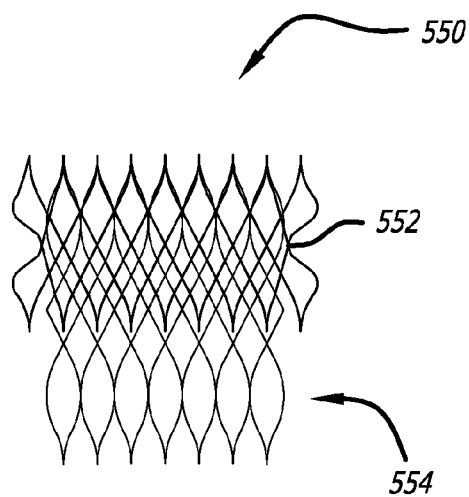
FIG. 94 is a side view, depicting sealing structure in the form of a folded and balloon expanded metal frame.
Figure 95:
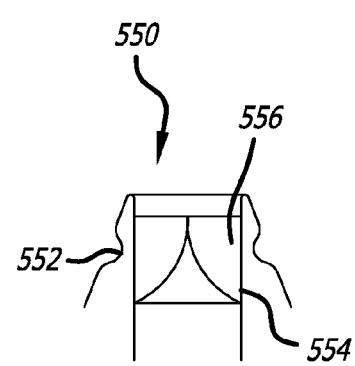
FIG. 95 is a cross-sectional view, depicting the device of FIG. 93.
Figure 96:
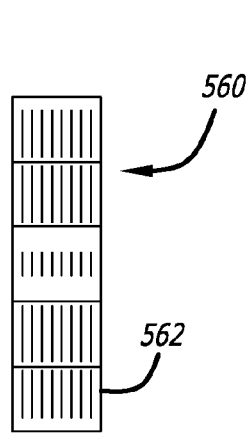
FIG. 96 is a side view, depicting an embodiment of an anchor/valve engagement structure comprising a slotted tubular metal frame.
Figure 97:
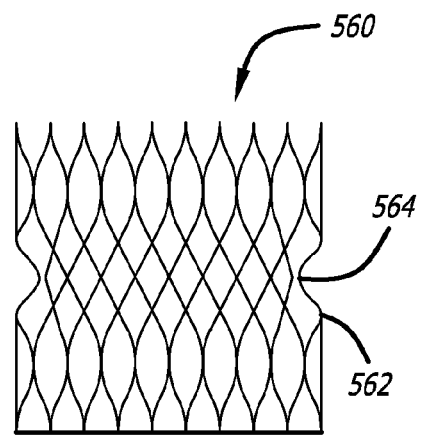
FIG. 97 is a side view, depicting the frame of FIG. 96.
Figure 98:
FIG. 98 is a side view, depicting a slotted tubular metal frame.
Figure 99:
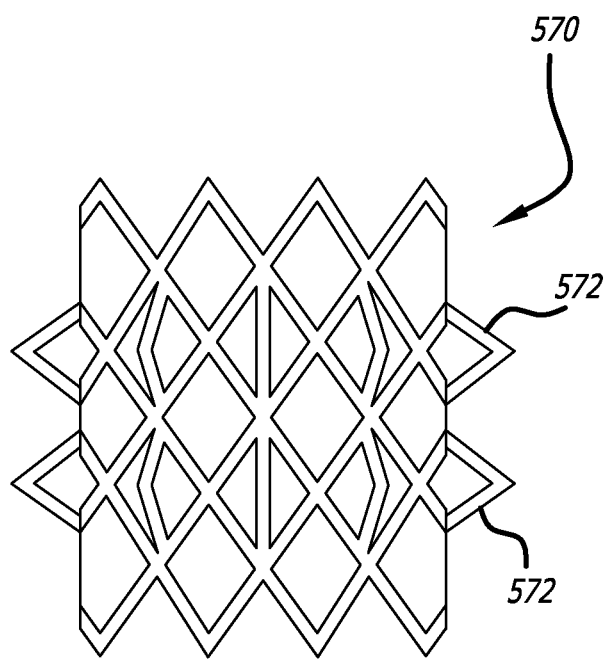
FIG. 99 is a side view, depicting the anchor engagement structure of FIG. 98.
Figure 100:
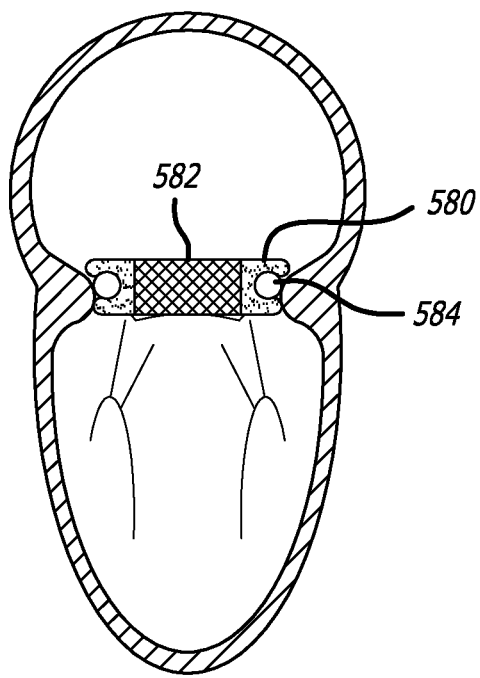
FIG. 100 is a sectional view of the heart, depicting showing an embodiment of a mitral valve replacement system.

Various approaches to expandable strut structure are also contemplated for use as sealing structures (See FIGS. 88-100). In a first approach (FIGS. 88-90), an expandable frame 530 can include a plurality of rows of cells, a middle row of cells include members which expand outwardly to engage an anchor implant 532 about a periphery of an annulus. In another approach (FIGS. 91-93), a sealing frame 540 is embodied in a braided and folded wire mesh structure. An internal portion of the fold 542 attaches to a valve structure 543, whereas a portion of an outer section 544 of the folded wire mesh engages and forms about an anchor implant frame 546. In yet another approach, the sealing frame can be defined by folded metal wire forming structure 550 including indented geometry 552 for engaging an anchor frame 554 and an inner layer which can support valve leaflets 556 (See FIGS. 94-95). Other expandable frame designs are shown in FIGS. 96-99. One such design 560 (FIGS. 96-97) embodies a frame 562 which expands into a tubular shape with a mid-level indentation 564 formed by smaller slits and sized to engage an anchor implant, and a second design 570 (FIGS. 98-99) expands into a tube with a series of upper and lower projections 572 spaced longitudinally providing a space to receive an anchor.

Figure 101:
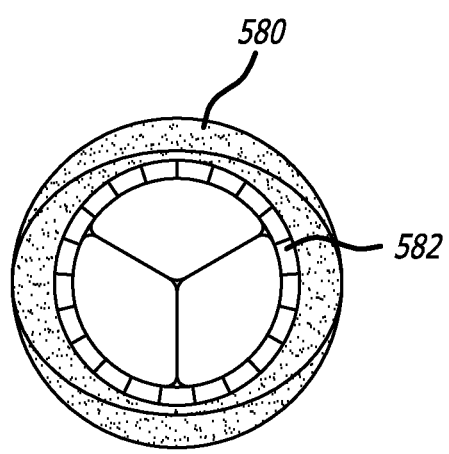
FIG. 101 is a top view, depicting the system of FIG. 100.
Figure 102:
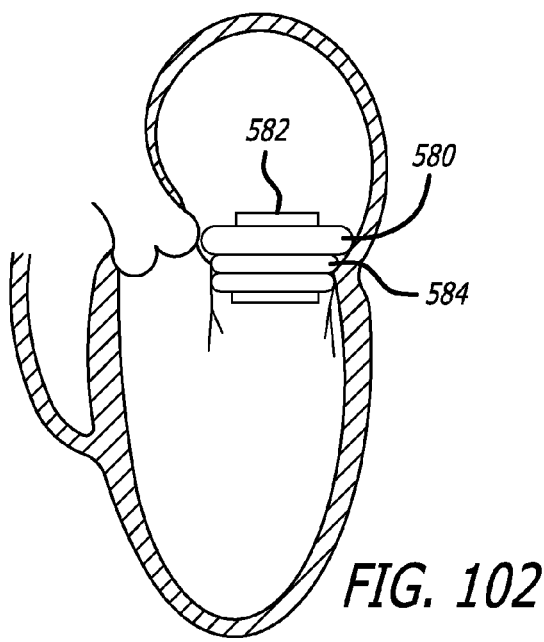
FIG. 102 is a section view with the heart in a cross section along the aorta and A2/P2 section of the mitral valve, depicting the structure of FIGS. 100 and 101.

In still yet another approach (FIGS. 100-102) a compressible material 580 can be employed to create or facilitate sealing. The compressible material can define a ring structure about a valve 582 and placed into engagement with an anchor 584. The compressible material can be made from a foam or hydrogel and thus act as an interlocking element.

Figure 103:
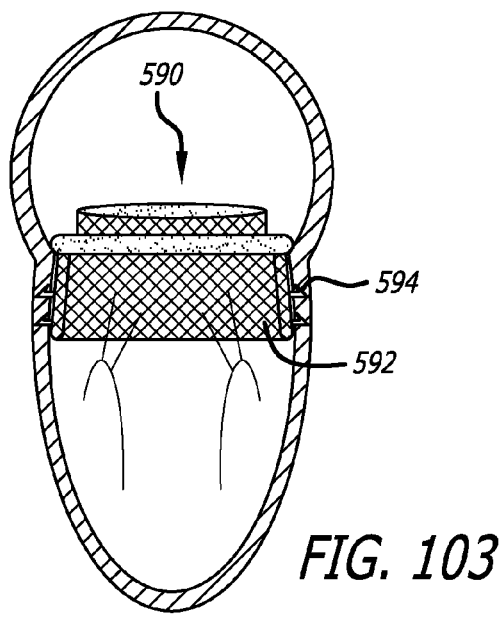
FIG. 103 is a cross-section view, depicting a structural relationship of an expanded valve and an anchor.
Figure 104:
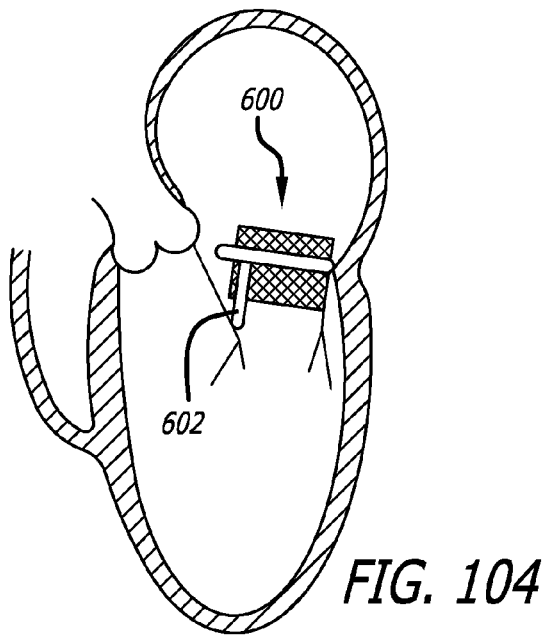
FIG. 104 is a side view, depicting a valve replacement system including a valve.
Figure 105:
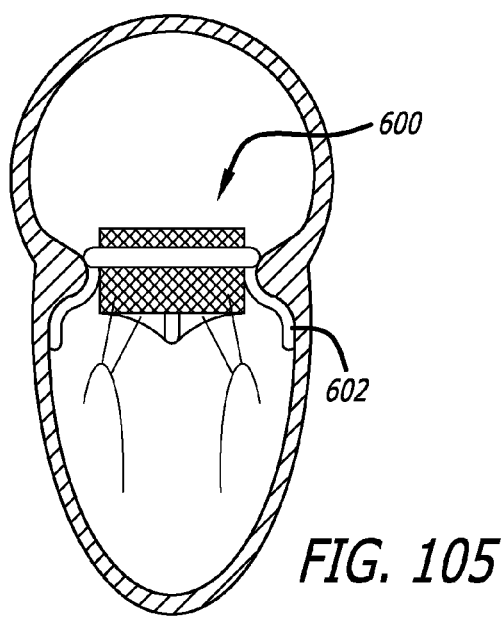
FIG. 105 is the view of the posterior wall of the valve, depicting the system of FIG. 104.
Figure 106:
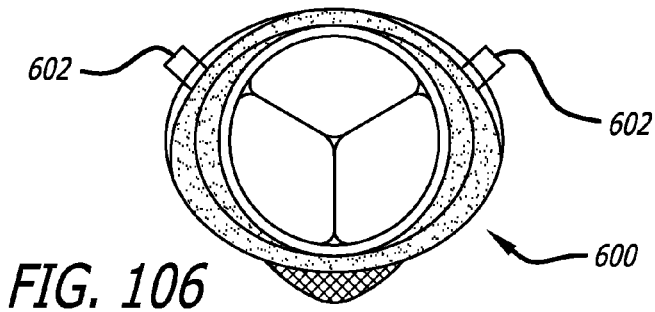
FIG. 106 is a top view, depicting the exemplary system of FIGS. 104 and 105.
Figure 107:
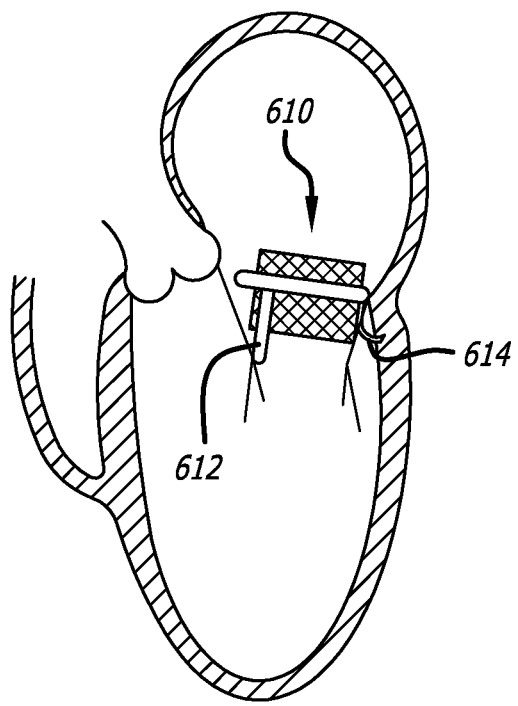
FIG. 107 shows a cross-sectional view, depicting an alternative embodiment for anchoring the system of FIG. 104.
Figure 108:
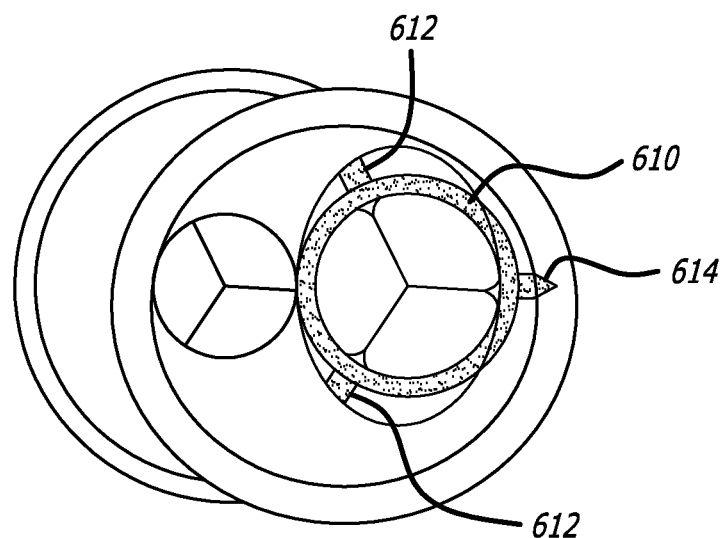
FIG. 108 is a top view, depicting the valve and hook structure of FIG. 107.

Additionally, the sealing device can be embodied in a ring 590 including commissural projections 592 including barbs 594 (FIG. 103). Placement of a valve assembly with the ring 590 helps maintain the barbs 594 in place. Moreover, a sealing ring 600 can conform about and beyond the annulus and between papillary muscles and cooperate with projections 602 extending from an anchor to accomplish secure implantation (See FIGS. 104-106). Furthermore, as shown in FIGS. 107-108, a sealing device 610 can cooperate with a plurality of projections 612 extending from a valve, as well as a hooked attachment member 614 that is inserted into tissue as an anchoring structure.

Figure 109:
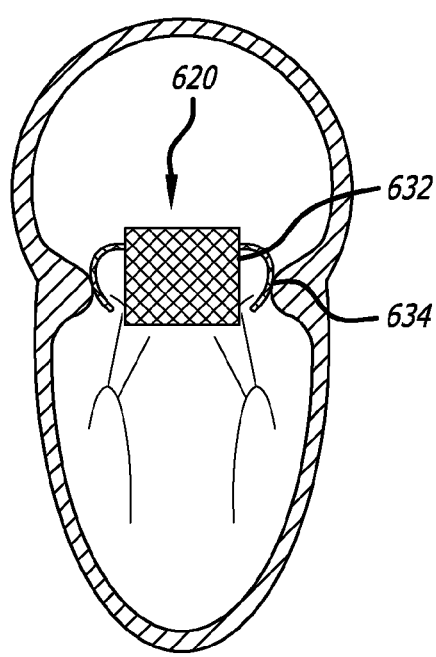
FIG. 109 is a cross sectional view, depicting a sealing mechanism comprising a membrane perimeter.
Figure 110:
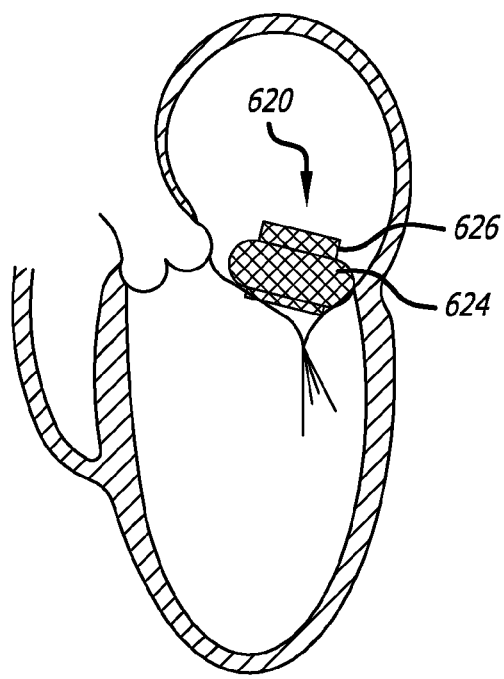
FIG. 110 is a side view, depicting the sealing structure of FIG. 109.
Figure 111:
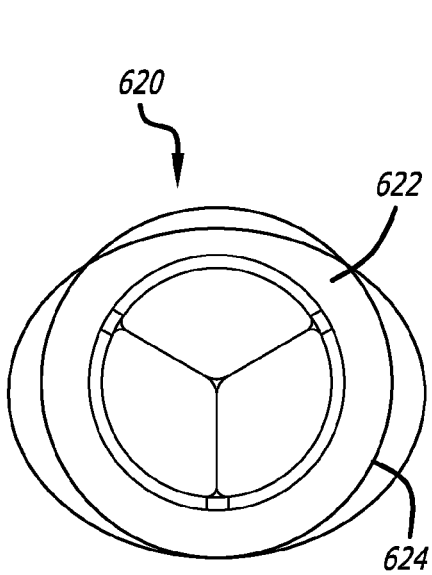
FIG. 111 is a top view, depicting the structure of FIGS. 109 and 110.
Figure 112:
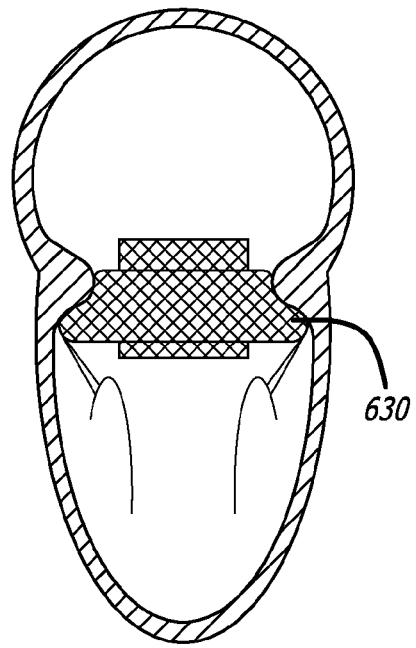
FIG. 112 is a side view, depicting a wire frame structure attached to the artificial valve.
Figure 113:
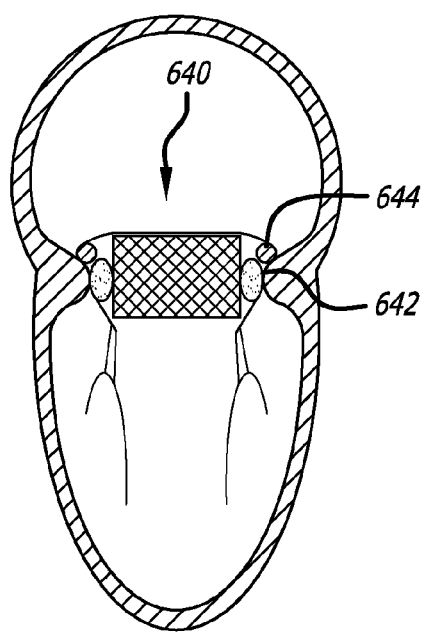
Figure 114:
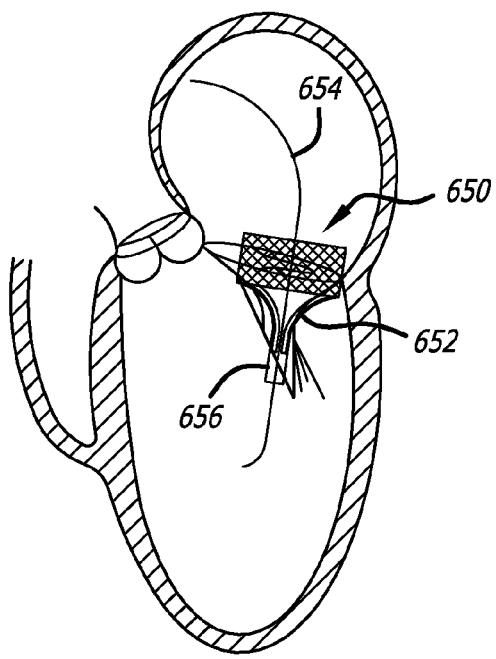
Figure 115:
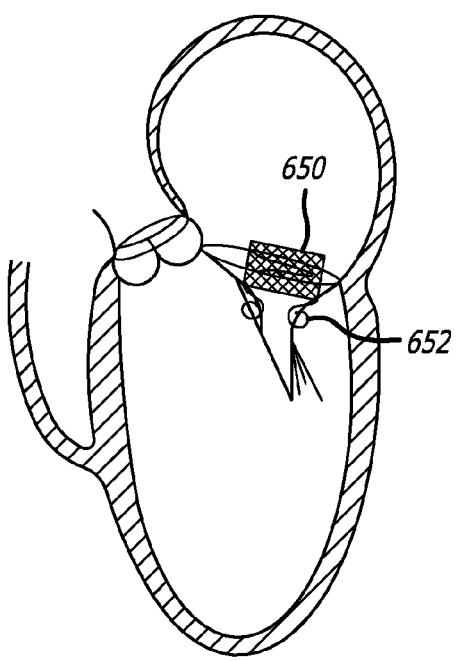
Figure 116:
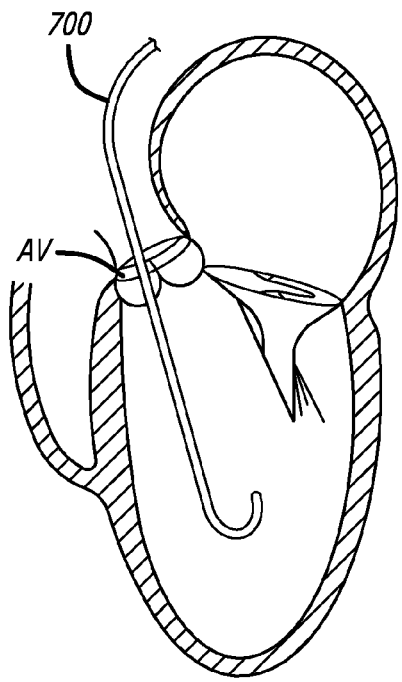

Various other tubular sealing assemblies are shown in FIGS. 109-115. Turning in particular to FIGS. 109-111, a tubular sealing assembly 620 can include an expandable tubular frame 622 and a membrane perimeter 624 extending about a midsection thereof. Upon expansion of the tubular frame 622, the midsection of the frame 622 opens to the profile defined by the membrane 624 to thereby present a sealing interface structure. Alternatively, an expandable wire frame 630 can be unconstrained by a membrane and extend to match body anatomy (FIG. 112) or it can be a sealing device 640 including a compressible material band 642 about its midsection as well as an additional sealing ring 644 (See FIG. 113) attached to its leading edge.

In yet another approach (See FIGS. 114-115), the sealing device 650 can include a pair of wire extensions 652 sized and shaped to extend within the LV between papillary muscles. A wire 654 with a sheath 656 at is tip can be used during delivery of the sealing device 650 to the implantation site. Once placed as desired, the structure can be disengaged from the wire extensions 652, permitting them to engage supporting anatomy within the LV. In order to provide a surface to capture anterior and posterior leaflets, the wire extensions can assume a coiled configuration when deployed.

The delivery system and method used to deliver the anchor system can depend on both the structure and type of materials used for the anchor, as well as the desired route of access for implantation, and the type of deployment of the anchor. An anchor delivery system can generally include a guide catheter and an anchor delivery catheter, either as separate components, or integrated together. The guide catheter may include specific curves to facilitate navigation into the atrium or ventricle and may also include a steerable torquable shaft to aid with anchor positioning or orientation. The guide catheter may further include a deflectable tip region. The anchor delivery catheter can house or hold the collapsed anchor during delivery and deployment and may include delivery tubes or wires that are releasably connected to the anchor. Other elements such as shaft dividers may be utilized to help with managing multiple connection shafts as well as orientation of the anchor during deployment. Additional components inside the connection shaft or wires, or deliverable through or over, may include tissue penetrating elements to aid with overall securement and anchoring. A proximal hub can be configured to function to selectively manipulate, seal, and deploy certain elements. It is contemplated that structures can be incorporated onto the anchor to allow for a percutaneous delivery and include the use of super elastic Nitinol for the primary skeleton of the anchor or the use of a malleable SST or a similar material that could be folded down inside the delivery catheter but then balloon expanded against the tissue interface and would conform mitral tissue interface. The use of heat set small radii in certain locations of the anchor structure can allow for folding to fit inside delivery catheter where the strain limit of the material is not exceeded. Also, the use of ribbon at certain locations within the anchor skeletal structure can allow for tight bends in the thinner dimension for bending inside catheter, but still achieve the structural rigidity required if the broader section of ribbon is properly oriented when deployed. Smaller and larger diameter wire can also be used to vary the configuration to allow for bending/collapse in the catheter while still having the necessary structural strength and interface when deployed.

It is further contemplated that the anchor structures allow for arterial (aorta-retrograde), venous (via transatrial septum-antegrade), trans-apical (LV), or trans-atrial via a right thoracotomy access into the left atrium. Because of the relatively small size of the anchor, the ability to compress or fold the anchor into a small delivery configuration (especially with Nitinol or malleable stainless), and the separation of the anchor from the valve, the arterial route is feasible and may be especially useful in the situation where the anchor is deployed at the time of a diagnostic angiogram that is in advance of the actual valve therapy (separate procedures), as the arterial groin access has already been created. Routes of access can include arterial, venous and/or thorax/apical.

To deploy the anchor into the heart, both catheter sheath retraction and anchor push out of sheath are contemplated approaches. Also, to have the anchor achieve the desired configuration inside the heart, either a self-expanding anchor, or use of balloon expansion to expand the anchor, or components of both are contemplated.

For anchors that are supra-annular with commissural feet, delivery system connections to the tips of the commissural feet or projections can facilitate positioning and proper orientation and seating into the mitral orifice. In this regard, the anchor and connections would exit the delivery catheter while the catheter tip was residing in the left atrium. The delivery sheath could then be pulled down beneath the level of the mitral annulus allowing the shaft connections to the feet to orient and align with the commissural clefts of the anterior annulus between the anterior and posterior native leaflets. As the shaft connections are pulled, the commissural feet would move toward the edge and bring the feet into position next to the LV wall within the natural leaflet cleft. Once in this position, additional features of the implants could be deployed or delivered via the shaft connections used to aid in attaching the feet to the wall/leaflet tissue, e.g. staple, barbed hooks or nails. Similar feet could be utilized for orientation along the clefts seen naturally on the P1 and P3 regions of the posterior leaflet.

According to one aspect, an exemplary embodiment of the delivery system utilizes an outer delivery or guide catheter that has a pre-formed curve that positions the anchor delivery catheter into the proper orientation toward the mitral valve from the LV. For retrograde access to the LV from the aorta, curves ranging from 90 to 200 degrees may be used. A pre-formed shaft separator or a shaft separator with prespecified bending moments within the guide catheter can also aid in orienting and positioning the anchor and associated connection shafts.

According to another aspect, an exemplary embodiment of a delivery system may include connection shafts to connect to and control movement of the commissural feet of the anchor being deployed. The connection shafts can be tubular or wire structures or combinations that can releasably disengage from the anchor after positioning. These connection shafts can allow for independent manipulation of the anchor at each individual point of attachment.

The anchor securement elements can be deployed utilizing the two basic structures of the shaft connections to the anchor frame and/or projections, namely the tubular shaft and the wire connections providing the temporary securement. The tubular shaft can be retracted to deploy an expanding frame element housed inside the shaft during frame delivery. Also, the tubular shaft can be used as a conduit to deliver a separate structure to the attachment location and/or to expose or deploy a securement element and then used to either actuate or drive the element by re-advancing the tube. Further, a wire element can be used as a conduit or rail to deliver a separate structure to the attachment location. The wire element can also be used to deploy or push out an element loaded/housed inside the tube/wire structure and/or the wire structure can be used by rotating an element connected at its tip to deliver the securement element.

Figure 117:
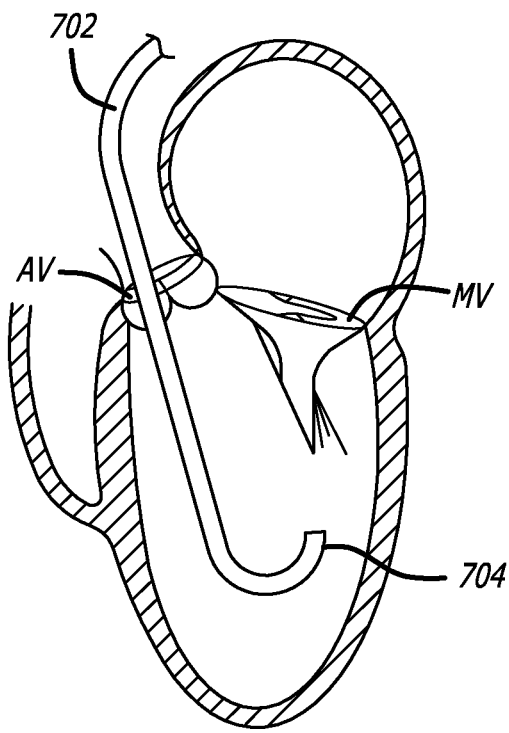
Figure 118:
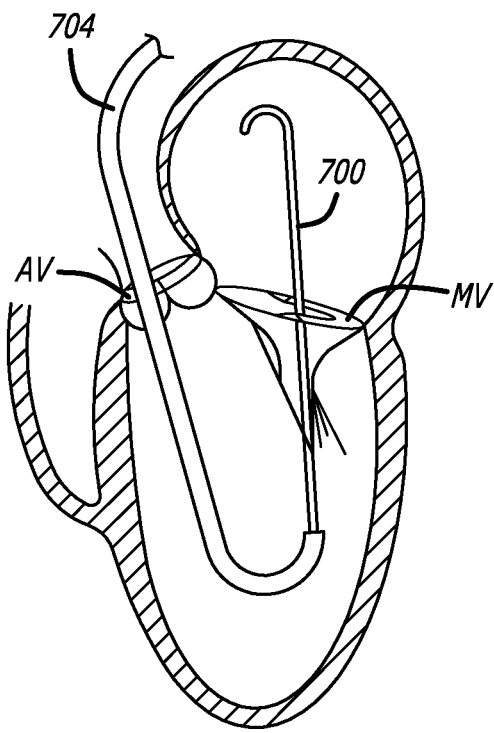
Figure 119:
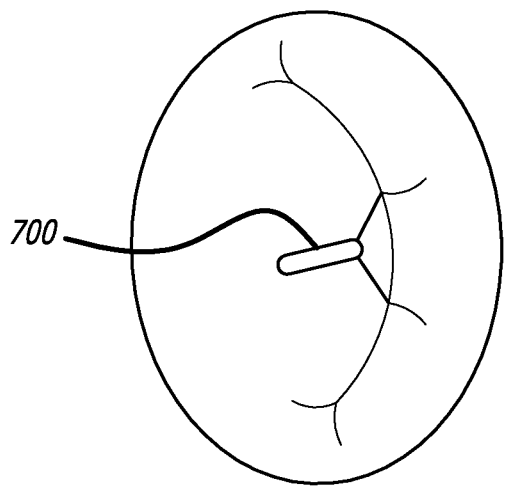

With reference to FIGS. 116-127, one delivery system and method is presented. In a first step (FIG. 116), a j-tip guidewire 700 is advanced within the heart through the aortic valve AV. Conventional methods including those outlined above are employed to gain access to the aorta. Next, an intraventricular guide catheter 702 is advanced over or along the guidewire 700 (FIG. 117). The distal tip 704 of the guide catheter 702 is oriented toward the mitral valve MV, with a curve plane of the catheter being parallel to the A2/P2 orientation. The guidewire 700 (or a second guidewire) is then advanced through the orifice of the mitral valve MV, thereby providing a platform for placing structure across the mitral valve MV (See FIGS. 118-119).

Figure 120:
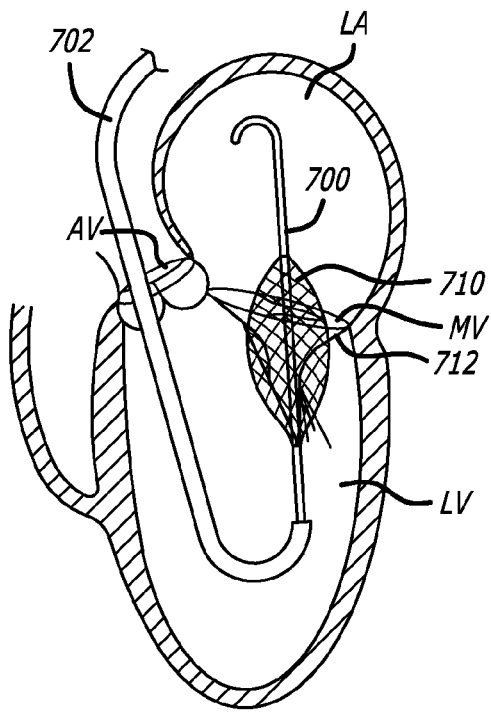
Figure 121:
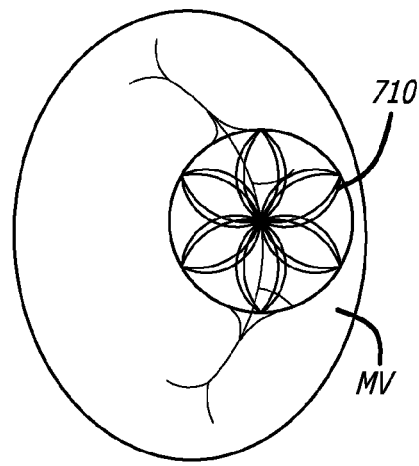

With the guidewire 700 across to the mitral valve MV, a balloon or expandable cage 710 is configured within the orifice of the mitral valve MV (See FIGS. 120-121). It is to be recognized that the guidewire 700 can be equipped with the balloon or expandable cage 710, or a separate device can be advanced over the guidewire 700, and the balloon or cage 710 placed within the orifice of the mitral valve MV. In one embodiment, structure is provided to withdraw a distal portion of the balloon or cage 710 relative to proximal structure to thereby expand the balloon or cage 710, or a sleeve structure can be advanced relative to a distal portion of the balloon or cage to accomplish the expansion. It is also contemplated that the balloon or cage 710 be expanded in the left atrium LA and then withdrawn within the orifice of the mitral valve 710 to ensure there is no entanglement with cords 712 supporting the mitral valve with any portion or components of the delivery system. The balloon or cage 710 is then contracted and removed from within the orifice of the mitral valve MV, or otherwise covered with other structure of the delivery system.

If the wire cage meets a restriction, the cage can be collapsed and it and wire can be withdrawn back into guide and non-entangled wire access attempted again. Alternatively, the expanded wire cage could be advanced first until it passes mitral orifice without restriction. The size of the cage is large enough to fit through orifice but not between chordae attached to the same papillary muscle, and traverses between chordal tent and anterior and posterior leaflets. The wire is then advanced into atria to provide anchor system delivery that does not entangle with subvalvular mitral apparatus. Alternatively, a balloon tipped catheter can be utilized instead of a cage. Once the wire is successfully placed, the wire cage or balloon system is removed from body leaving wire access for the next steps of anchor delivery.

Figure 122:
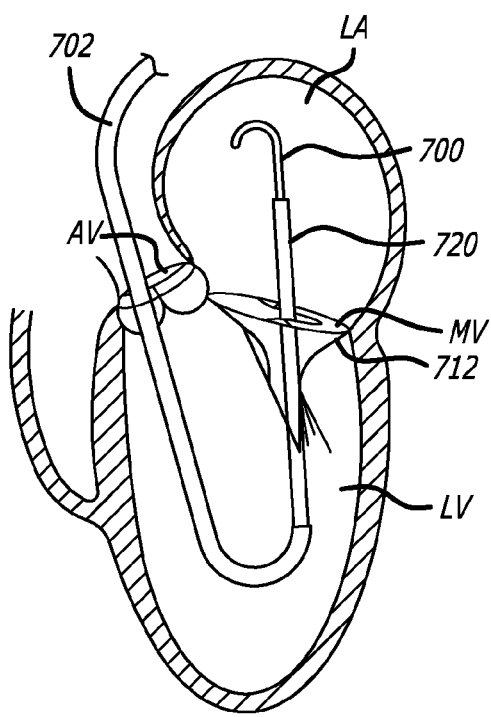
Figure 123:
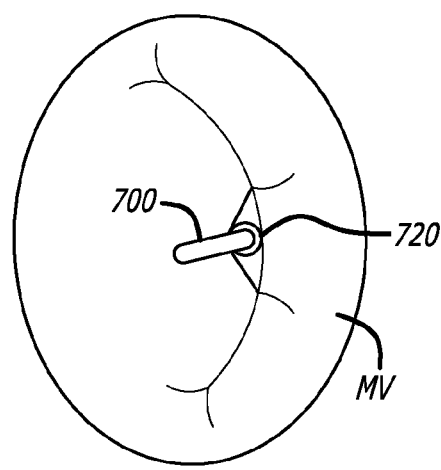
Figure 124:
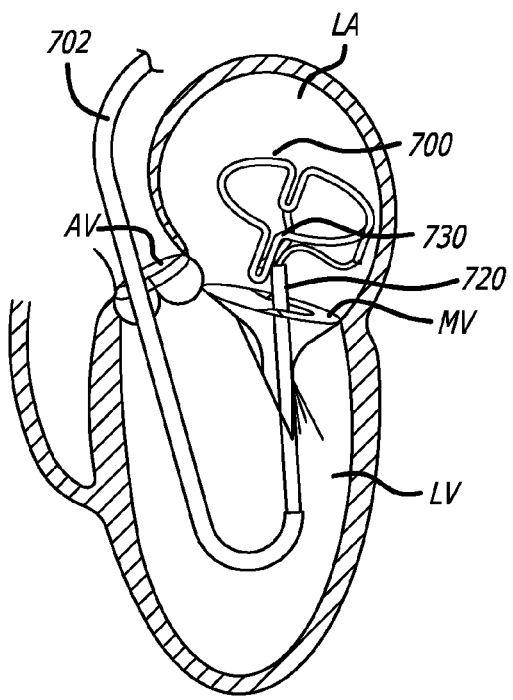
Figure 125:
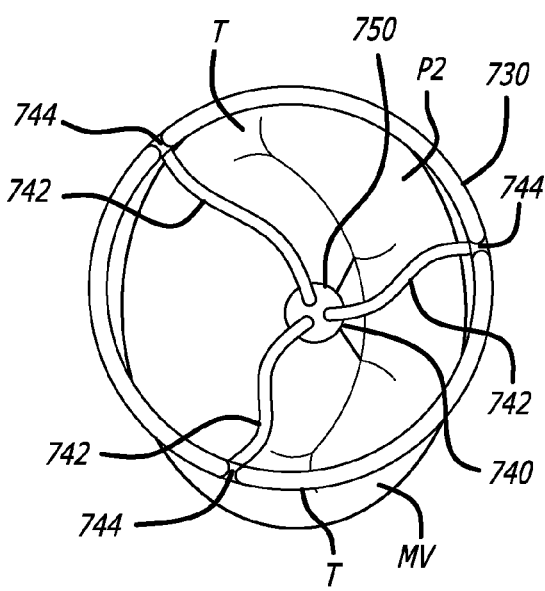

As shown in FIGS. 122 and 123, an anchor delivery catheter 720 is next advanced over the guidewire 700 and within the guide catheter 702. A length of the anchor delivery catheter 720 is placed across the orifice of the mitral valve MV. Subsequently (See FIGS. 124 and 125), the anchor implant 730 is advanced out of a terminal end of the anchor delivery catheter 720 and into the left atrium LA. Proper orientation of the anchor implant 730 is provided by a plurality of connection wires 740. Such wires 740 are each connected to a single commissural projection 744 of the anchor implant 740, so that one commissural projection 744 is aligned with each trigone T, and one commissural 744 is aligned with the posterior leaflet segment P2. Connection between wires 740 and commissural projection 744 is maintained until proper positioning is ensured, and so that reorientation and retrieval is possible.

Once the positioning of the anchor implant 740 is verified, the anchor delivery catheter 720 and connection wires 742 are withdrawn to place the anchor implant 740 within the annulus of the mitral valve MV. When placed as desired, a commissural projection 744 is placed at each the trigone T, and one at P2 (See FIGS. 126-127). As can be best appreciated from FIG. 125, a shaft 750 having three or more longitudinal bores formed therein can be employed to push the anchor implant 720 out from an interior of the anchor delivery catheter 720. The longitudinal bores provide conduits for the connection wires 742 used to orient the anchor implant 730. A central longitudinal bore (not shown) can be further provided to receive the guidewire 700; however, in the event the shaft 750 does not include a central bore, the guidewire 700 is removed from the interventional site prior to the advancement of the anchor delivery catheter 720 within the guide catheter 702.

In an alternative approach to the anchor delivery catheter (See FIGS. 128-132 shown without an anchor), a longitudinal shaft separator 760 can be employed in place of the above-described shaft. Thus, rather than have a plurality of longitudinal bores sized to receive the connection wires 742, the shaft separator 760 includes a plurality of splines 762 extending from a central core to define spaces for the connection wires 747. A central bore 764 is further provided to slidingly receive the guidewire 700. As shown in FIGS. 128 and 129, the splines 762 can be placed at varying locations to facilitate proper orientation of structure within the anchor delivery catheter 720 such as by auto-orienting connection wires to a plane of the oriented guide catheter. For example, one spline 766 can be sized and positioned to orient along an inner radius 768 of a curve of the delivery system (See FIG. 132). The curve of the shaft separator 760 aligns and maintains rotational orientation of the separator splines relative to the curve of the anchor delivery catheter 720 or the guide catheter 768.

Moreover, with reference to FIGS. 133-135, various alternatives are presented regarding releasable connections between commissural projections and structure of the anchor delivery system 720. In one approach (See FIGS. 133-134), a commissural projection 770 of an anchor implant can include a deployable staple 772. The deployable staple 772 is configured within the anchor delivery catheter or a separate sheath 774 of the anchor delivery system. A positioning rod 776 with a threaded terminal end is joined to internal threads formed within the deployable staple 772 to define a threaded connection 778 between the parts. Further, a retainer cord 780 is placed through the sheath 774, the same including a loop 782 configured about the positioning rod 776 and a terminal end 784 engaging the commissural projection 770. In this way, distinct point controls are provided to separately position and deploy the staple 772 and the commissural projection 770. That is, the retainer cord 780 can be withdrawn from engagement with the commissural projection 700 to facilitate its implantation separately from deploying the staple by rotating the position rod 770 from engagement with the staple 771.

In an alternative approach (See FIG. 135), a threaded connection 790 can be provided between a threaded receiver 792 formed on the anchor itself, and a threaded connection wire 794. Here, a delivery connector tube 796 includes a first large bore 797 sized to receive the commissural projection 798, and a second smaller bore sized to slidingly receive the connector wire 794. Again, distinct point control is provided in that the commissural projection 798 can be released independently of disengagement of the threaded connection 790.

Percutaneous, or minimally invasive trans-apical, valve delivery systems typically can be over the wire systems with the valve assembly compressed or crimped into the delivery state. To expose the valve, the outer catheter structure or sheath can either be withdrawn or the implant pushed or expelled from the outer catheter. The tip of the valve delivery system can also include a tapered and flexible tip section to facilitate navigation and tracking of the system within the vasculature or heart. Once exposed the valve is either self-expanding or balloon expanding. Some releasable connection shafts or wires to the valve frame may also be incorporated to facilitate positioning and orientation.

Various loading methods and structures are contemplated. Tools such as crimping devices can be utilized for compressing the valve down onto the delivery catheter shaft and into a deliverable configuration and size. Moreover, a primary route of access for a replacement mitral valve can be via a venous trans-septal antegrade approach. It is also anticipated a transapical approach can be utilized. A transatrial approach via a right thoracotomy to gain access to the left atrium can also be used and may be useful when utilizing a mechanical valve for implantation. Thus, routes of access can include arterial, venous and/or thorax/apical.

Various deployment methods are also contemplated. The deployment of the valve can utilize any of the current techniques being employed for percutaneous pulmonic or aortic implantation. This includes retraction of a sheath or advancement of the valve inside the sheath to have the valve exit the delivery catheter. Once exited, either partially or completely, the final valve deployment could include self-expansion or balloon expansion. With either of these final deployment techniques, a nondeployed interlock structure/mechanism on the perimeter of the artificial valve could provide a temporary space for flow communication of the atria with the ventricle during diastole during artificial valve expansion. Upon completion of artificial valve expansion, it would now be functional and the interlock mechanism could now be deployed to complete the anchoring and sealing of the artificial valve. This particular embodiment can eliminate the conventional need for rapid pacing during valve deployment; there is flow allowed during diastole while valve is deployed. Therefore, each of retraction, push, self-expanding, and balloon approaches are contemplated.

With respect to orientation/positioning methods, utilizing a separately implanted anchor substrate is the ability to utilize a fluoroscopic alignment technique to mesh the anchor with the valve. In this scenario, the x-ray fluoroscopic camera could be adjusted so a radiopaque (complete or interrupted around perimeter) anchor structure would be visualized in a relatively straight line (camera orientation—line connecting emitter with intensifier—is perpendicular to anchor circular axis, or parallel to plane of anchor ring). The valve frame structure could similarly have a radiopaque perimeter at the point at or near the interlock region with the anchor. When the anchor was viewed in the manner described, the valve axial orientation could be adjusted so the radiopaque perimeter was also a line (without moving camera position) meaning the two cylindrical axes of the anchor and valve were now parallel. Subsequently, the valve line could be appropriately positioned above, below, or at the interlock region. This linear alignment of the two radiopaque structures would be even more visually pronounced as the valve frame was being expanded/deployed, whether by balloon or self-expanding. This could additionally allow for fine tuning or adjustment prior to final engagement of the valve with the anchor structure.

With references to FIGS. 136-142, various steps to placement of an artificial mitral valve are presented. FIG. 136 shows the anchor delivery system 800 placed within the heart subsequent to implantation of an anchor implant 802. In one approach, the anchor implant 802 is left to heal in place prior to deployment of the artificial valve. Alternatively, as stated above, valve implantation can be conducted along with or just subsequent to the placement of the anchor implant 802. Using a transarterial approach, as shown in FIGS. 137-138, an artificial valve delivery system 810 is advanced in a transvenous, trans-septal approach to position an artificial valve 820 into engagement with the anchor implant 802. In order to properly orient the anchor implant 802 and valve 810 relative to each other, each of the anchor implant and valve can include radiopaque markers. Anchor radiopaque markers 822 and valve radiopaque markers 824 can thus be aligned both longitudinally or axially (See FIGS. 139-140) as well as rotationally (See FIGS. 141-142). In this context, a fluoroscopic camera (not shown) can be employed to guide the relatively positional relationship between anchor 822 and valve 824 markers. It is to be further noted that radiopaque markers residing on a commissural projection of an anchor implant can further be used to ensure that they are seated as desired between commissures, and markers located on a ring portion of an implant can be used to locate such structure at a valve annulus.

Turning now to FIGS. 143-146 and FIGS. 147-150, an alternative trans-atrial approach and a trans-apical approach to artificial valve delivery are depicted. Here, a valve delivery system includes an introducer tool 828 which is insertable through a portal assembly 830. The portal assembly 830 has a generally flat, oval cross-sectional profile intended to present a less invasive structure to heart tissue. The introducer tool 828 further includes an articulating terminal end portion 832 adapted to releasably hold an artificial valve 834. The terminal end portion 832 is configured to retain a tilted valve 834 (See FIGS. 143-144 and 147-148) for insertion into an interior of the heart through the portal assembly 830, and is articulatable so that the artificial heart valve 834 can be turned and placed into engagement with an anchor implant 840 previously delivered at the native valve (See FIGS. 145-146 and 149-150). Notably, the portal assembly 830 further includes purse string sutures 842 configured about an exterior surface of a portion of the assembly located at the point of heart insertion. Upon removing the portal assembly 830 from the interventional site, the purse strings are intended to remain in place on the heart and are thus available to close the access point employed for the valve insertion. In this way, the implantation procedure is completed expeditiously with a repaired access point.

Further modifications and alternative embodiments will be apparent to those of ordinary skill in the art in view of the disclosure herein. For example, the systems and the methods may include additional components or steps that were omitted from the diagrams and description for clarity of operation. Moreover, those of ordinary skill in the art will appreciate that aspects and/or features disclosed with respect to one embodiment in some case may be incorporated in other embodiments even if not specifically described with respect to such other embodiments. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims. Accordingly, this description is to be construed as illustrative only and is for the purpose of enabling those skilled in the art the general manner of carrying out the present teachings. It is to be understood that the particular examples and embodiments set forth herein are nonlimiting, and modifications to structure, dimensions, materials, and methodologies may be made without departing from the scope of the present teachings. Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

Thus, it will be apparent from the foregoing that, while particular forms of the invention have been illustrated and described, various modifications can be made without parting from the spirit and scope of the invention.

We claim:

1. A mitral valve replacement system configured to be implanted in multiple stages to treat a heart having a mitral valve including commissural clefts, at least a posterior leaflet and an anterior leaflet to provide a mitral valve leaflet function of occluding flow during systole and opening flow during diastole, and an annulus, comprising: an anchoring structure including a supra-annular retention structure and anchoring elements that are configured to engage sub-annular structure of the mitral valve to position the anchoring structure relative to the mitral valve without significantly interrupting the mitral valve leaflet function of occluding flow during systole and opening flow during diastole; and an artificial valve configured to be received by the supra-annular retention anchoring structure after the anchoring structure is placed separately within the heart; wherein the artificial valve is sized and shaped such that an upper portion of the artificial valve mates with the supra-annular retention structure at a position spaced supra-annularly of the mitral valve annulus while a lower portion of the artificial valve extends to a position sub-annularly of the mitral valve annulus, wherein the anchoring elements of the anchoring structure comprise a plurality of wire loop projections configured to pass through a commissural cleft and the engage sub-annular structure.

2. The mitral valve replacement system of claim 1, wherein the anchoring structure is sized and shaped to be implanted at a mitral valve annulus without reshaping the annulus.

3. The mitral valve replacement system of claim 1, the anchoring structure further comprising a projection configured to engage the mitral valve annulus along a posterior leaflet.

4. The mitral valve replacement system of claim 1, the anchoring structure further comprising annulus engaging structures having shapes configured to mimic contours of the annulus of the mitral valve.

5. The mitral valve replacement system of claim 1, wherein the anchoring structure is movable between a compressed configuration and an expanded configuration.

6. The mitral valve replacement system of claim 1, wherein the anchoring structure is configured for tissue ingrowth.

7. The mitral valve replacement system of claim 1, the anchoring structure further comprising projections configured to engage a mitral valve trigone.

8. A mitral valve replacement system configured to be implanted in multiple stages to treat a heart having a mitral valve including commissural clefts, at least a posterior leaflet and an anterior leaflet to provide a mitral valve leaflet function of occluding flow during systole and opening flow during diastole, and an annulus, comprising: an anchoring structure including a supra-annular ring-like structure and anchoring elements that are configured to engage sub-annular structure of the mitral valve to position the anchoring structure relative to the mitral valve without significantly interrupting the mitral valve leaflet function of occluding flow during systole and opening flow during diastole; and an artificial valve configured to be received by with the supra-annular ring-like anchoring structure after the anchoring structure is placed separately within the heart; wherein the artificial valve is sized and shaped such that an upper portion of the artificial valve mates with the supra-annular ring-like structure and remains spaced supra-annularly of the mitral valve annulus while a lower portion of the artificial valve extends to a position sub-annularly of the mitral valve annulus, wherein the anchoring elements of the anchoring structure comprise a plurality of wire loop projections configured to pass through a commissural cleft and the engage sub-annular structure.

9. The mitral valve replacement system of claim 8, wherein the anchoring structure is sized and shaped to be implanted at a mitral valve annulus without reshaping the annulus.

10. The mitral valve replacement system of claim 8, the anchoring structure further comprising a projection configured to engage the mitral valve annulus along a posterior leaflet.

11. The mitral valve replacement system of claim 8, wherein the anchoring structure has a curved portion.

12. The mitral valve replacement system of claim 8, wherein the anchoring structure is movable between a compressed configuration and an expanded configuration.

13. A mitral valve replacement system configured to be implanted in multiple stages to treat a heart having a mitral valve including commissural clefts, at least a posterior leaflet and an anterior leaflet to provide a mitral valve leaflet function of occluding flow during systole and opening flow during diastole, and an annulus, comprising: an anchoring structure including a supra-annular retention structure and anchoring elements that extend below the supra-annular retention structure and are configured to engage sub-annular structure of the mitral valve to position the anchoring structure relative to the mitral valve without significantly interrupting the mitral valve leaflet function of occluding flow during systole and opening flow during diastole; and an artificial valve configured to sealingly engage with natural tissue and to be received by the supra-annular retention anchoring structure after the anchoring structure is placed separately within the heart; wherein the artificial valve is sized and shaped such that an upper portion of the artificial valve mates with the supra-annular retention structure at a position spaced supra-annularly of the mitral valve annulus while a lower portion of the artificial valve extends to a position sub-annularly of the mitral valve annulus, wherein the anchoring elements of the anchoring structure comprise a plurality of wire loop projections configured to pass through a commissural cleft and the engage sub-annular structure.

14. The mitral valve replacement system of claim 13, wherein the anchoring structure is sized and shaped to be implanted at a mitral valve annulus without reshaping the annulus.

15. The mitral valve replacement system of claim 13, the anchoring structure further comprising a projection configured to engage the mitral valve annulus along a posterior leaflet.

16. The mitral valve replacement system of claim 13, wherein the seal is created by sealing against a native leaflet.

17. The mitral valve replacement system of claim 16, wherein the seal is created without reshaping the annulus.

* * * * *